United States Patent
Aburatani et al.

(10) Patent No.: US 9,274,119 B2
(45) Date of Patent: Mar. 1, 2016

(54) ANTI-CLDN6 ANTIBODY

(75) Inventors: Hiroyuki Aburatani, Tokyo (JP); Shuichi Tsutsumi, Tokyo (JP); Kunihiro Nishimura, Tokyo (JP); Hirofumi Sakumoto, Tokyo (JP); Shigeto Kawai, Tokyo (JP)

(73) Assignees: THE UNIVERSITY OF TOKYO, Tokyo (JP); CHUGAI SEIYAKU KABUSHIKI KAISHA, Tokyo (JP)

( * ) Notice: Subject to any disclaimer, the term of this patent is extended or adjusted under 35 U.S.C. 154(b) by 438 days.

(21) Appl. No.: 12/735,359

(22) PCT Filed: Jan. 9, 2009

(86) PCT No.: PCT/JP2009/000082
§ 371 (c)(1),
(2), (4) Date: Aug. 23, 2010

(87) PCT Pub. No.: WO2009/087978
PCT Pub. Date: Jul. 16, 2009

(65) Prior Publication Data
US 2011/0059469 A1 Mar. 10, 2011

(30) Foreign Application Priority Data
Jan. 11, 2008 (JP) ................................. 2008-004423

(51) Int. Cl.
*C07K 16/28* (2006.01)
*G01N 33/574* (2006.01)
*A61K 39/00* (2006.01)

(52) U.S. Cl.
CPC .......... *G01N 33/57484* (2013.01); *C07K 16/28* (2013.01); *G01N 33/57492* (2013.01); *A61K 2039/505* (2013.01); *C07K 2317/732* (2013.01); *C07K 2317/734* (2013.01)

(58) Field of Classification Search
CPC ............. C07K 16/28; C07K 2317/734; C07K 2317/732; G01N 33/57484
USPC .......................... 424/133.1; 530/387.3, 389.7
See application file for complete search history.

(56) References Cited

U.S. PATENT DOCUMENTS

| | | |
|---|---|---|
| 6,830,894 B1 | 12/2004 | Blaschuk et al. |
| 2004/0132101 A1 | 7/2004 | Lazar et al. |
| 2006/0062727 A1 | 3/2006 | Philips et al. |
| 2007/0148170 A1 | 6/2007 | Desjarlais et al. |

FOREIGN PATENT DOCUMENTS

| | | |
|---|---|---|
| CA | 2379661 A1 | 9/2003 |
| JP | 2003-524384 A | 8/2003 |
| JP | 2006-500009 A | 1/2006 |
| JP | 2006-512407 A | 4/2006 |
| JP | 2007-525443 A | 9/2007 |
| WO | 00-26360 A1 | 5/2000 |
| WO | 03-088808 A2 | 10/2003 |
| WO | 2004-004662 A2 | 1/2004 |
| WO | WO 2004/003019 * | 1/2004 |
| WO | 2004-029207 A2 | 4/2004 |
| WO | 2004-099249 A2 | 11/2004 |

OTHER PUBLICATIONS

Arabzadeh et al. (BMC Cancer 7:196-203 (Oct. 18, 2007).*
Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
About.com; p. 1; definition for "Antibody avidity"; Apr. 2, 2013.*
International Search Report for PCT/JP2009/000082; Feb. 10, 2009.
Arabzadeh A et al; Changes in the Distribution Pattern of Claudin Tight Junction Proteins During the Progression of Mouse Skin Tumorigenesis. In: BMC Cancer, vol. 7:196; Oct. 18, 2007; pp. 1-8.
Product Specification: "Monoclonal Anti-human Claudin-6 Antibody." R&D Systems, Inc. (1-800-343-7475); catalog No. MAB3656; Aug. 17, 2006. 1 page.
Quan, C et al.; Identification of Genes Preferentially Expressed in Mammary Epithelial Cells of Copenhagen Rat Using Subtractive Hybridization and Microarrays. Carcinogenesis vol. 24 (10); Aug. 2003; pp. 1593-1599.
Osanai, M et al.; Epigenetic Silencing of Claudin-6 Promotes Anchorage-Independent Growth of Breast Carcinoma Cells. Cancer Science vol. 98 (10); Oct. 2007; pp. 1557-1562.
Morita, K et al.; Claudin Multigene Family Encoding Four-Transmembrane Domain Protein Components of Tight Junction Strands. Proc Natl Acad Sci USA, Cell Biology vol. 96; Jan. 1999; pp. 511-516.

(Continued)

Primary Examiner — Lynn Bristol
(74) Attorney, Agent, or Firm — Sughrue Mion, PLLC

(57) ABSTRACT

The present invention relates to an antibody binding to Claudin6 (CLDN6) expressed on a cell membrane. The antibody of the present invention recognizes human CLDN6 present in a native form on cell membrane surface and exhibits cytotoxicity through ADCC and/or CDC activities against cancer cell lines highly expressing human CLDN6. Moreover, the antibody of the present invention has cell growth inhibitory effect through conjugation with toxin on cancer cell lines highly expressing human CLDN6. The human CLDN6 is overexpressed in tumor tissues (lung adenocarcinoma, gastric cancer, and ovarian cancer), although its expression is not observed in normal tissues. Thus, the anti-CLDN6 antibody is expected to highly accumulate in tumors highly expressing human CLDN6 and can serve as a very effective antitumor agent.

9 Claims, 15 Drawing Sheets
(2 of 15 Drawing Sheet(s) Filed in Color)

(56) References Cited

OTHER PUBLICATIONS

Nimmerjahn, F et al.; Fcγ Receptor: Old Friends and New Family Members. Immunity 24; Jan. 2006; pp. 19-28.

Nimmerjahn, F et al.; Divergent Immunoglobulin G Subclass Activity Through Selective Fc Receptor Binding. Science vol. 310; Dec. 2005; pp. 1510-1512.

Kohls, MD et al.; MAB-ZAP: A Tool for Evaluating Antibody Efficacy for Use in an Immunotoxin. Product Application Focus, BioTechniques vol. 28 (1); Jan. 2000; pp. 162-165.

Rahner, C et al.; Heterogeneity in Expression and Subcellular Localization of Claudins 2, 3, 4, and 5 in the Rat Liver, Pancreas, and Gut. Gastroenterology vol. 120; Feb. 2001; pp. 411-422.

Wilcox, ER et al.; Mutations in the Gene Encoding Tight Junction Claudin-14 Cause Autosomal Recessive Deafness DFNB29. Cell vol. 104; Jan. 2001; pp. 165-172.

Furuse, M et al.; Claudins in Occluding Junctions of Humans and Flies. Trends in Cell Biology vol. 16 (4); Apr. 2006; pp. 181-188.

Extended European Search Report dated Aug. 9, 2012 issued in corresponding European Patent Application No. 09700588.8.

Morita K, et al; Endothelial Claudin: Claudin-5/TMVCF Constitutes Tight Junction Strands in Endothelial Cells, The Journal of Cell Biology, 1999, pp. 185-194, vol. 147, No. 1.

Offner S, et al; Epithelial Tight Junction Proteins as Potential Antibody Targets for Pancarcinoma Therapy, Cancer Immunol Immunother, 2005, pp. 431-445, vol. 54, No. 5.

Greenbaum et al., "Comparing protein abundance and mRNA expression levels on a genomic scale", Genome Biology, 4(9):117. 1-117.8 (2003).

Hewitt et al., "The Claudin Gene Family: Expression in Normal and Neoplastic Tissues," BMC Cancer, 2006, 6(186): pp. 1-8.

\* cited by examiner

ANTI-CLDN6 ANTIBODY

TECHNICAL FIELD

The present invention generally relates to an antibody drug. More specifically, the present invention relates to an anti-CLDN6 antibody and a cell growth inhibitor and an anticancer agent comprising this antibody.

BACKGROUND ART

Claudin family is the family of cell membrane proteins of approximately 23 kD in molecular weight which have four transmembrane domains and constitute tight junctions. The Claudin family includes 24 members in humans and mice, and each member of the Claudins is known to exhibit a very unique expression pattern depending on each epithelial cell type (Non-Patent Document 1 (Furuse and Tsukita, TRENDS in Cell Biology 2006, 16: 181); Non-Patent Document 2 (Wilcox, et al., Cell 2001, 104: 165); Non-Patent Document 3 (Rahner, et al., GASTROENTEROLOGY 2001, 120: 411); and Non-Patent Document 4 (Morita, et al., Proc. Natl. Acad. Sci. USA 1999, 96: 511)). In the sheet of epithelial cells, a mechanism works to prevent substances from leaking (diffusing) in the intercellular spaces, and cell-cell adhesion systems called tight junctions have been shown to really play a central role as a "barrier" in the mechanism to prevent leakage.

Non-Patent Document 5 (Hewitt, et al., BMC Cancer 2006, 6: 186) or Patent Document 1 (WO 2003/088808) or the like has unveiled the high expression of human CLDN6 transcripts in cancer. Moreover, Non-Patent Document 6 (Osanai, et al., Cancer Sci. 2007, 98: 1557) and Non-Patent Document 7 (Azadeh Arabzadeh, et al., BMC Cancer 2007, 7: 196) contain a mention to human and mouse CLDN6 expressions at protein levels in cancer. Non-Patent Document 6 has demonstrated CLDN6 expression by western blot analysis using a breast cancer cell line MCF7. This document has claimed, as described in the title, that epigenetic silencing of human CLDN6 in the breast cancer cell line promotes anchorage-independent growth of the cancer cells. Non-Patent Document 6 discloses that in the MCF7 cell line, the expression of human CLDN6 serving as a tumor suppressor gene is decreased due to the partial methylation of the promoter region, resulting in reduced apoptotic sensitivity and the diminished ability to form colony, and this decreased expression also causes increase in cancer cell invasiveness and in metalloproteinase activity and the enhanced ability of the cancer cells to migrate and thus contributes to the malignant alteration of cancer.

However, the western blot conducted in Non-Patent Document 6 on human CLDN6 in MCF7 cells is meant to be an experiment to confirm whether the system of siRNA knockdown of human CLDN6 functions. Thus, this document has made no mention of antibodies as materials used or of methods. Moreover, the experiment is not aimed at examining the degree of change in the expression level of human CLDN6 proteins in the breast cancer cell line MCF7 compared with normal tissues. The authors of Non-Patent Document 6 have cited therein the earlier literature Non-Patent Document 8 (Quan and Lu, Carcinogenesis 2003, 24: 1593) and stated that further study was performed based on the description of Non-Patent Document 8. This Non-Patent Document 8 discusses human CLDN6 serving as a tumor suppressor gene for breast cancer because the mRNA expression of human CLDN6 is decreased in breast cancer cell lines BT-474 and MCF7 compared with normal mammary gland epithelial cells. Specifically, in Non-Patent Document 6, the study has been conducted based on the idea that the expression of human CLDN6 proteins is decreased in the breast cancer cell line MCF7 compared with normal mammary glands, and this document has concluded that epigenetic silencing of human CLDN6 in the breast cancer cell line promotes anchorage-independent growth of the cancer cells.

Moreover, Non-Patent Document 7 is a document aimed only at examining, by immunohistochemical staining, change in the expression patterns of several mouse Claudin proteins including mouse CLDN6 proteins in the tumors of mice developed by DMBA/TPA administration-induced chemical carcinogenesis. This document has stated that mouse CLDN6 is expressed in "suprabasal compartment" even in normal mice.

Regarding anti-CLDN6 antibodies, a monoclonal antibody has not been reported yet which allows human CLDN6 on cell membrane surface, i.e., human CLDN6 present in a native form on cell membrane surface, to be recognized by a method such as flow cytometry.

[Patent Document 1] WO2003/088808
[Non-Patent Document 1] Mikio Furuse and Shoichiro Tsukita: Claudins in occluding junctions of human and flies. TRENDS in Cell Biology 2006, 16: 181
[Non-Patent Document 2] Edward R. Wilcox, Quianna L. Burton, Sadaf Naz, Saima Riazuddin, Tenesha N. Smith, Barbara Ploplis, Inna Belyantseva, Tamar Ben-Yosef, NikkiA. Liburd, Robert J. Morell, Bechara Kachar, Doris K. Wu, Andrew J. Griffith, Sheikh Riazuddin, and Thomas B. Friedman: Mutations in the Gene Encoding Tight Junction Claudin-14 Cause Autosomal Recessive Deafness DFNB29. Cell 2001, 104: 165
[Non-Patent Document 3] Christoph Rahner, Laura L. Mitic, and James M. Anderson: Heterogeneity in Expression and Subcellular Localization of Claudin 2, 3, 4, and 5 in the Rat Liver, Pancreas, and Gut. GASTROENTEROLOGY 2001, 120: 411
[Non-Patent Document 4] Kazumasa Morita, Mikio Furuse, Kazushi Fujimoto, and Shoichiro Tsukita: Claudin multigene family encoding four-transmembrane domain protein components of tight junction strands. Proc. Natl. Acad. Sci. USA 1999, 96: 511
[Non-Patent Document 5] Kyle J Hewitt, Rachana Agarwal and Patrice J Morin: The claudin gene family: expression in normal and neoplastic tissues. BMC Cancer 2006, 6: 186
[Non-Patent Document 6] Makoto Osanai, Masaki Murata, Hideki Chiba, Takashi Kojima and Norimasa Sawada: Epigenetic silencing of claudin-6 promotes anchorage-independent growth of breast carcinoma cells. Cancer Sci 2007, 98: 1557
[Non-Patent Document 7] Azadeh Arabzadeh, Tammy-Claire Troy and Kursad Turksen: Changes in the distribution pattern of Claudin tight junction proteins during the progression of mouse skin tumorigenesis. BMC Cancer 2007, 7: 196
[Non-Patent Document 8] Chengshi Quan and Shi-Jiang Lu: Identification of genes preferentially expressed in mammary epithelial cells of Copenhagen rat using subtractive hybridization and microarrays. Carcinogenesis 2003, 24: 1593
[Non-Patent Document 9] Kohls M D, Lappi D A: Mab-ZAP: A tool for evaluating antibody efficacy for use in an immunotoxin. BioTechniques 2000, 28 (1): 162
[Non-Patent Document 10] Nimmerjahn F, Ravetch J V.: Divergent immunoglobulin G subclass activity through selective Fc receptor binding. Science. 2005, 310: 1510
[Non-Patent Document 11] Nimmerjahn F, Ravetch J V.: Fcγ Receptors: Old friends and new family members. Immunity. 2006, 24: 19

DISCLOSURE OF THE INVENTION

Means for Solving the Problems

The present inventors found this time that human CLDN6 mRNA is overexpressed in tumor tissues (lung adenocarcinoma, gastric cancer, and ovarian cancer), although its expression is not observed in any adult normal tissue.

Moreover, the present inventors found that human CLDN6 proteins are highly expressed in a plurality of cancer cell lines, and the protein expression is consistent with the analysis results of its mRNA expression.

Furthermore, the present inventors successfully prepared a monoclonal antibody which recognizes human CLDN6 present in a native form on cell membrane surface, a monoclonal antibody which exhibits cytotoxicity through ADCC and/or CDC activities against cancer cell lines highly expressing human CLDN6, and a monoclonal antibody which has cell growth inhibitory effect through conjugation with toxin on cancer cell lines highly expressing human CLDN6.

Furthermore, the expression of human CLDN6 was not observed in normal tissues, demonstrating that human CLDN6 is exceedingly highly tumor-specific. Thus, the anti-CLDN6 antibody was expected to highly accumulate in tumors highly expressing human CLDN6 and found to serve as a very effective antitumor agent.

Specifically, the present invention provides an antibody binding to Claudin6 (CLDN6) expressed on a cell membrane. The present invention also provides an anti-CLDN6 antibody having cytotoxicity. Preferably, the anti-CLDN6 antibody of the present invention has ADCC and/or CDC activities. Moreover, in a preferable aspect, the anti-CLDN6 antibody of the present invention is conjugated with a cytotoxic substance.

In another aspect, the present invention provides an antibody described in any of the following (a) to (j):
(a) an antibody comprising a heavy chain variable region having CDR1 having the amino acid sequence represented by SEQ ID NO: 24, CDR2 having the amino acid sequence represented by SEQ ID NO: 25, and CDR3 having the amino acid sequence represented by SEQ ID NO: 26 (AB3-1 heavy chain);
(b) an antibody comprising a light chain variable region having CDR1 having the amino acid sequence represented by SEQ ID NO: 27, CDR2 having the amino acid sequence represented by SEQ ID NO: 28, and CDR3 having the amino acid sequence represented by SEQ ID NO: 29 (AB3-1 light chain);
(c) an antibody having the heavy chain variable region described in (a) and the light chain variable region described in (b) (AB3-1);
(d) an antibody comprising a heavy chain variable region having CDR1 having the amino acid sequence represented by SEQ ID NO: 30, CDR2 having the amino acid sequence represented by SEQ ID NO: 31, and CDR3 having the amino acid sequence represented by SEQ ID NO: 32 (AE1-16 or AE49-11 heavy chain);
(e) an antibody comprising a light chain variable region having CDR1 having the amino acid sequence represented by SEQ ID NO: 33, CDR2 having the amino acid sequence represented by SEQ ID NO: 34, and CDR3 having the amino acid sequence represented by SEQ ID NO: 35 (AE1-16 or AE49-11 light chain);
(f) an antibody having the heavy chain variable region described in (d) and the light chain variable region described in (e) (AE1-16 or AE49-11);
(g) an antibody comprising a heavy chain variable region having CDR1 having the amino acid sequence represented by SEQ ID NO: 40, CDR2 having the amino acid sequence represented by SEQ ID NO: 41, and CDR3 having the amino acid sequence represented by SEQ ID NO: 42 (AE3-20 heavy chain);
(h) an antibody comprising a light chain variable region having CDR1 having the amino acid sequence represented by SEQ ID NO: 43, CDR2 having the amino acid sequence represented by SEQ ID NO: 44, and CDR3 having the amino acid sequence represented by SEQ ID NO: 45 (AE3-20 light chain);
(i) an antibody having the heavy chain variable region described in (g) and the light chain variable region described in (h) (AE3-20); and
(j) an antibody which recognizes the same epitope as that recognized by the antibody described in any of (a) to (i).

In an alternative aspect, the present invention provides a pharmaceutical composition comprising an anti-CLDN6 antibody. Preferably, the pharmaceutical composition of the present invention is a cell growth inhibitor. Also preferably, the pharmaceutical composition of the present invention is an anticancer agent. Also preferably, the pharmaceutical composition of the present invention comprises the antibody of the present invention.

In a further alternative aspect, the present invention provides a method for diagnosing cancer. This method comprises the steps of:
(a) providing a sample collected from a subject; and
(b) detecting a CLDN6 protein contained in the sample collected in the step (a).
Preferably, the CLDN6 protein is detected using an anti-CLDN6 antibody.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
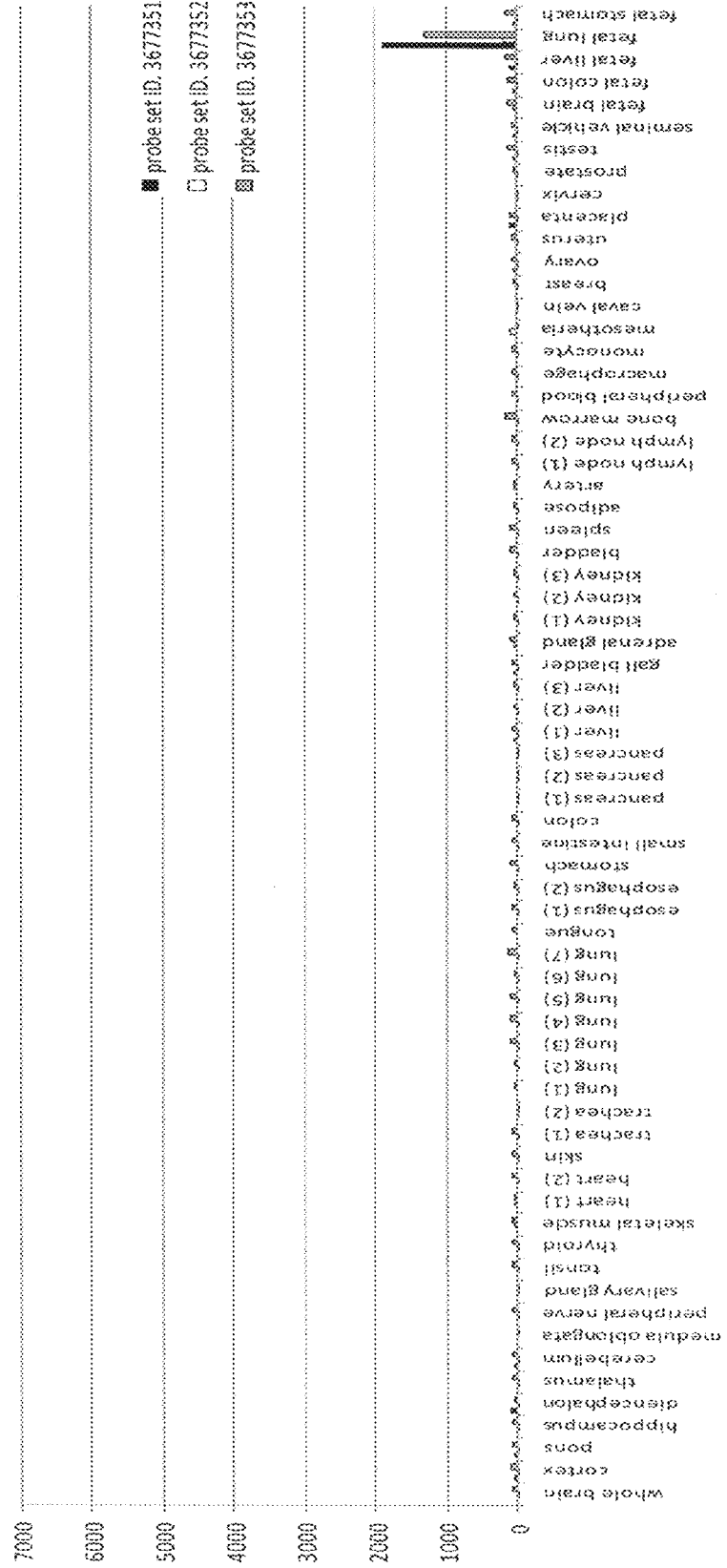
FIG. 1 shows the expression profile of human CLDN6 in normal tissues.

The present specification encompasses the contents described in the specification of Japanese Patent Application No. 2008-004423 that serves as a basis for the priority of the present application.

BEST MODE FOR CARRYING OUT THE INVENTION

CLDN6

The amino acid sequence of Claudin6 (CLDN6) and a gene sequence encoding this amino acid sequence are disclosed in GenBank Accession Nos. NP_067018.1 and NM_021195.3 (SEQ ID NOs: 22 and 23) or GenBank Accession Nos. NP_067018.2 and NM_021195.4 (SEQ ID NOs: 46 and 47).

In the present invention, the CLDN6 protein is meant to encompass both the full-length protein and a fragment thereof. The fragment is a polypeptide containing an arbitrary region of the CLDN6 protein and may not have the function of the natural CLDN6 protein. Examples of the fragment include fragments containing the extracellular region of the CLDN6 protein.

Anti-CLDN6 Antibody

An anti-CLDN6 antibody of the present invention may be any antibody as long as it binds to CLDN6. The anti-CLDN6 antibody of the present invention is not limited by its origin (mouse, rat, human, etc.), type (monoclonal or polyclonal antibody), and form (modified antibody, low-molecular-weight antibody, modified antibody, etc.), and so on.

It is preferred the anti-CLDN6 antibody used in the present invention should specifically bind to CLDN6. Moreover, the anti-CLDN6 antibody used in the present invention is preferably a monoclonal antibody.

Preferable examples of the anti-CLDN6 antibody according to the present invention can include an antibody capable of binding to CLDN6 expressed on a cell membrane. Examples of the CLDN6 expressed on a cell membrane include, but not particularly limited to, CLDN6 expressed on the membranes of cells (e.g., Ba/F3 cells) forced to express CLDN6 and cancer cells (e.g., lung adenocarcinoma cell line ABC-1 and gastric cancer cell line AGS) expressing CLDN6.

Whether or not the anti-CLDN6 antibody binds to CLDN6 expressed on a cell membrane can be confirmed by a method generally known by those skilled in the art, such as flow cytometry.

Another preferable aspect of the anti-CLDN6 antibody of the present invention can include an antibody having cytotoxicity. Examples of the antibody having cytotoxicity can include, but not particularly limited to, antibodies having antibody-dependent cell-mediated cytotoxicity (ADCC) activity, antibodies having complement-dependent cytotoxicity (CDC) activity, and antibodies conjugated with a cytotoxic substance.

In the present invention, the CDC activity means cytotoxicity mediated by the complement system. On the other hand, the ADCC activity means the activity of damaging target cells through the binding of Fcγ receptor-bearing cells (immunocytes, etc.) via the Fcγ receptors to the Fc domains of antibodies specifically attached to the cell surface antigens of the target cells.

In the present invention, whether or not the antibody has ADCC activity or has CDC activity can be determined by a method known in the art (e.g., Current protocols in Immunology, Chapter 7. Immunologic studies in humans, Editor, John E, Coligan et al., John Wiley & Sons, Inc., (1993)).

Specifically, effector cells, a complement solution, and target cells are first prepared.

(1) Preparation of Effector Cells

The spleens are excised from CBA/N mice or the like, and spleen cells are separated therefrom in an RPMI1640 medium (manufactured by Invitrogen Corp.). The cells can be washed with the same medium containing 10% fetal bovine serum (FBS, manufactured by HyClone Laboratories, Inc.) and then adjusted to a cell concentration of $5 \times 10^6$ cells/ml to prepare effector cells.

(2) Preparation of Complement Solution

Baby Rabbit Complement (manufactured by CEDARLANE Laboratories Ltd.) can be diluted 10-fold with a medium (manufactured by Invitrogen Corp.) containing 10% FBS to prepare a complement solution.

(3) Preparation of Target Cells

Cells expressing CLDN6 proteins can be cultured at 37° C. for 1 hour, together with 0.2 mCi $^{51}$Cr-sodium chromate (manufactured by GE Healthcare Bio-Sciences Corp.), in a DMEM medium containing 10% FBS to radiolabel the target cells. Cells transformed with CLDN6 protein-encoding genes, cancer cells (lung adenocarcinoma cells, gastric cancer cells, etc.), or the like can be used as the cells expressing CLDN6 proteins. After the radiolabeling, the cells can be washed three times with an RPMI1640 medium containing 10% FBS and adjusted to a cell concentration of $2 \times 10^5$ cells/ml to prepare the target cells.

The ADCC or CDC activity can be assayed by a method described below. For the ADCC activity assay, the target cells and the anti-CLDN6 antibody (50 μl each) are added to a U-bottom 96-well plate (manufactured by Becton, Dickinson and Company) and reacted for 15 minutes on ice. Then, 100 μl of the effector cells is added to the plate, and the cells are cultured for 4 hours in a $CO_2$ incubator. The final concentration of the antibody is set to 0 or 10 μg/ml. After the culture, 100 μl of the supernatant is collected, and the radioactivity is measured using a gamma counter (COBRAII AUTO-GAMMA, MODEL D5005, manufactured by Packard Instrument Company). The cytotoxicity (%) can be calculated based on the calculation formula (A−C)/(B−C)×100 using the obtained value. In the formula, A represents radioactivity (cpm) from each sample; B represents radioactivity (cpm) from a sample supplemented with 1% NP-40 (manufactured by Nacalai Tesque, Inc.); C represents radioactivity (cpm) from a sample containing only the target cells.

On the other hand, for the CDC activity assay, the target cells and the anti-CLDN6 antibody (50 μl each) are added to a flat-bottomed 96-well plate (manufactured by Becton, Dickinson and Company) and reacted for 15 minutes on ice. Then, 100 μl of the complement solution is added to the plate, and the cells are cultured for 4 hours in a $CO_2$ incubator. The final concentration of the antibody is set to 0 or 3 μg/ml. After the culture, 100 μl of the supernatant is collected, and the radioactivity is measured using a gamma counter. The cytotoxicity can be calculated in the same way as in the ADCC activity assay.

The anti-CLDN6 antibody conjugated with a cytotoxic substance, when incorporated in cells, is capable of inducing the death of the antibody-incorporated cells via the cytotoxic substance. Thus, it is preferred that the antibody conjugated with a cytotoxic substance should further have internalization activity. In the present invention, the "antibody having internalization activity" means an antibody that is transported into cells (cytoplasms, vesicles, other organelles, etc.) through its binding CLDN6 on the cell surface.

Whether or not the antibody has internalization activity can be confirmed by a method generally known by those skilled in the art and can be confirmed by, for example, a method comprising contacting labeling substance-bound anti-CLDN6 antibodies with CLDN6-expressing cells and confirming whether or not the labeling substances are incorporated into the cells, or a method comprising contacting cytotoxic substance-conjugated anti-CLDN6 antibodies with CLDN6-expressing cells and confirming whether or not the death of the CLDN6-expressing cells is induced. More specifically, whether or not the antibody has internalization activity can be confirmed by, for example, a method described in Examples below.

The cytotoxic substance used in the present invention may be any substance as long as it can induce the death of cells. Examples thereof can include toxin, radioactive substances, and chemotherapeutics. These cytotoxic substances according to the present invention encompass prodrugs that are converted to active cytotoxic substances in vivo. The activation of prodrugs may be enzymatic or nonenzymatic conversion.

In the present invention, the toxin means various microbe-, animal- or plant-derived proteins or polypeptides or the like that exhibit cytotoxicity. Examples of the toxin used in the present invention can include the followings: Diphtheria toxin A Chain (Langone J. J., et al., Methods in Enzymology, 93, 307-308, 1983), *Pseudomonas* Exotoxin (Nature Medicine, 2, 350-353, 1996), Ricin A Chain (Fulton R. J., et al., J. Biol. Chem., 261, 5314-5319, 1986; Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; Gheeite V., et al., J. Immunol. Methods, 142, 223-230, 1991); Deglicosylated Ricin A Chain (Thorpe P. E., et al., Cancer Res., 47, 5924-5931, 1987); Abrin A Chain (Wawrzynczak E. J., et al., Br. J. Cancer, 66, 361-366, 1992; Wawrzynczak E. J., et al., Cancer Res., 50, 7519-7562, 1990; Sivam G., et al., Cancer Res., 47, 3169-3173, 1987; Thorpe P. E., et al., Cancer Res., 47, 5924-5931, 1987); Gelonin (Sivam G., et al., Cancer Res., 47, 3169-3173, 1987; Cumber A. J. et al., J. Immunol. Methods, 135, 15-24, 1990; WawrzynczakE. J., et al., Cancer Res., 50, 7519-7562, 1990; Bolognesi A., et al., Clin. exp. Immunol., 89, 341-346, 1992); PAP-s; Pokeweed anti-viral protein from seeds (Bolognesi A., et al., Clin. exp. Immunol., 89, 341-346, 1992); Briodin (Bolognesi A., et al., Clin. exp. Immunol., 89, 341-346, 1992); Saporin (Bolognesi A., et al., Clin. exp. Immunol., 89, 341-346, 1992); Momordin (Cumber A. J., et al., J. Immunol. Methods, 135, 15-24, 1990; Wawrzynczak E. J., et al., Cancer Res., 50, 7519-7562, 1990; Bolognesi A., et al., Clin. exp. Immunol., 89, 341-346, 1992); Momorcochin (Bolognesi A., et al., Clin. exp. Immunol., 89, 341-346, 1992); Dianthin 32 (Bolognesi A., et al., Clin. exp. Immunol., 89, 341-346, 1992); Dianthin 30 (Stirpe F., Barbieri L., FEBS letter 195, 1-8, 1986); Modeccin (Stirpe F., Barbieri L., FEBS letter 195, 1-8, 1986); Viscumin (Stirpe F., Barbieri L., FEBS letter 195, 1-8, 1986); Volkesin (Stirpe F., Barbieri L., FEBS letter 195, 1-8, 1986); Dodecandrin (Stirpe F., Barbieri L., FEBS letter 195, 1-8, 1986); Tritin (Stirpe F., Barbieri L., FEBS letter 195, 1-8, 1986); Luffin (Stirpe F., Barbieri L., FEBS letter 195, 1-8, 1986); and Trichokirin (Casellas P., et al., Eur. J. Biochem. 176, 581-588, 1988; Bolognesi A., et al., Clin. exp. Immunol., 89, 341-346, 1992).

In the present invention, the radioactive substances refer to substances containing a radioisotope. Any radioisotope may be used without particular limitations as the radioisotope. For example, $^{32}P$, $^{14}C$, $^{125}I$, $^{3}H$, $^{131}I$, $^{186}Re$, or $^{188}Re$ can be used.

In the present invention, the chemotherapeutics mean substances having cytotoxicity except for the toxin and the radioactive substances and encompass cytokines, antitumor agents, enzymes, and the like. The chemotherapeutics used in the present invention are preferably, but not particularly limited to, low-molecular-weight chemotherapeutics. Such low-molecular-weight chemotherapeutics are less likely to interfere with antibody functions even after their binding with the antibody. In the present invention, the low-molecular-weight chemotherapeutics usually have a molecular weight of 100 to 2000, preferably 200 to 1000. Examples of the chemotherapeutics that can be used in the present invention include, but not particularly limited to, the followings: Melphalan (Rowland G. F., et al., Nature 255, 487-488, 1975); Cis-platinum (Hurwitz E. and Haimovich J., Method In Enzymology 178, 369-375, 1986; Schechter B., et al., Int. J. Cancer 48, 167-172, 1991; Carboplatin (Ota, Y., et al., Asia-Oceania J. Obstet. Gynaecol. 19, 449-457, 1993); Mitomycin C (Noguchi, A., et al., Bioconjugate Chem. 3, 132-137, 1992); Adriamycin (Doxorubicin)(Shih, L. B., et al., Cancer Res. 51 4192-4198, 1991; Zhu, Z., et al., Cancer Immunol. Immumother 40, 257-267, 1995; Trail, P. A., et al., Science 261, 212-215, 1993; Zhu, Z., et al., Cancer Immunol. Immumother 40, 257-267, 1995; Kondo, Y., et al., Jpn. J. Cancer Res. 86 1072-1079, 1995; Zhu, Z., et al., Cancer Immunol. Immumother 40, 257-267, 1995; Zhu, Z., et al., Cancer Immunol. Immumother 40, 257-267, 1995); Daunorubicin (Dillman, R. O., et al., Cancer Res. 48, 6097-6102, 1988; Hudecz, F., et al., Bioconjugate Chem. 1, 197-204, 1990; Tukada Y. et al., J. Natl. Cancer Inst. 75, 721-729, 1984); Bleomycin (Manabe, Y., et al., Biochem. Biophys. Res. Commun. 115, 1009-1014, 1983); Neocarzinostatin (Kitamura K., et al., Cancer Immunol. Immumother 36, 177-184, 1993; Yamaguchi T., et al., Jpn. J. Cancer Res. 85, 167-171, 1994); Methotrexate (Kralovec, J., et al., Cancer Immunol. Immumother 29, 293-302, 1989; Kulkarni, P. N., et al., Cancer Res. 41, 2700-2706, 1981; Shin, L. B., et al., Int. J. Cancer 41, 832-839, 1988; Gamett M. C., et al., Int. J. Cancer 31, 661-670, 1983); 5-Fluorouridine (Shin, L. B., Int. J. Cancer 46, 1101-1106, 1990); 5-Fluoro-2'-deoxyuridine (Goerlach A., et al., Bioconjugate Chem. 2, 96-101, 1991); Cytosine arabinoside (Hurwitz E., et al., J. Med. Chem. 28, 137-140, 1985); Aminopterin (Kanellos J., et al., Immunol. Cell. Biol. 65, 483-493, 1987); Vincristine (Johnson J. R., et al., Br. J. Cancer 42, 17, 1980); Vindesine. (Johnson J. R., et al., Br. J. Cancer 44, 472-475, 1981); Interleukin-2, Tumor necrosis factor-alpha, Interferon, Carboxypeptidase, Alkaline Phosphatase, β-lactamase, and Cytidine deaminase.

In the present invention, the cytotoxic substance used may be one type or a combination of two or more types of the cytotoxic substances.

The conjugation of the anti-CLDN6 antibody with the cytotoxic substance can be performed via a covalent or noncovalent bond or the like. A method for preparing the antibody conjugated with the cytotoxic substance is known in the art.

The anti-CLDN6 antibody and the cytotoxic substance may be conjugated directly via their own linking groups or the like or may be conjugated indirectly via an additional substance such as a linker or intermediate support. Examples of the linking groups for the direct conjugation of the anti-CLDN6 antibody with the cytotoxic substance include SH groups used in disulfide bond. Specifically, the intramolecular disulfide bond of the antibody Fc region is reduced using a reducing agent, for example, dithiothreitol, and the disulfide bond within the cytotoxic substance is reduced in the same way as above. Both the SH groups are linked via disulfide bond. Before the linking, either of the antibody or the cytotoxic substance may be activated using an activation promoter, for example, an Ellman's reagent, to promote the disulfide bond formation between them. Examples of other methods for directly conjugating the anti-CLDN6 antibody with the cytotoxic substance can include a method using Schiff bases, a carbodiimide method, an active ester method (N-hydroxysuccinimide method), a method using mixed anhydride, and a method using diazo reaction.

The anti-CLDN6 antibody and the cytotoxic substance may be conjugated indirectly via an additional substance. Examples of the additional substance for the indirect conjugation can include, but not particularly limited to: compounds having two or more groups of any one type or combined two or more types selected from an amino group, a carboxyl group, a mercapto group, and the like; peptide linkers; and compounds capable of binding to the anti-CLDN6 antibody. Examples of the compounds having two or more groups of any one type or combined two or more types selected from an amino group, a carboxyl group, a mercapto group, and the like can include SPDP: N-Succinimidyl 3-(2-pyridylditio) propinate (Wawrzynczak E. J., et al., Cancer Res., 50, 7519-7562, 1990; Thorpe P. E., et al., Cancer Res., 47, 5924-5931, 1987); LC-SPDP: Succinimidyl 6-3-[2-pyridylditio]propinamide)hexanoate (Hermanson G. T., BIOCONJUGATE Techniques, 230-232, 1996); Sulfo-LC-SPDP: Sulfosuccinimidyl 6-3-[2-pyridylditio]propinamide)hexanoate (Hermanson G. T., BIOCONJUGATE Techniques, 230-232, 1996); SPDB: N-Succinimidyl 3-(2-pyridylditio)butyrate (Wawrzynczak E. J., et al., Br. J. Cancer, 66, 361-366, 1992); SMPT: Succinimidyloxycarbonyl-α-(2-pyridylditio)toruene (Thorpe P. E., et al., Cancer Res., 47, 5924-5931, 1987); LC-SMPT: Succinimidyl 6-(α-methyl-[2-pyridylditio]toruamide)hexanoate (Hermanson G. T., BIOCONJUGATE Techniques, 232-235, 1996); Sulfo-LC-SMPT: Sulfosuccinimidyl 6-(α-methyl-[2-pyridylditio]toruamide)hexanoate (Hermanson G. T., BIOCONJUGATE Techniques, 232-235, 1996); SMPB: Succinimidyl-4-(p-maleimidophenyl)butyrate (Hermanson G. T., BIOCONJUGATE Techniques, 242-243, 1996); Sulfo-SMPB: Sulfo-Succinimidyl-4-(p-maleimidophenyl)butyrate (Hermanson G. T., BIOCONJUGATE Techniques, 242-243, 1996); MBS: m-Maleimidobenzoyl-N-hydroxysuccinimide ester (Hermanson G. T., BIOCONJUGATE Techniques, 237-238, 1996); Sulfo-MBS: m-Maleimidobenzoyl-N-hydroxysulfosuccinimide ester (Hermanson G. T., BIOCONJUGATE Techniques, 237-238, 1996); SAMSA: S-Acetyl mercaptosuccinic anhydride (Casellas P., et al., Eur. J. Biochem, 176, 581-588, 1988); DTBP: Dimethyl 3,3'-ditiobisprorionimidate (Casellas P., et al., Eur. J. Biochem, 176, 581-588, 1988); and 2-Iminotiolane (Thorpe P. E., et al., Cancer Res., 47, 5924-5931, 1987).

Examples of other substances used in the conjugation of the anti-CLDN6 antibody with the cytotoxic substance can include peptides, antibodies, poly-L-glutamic acid (PGA), carboxymethyldextran, dextran, aminodextran, avidin/biotin, cis-aconitic acid, glutamic acid dihydrazide, and human serum albumin (HSA).

Furthermore, a proteinous cytotoxic substance may be conjugated to the antibody by a genetic engineering approach. Specifically, for example, DNA encoding the cytotoxic peptide and DNA encoding the anti-CLDN6 antibody are fused in frame with each other, and this fused DNA can be incorporated into expression vectors to construct recombinant vectors. The vectors are introduced into appropriate host cells, and the resultant transformed cells are cultured. The incorporated DNA can be expressed by the cells to obtain toxic peptide-conjugated anti-CLDN6 antibodies as fusion proteins. For obtaining antibody-fusion proteins, the proteinous agent or toxin is generally located on the C-terminal side of the antibody. A peptide linker may be allowed to intervene between the antibody and the proteinous agent or toxin.

A preferable aspect of the anti-CLDN6 antibody of the present invention can include an antibody that binds to CLDN6 but does not substantially bind to CLDN9. The CLDN9 is highly homologous to CLDN6 and is thought to be a molecule most analogous to CLDN6. Thus, the antibody that binds to CLDN6 but does not substantially bind to CLDN9 is probably useful as a pharmaceutical drug with very high specificity to CLDN6. The amino acid sequence of CLDN9 is known in the art and, for example, the amino acid sequence of human CLDN9 is described in GenBank Accession No. NP_066192.1 (SEQ ID NO: 48).

In the present invention, the antibody that binds to CLDN6 but does not substantially bind to CLDN9 refers to an antibody having avidity for CLDN9 that is usually 50% or less, preferably 30% or less, more preferably 10% or less, compared with its avidity for CLDN6.

Also, a preferable aspect of the anti-CLDN6 antibody of the present invention can include an antibody that binds to CLDN6 but does not substantially bind to CLDN3. The amino acid sequence of CLDN3 is known in the art and, for example, the amino acid sequence of human CLDN3 is described in GenBank Accession No. NP_001297.1 (SEQ ID NO: 49). In the present invention, the antibody that binds to CLDN6 but does not substantially bind to CLDN3 refers to an antibody having avidity for CLDN3 that is usually 50% or less, preferably 30% or less, more preferably 10% or less, compared with its avidity for CLDN6.

Also, a preferable aspect of the anti-CLDN6 antibody of the present invention can include an antibody that binds to CLDN6 but does not substantially bind to CLDN4. The amino acid sequence of CLDN4 is known in the art and, for example, the amino acid sequence of human CLDN4 is described in GenBank Accession No. NP_001296.1 (SEQ ID NO: 50). In the present invention, the antibody that binds to CLDN6 but does not substantially bind to CLDN4 refers to an antibody having avidity for CLDN4 that is usually 50% or less, preferably 30% or less, more preferably 10% or less, compared with its avidity for CLDN6.

Also, a preferable aspect of the anti-CLDN6 antibody of the present invention can include an antibody that binds to CLDN6 but does not substantially bind to CLDN1. The amino acid sequence of CLDN1 is known in the art and, for example, the amino acid sequence of human CLDN1 is described in GenBank Accession No. NP_066924.1 (SEQ ID NO: 51). In the present invention, the antibody that binds to CLDN6 but does not substantially bind to CLDN1 refers to an antibody having avidity for CLDN1 that is usually 50% or less, preferably 30% or less, more preferably 10% or less, compared with its avidity for CLDN6.

In the present invention, preferable examples of the anti-CLDN6 antibody can include an antibody that binds to human CLDN6 but does not substantially bind to human CLDN1 or human CLDN3, an antibody that binds to human CLDN6 but does not substantially bind to human CLDN1, human CLDN3, or human CLDN4, and an antibody that binds to human CLDN6 but does not substantially bind to human CLDN1, human CLDN3, human CLDN4, or human CLDN9.

Preferable examples of the anti-CLDN6 antibody of the present invention can include an antibody described in any of the following (a) to (j):

(a) an antibody comprising a heavy chain variable region having CDR1 having the amino acid sequence represented by SEQ ID NO: 24, CDR2 having the amino acid sequence represented by SEQ ID NO: 25, and CDR3 having the amino acid sequence represented by SEQ ID NO: 26 (AB3-1 heavy chain);

(b) an antibody comprising a light chain variable region having CDR1 having the amino acid sequence represented by SEQ ID NO: 27, CDR2 having the amino acid sequence represented by SEQ ID NO: 28, and CDR3 having the amino acid sequence represented by SEQ ID NO: 29 (AB3-1 light chain);

(c) an antibody having the heavy chain variable region described in (a) and the light chain variable region described in (b) (AB3-1);

(d) an antibody comprising a heavy chain variable region having CDR1 having the amino acid sequence represented by SEQ ID NO: 30, CDR2 having the amino acid sequence represented by SEQ ID NO: 31, and CDR3 having the amino acid sequence represented by SEQ ID NO: 32 (AE1-16 or AE49-11 heavy chain);

(e) an antibody comprising a light chain variable region having CDR1 having the amino acid sequence represented by SEQ ID NO: 33, CDR2 having the amino acid sequence represented by SEQ ID NO: 34, and CDR3 having the amino acid sequence represented by SEQ ID NO: 35 (AE1-16 or AE49-11 light chain);

(f) an antibody having the heavy chain variable region described in (d) and the light chain variable region described in (e) (AE1-16 or AE49-11);

(g) an antibody comprising a heavy chain variable region having CDR1 having the amino acid sequence represented by SEQ ID NO: 40, CDR2 having the amino acid sequence represented by SEQ ID NO: 41, and CDR3 having the amino acid sequence represented by SEQ ID NO: 42 (AE3-20 heavy chain);

(h) an antibody comprising a light chain variable region having CDR1 having the amino acid sequence represented by SEQ ID NO: 43, CDR2 having the amino acid sequence represented by SEQ ID NO: 44, and CDR3 having the amino acid sequence represented by SEQ ID NO: 45 (AE3-20 light chain);

(i) an antibody having the heavy chain variable region described in (g) and the light chain variable region described in (h) (AE3-20); and (j) an antibody which recognizes the same epitope as that recognized by the antibody described in any of (a) to (i).

Whether an antibody to be tested recognizes the same epitope as that recognized by a certain antibody, i.e., these antibodies share the epitope, can be confirmed based on their competition for the same epitope. The competition between the antibodies is detected by cross-blocking assay or the like. For example, competitive ELISA assay is preferable cross-blocking assay. Specifically, in the cross-blocking assay, CLDN6 proteins coated on the wells of a microtiter plate are preincubated in the presence or absence of a candidate competing antibody, and the anti-CLDN6 antibody of the present invention is then added to the wells. The amount of the anti-CLDN6 antibody of the present invention bound to the CLDN6 protein in the well indirectly correlates with the binding ability of the candidate competing antibody (antibody to be tested) that competes therewith for the binding to the same epitope. Specifically, the larger affinity the antibody to be tested has for the same epitope, the smaller amount of the anti-CLDN6 antibody of the present invention is bound to the CLDN6 protein-coated well while the larger amount of the antibody to be tested is bound to the CLDN6 protein-coated well.

The amount of the antibody bound to the well can be measured easily by labeling the antibody in advance. For example, a biotin-labeled antibody can be measured by use of an avidin-peroxidase conjugate and an appropriate substrate. The cross-blocking assay using enzyme (e.g., peroxidase) labeling is particularly referred to as competitive ELISA assay. The antibody can be labeled with other detectable or measurable labeling substances. Specifically, radiolabeling or fluorescent labeling or the like is known in the art.

Furthermore, when the antibody to be tested has constant regions derived from a species different from that of the anti-CLDN6 antibody of the present invention, the amount of each antibody bound to the well may be measured using a labeled antibody that recognizes the constant regions of this antibody. Alternatively, even antibodies derived from the same species, when differing in class, can be measured for their respective amounts bound to the well using antibodies that discriminate each class.

This candidate competing antibody is determined to be an antibody that binds to substantially the same epitope as that bound by the anti-CLDN6 antibody of the present invention or competes therewith for the binding to the same epitope, provided that the candidate antibody can block the binding of the anti-CLDN6 antibody by at least 20%, preferably at least 30%, more preferably at least 50%, compared with the avidity obtained in the control test performed in the absence of the candidate competing antibody.

Furthermore, the antibodies (a) to (j) according to the present invention may have substitution, deletion, addition, and/or insertion of one or more amino acids in their CDR sequences as long as the resulting antibodies are functionally equivalent to the antibodies (a) to (j). In the present invention, the term "functionally equivalent" refers to being comparable in avidity for CLDN6 and cytotoxicity. In the present invention, the term "equivalent" refers to having at least 50%, preferably 70%, more preferably 90% or higher activity, compared with the antibodies (a) to (j). The upper limit of the activity is not particularly limited and may be higher than that of the antibodies (a) to (j). The avidity or cytotoxicity can be assayed by a method generally known by those skilled in the art and can be assayed by, for example, a method described in Examples.

Examples of methods well known by those skilled in the art for the substitution, deletion, addition, and/or insertion of amino acids can include site-directed mutagenesis (Hashimoto-Gotoh, T. et al. (1995) Gene 152, 271-275, Zoller, M J, and Smith, M. (1983) Methods Enzymol. 100, 468-500, Kramer, W. et al. (1984) Nucleic Acids Res. 12, 9441-9456, Kramer W, and Fritz H J (1987) Methods. Enzymol. 154, 350-367, Kunkel, T A (1985) Proc Natl Acad Sci USA. 82, 488-492, Kunkel (1988) Methods Enzymol. 85, 2763-2766). Moreover, amino acid variation can occur in the nature. Thus, the antibody of the present invention also encompasses antibodies that have an amino acid sequence derived from that of the antibody of the present invention by the modification of one or more amino acids and have activity equivalent to that of the antibody. In such modifications, the number of amino acids modified can be usually within 5 amino acids, preferably within 4 amino acids, more preferably within 3 amino acids (e.g., 1 or 2 amino acids), per CDR.

The modified amino acid residue(s) are not particularly limited, and it is preferred that such amino acid modification should be performed conservatively between amino acids having the same side chain property. For example, the following classification has been established based on the properties of amino acid side chains:

hydrophobic amino acids (A, I, L, M, F, P, W, Y, and V),
hydrophilic amino acids (R, D, N, C, E, Q, G, H, K, S, and T),
amino acids having an aliphatic side chain (G, A, V, L, I, and P),
amino acids having a side chain containing a hydroxyl group (S, T, and Y),
amino acids having a side chain containing a sulfur atom (C and M),
amino acids having a side chain containing carboxylic acid and amide (D, N, E, Q),
amino acids having a side chain containing a base (R, K, and H), and
amino acids having an aromatic side chain (H, F, Y, and W). (each alphabet in the parentheses represents the single character code of the amino acid.)

It has already been known that a polypeptide having an amino acid sequence modified from a certain amino acid sequence by deletion and/or addition of one or more amino acid residues and/or substitution with other amino acids maintains its biological activity (Mark, D. F. et al., Proc. Natl. Acad. Sci. USA (1984) 81, 5662-5666, Zoller, M. J. and Smith, M., Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413). Specifically, in general, a certain polypeptide is allegedly highly likely to maintain its activity when an amino acid sequence constituting the polypeptide is substituted by another amino acid classified in the same group thereas.

Method for Producing Antibody

The anti-CLDN6 antibody of the present invention can be obtained using means known in the art. The anti-CLDN6 antibody of the present invention is particularly preferably a mammal-derived monoclonal antibody. The mammal-derived monoclonal antibody encompasses, for example, those produced from hybridomas and those produced by hosts transformed with antibody gene-containing expression vectors through a genetic engineering approach.

The monoclonal antibody-producing hybridomas can be prepared using a technique known in the art, for example, as follows: first, animals are immunized with CLDN6 proteins, CLDN6-expressing cells, or CLDN6-encoding genes as sensitizing antigens according to a usual immunization method. Immunocytes obtained from the immunized animals are fused with parental cells known in the art by a usual cell fusion method to obtain hybridomas. From these hybridomas, cells producing the antibody of interest can further be screened by a usual screening method to select the hybridomas producing the anti-CLDN6 antibody.

Specifically, the monoclonal antibody is prepared, for example, as shown below. First, CLDN6 genes can be expressed to obtain CLDN6 proteins used as sensitizing antigens for antibody obtainment. The nucleotide sequence of the human CLDN6 gene used can be obtained from a sequence disclosed in, for example, GenBank Accession No. NM_021195.3 (SEQ ID NO: 23) or NM_021195.4 (SEQ ID NO: 47). Specifically, the CLDN6-encoding gene sequence is inserted into expression vectors known in the art, with which appropriate host cells are then transformed. Then, the human CLDN6 proteins of interest can be purified from the host cells or a culture supernatant thereof by a method known in the art. Moreover, purified natural CLDN6 proteins may be used similarly. The purification can be performed by using a plurality of usual chromatography techniques such as ion chromatography and affinity chromatography alone or in combination at single or a plurality of runs. Moreover, the desired partial polypeptide of the CLDN6 protein is fused with a different polypeptide to prepare a fusion protein, which can in turn be used as an immunogen. For example, antibody Fc fragments, peptide tags, and so on can be used for producing the fusion protein used as an immunogen. Vectors for expression of the fusion protein can be prepared by fusing, in frame, two or more genes respectively encoding the desired polypeptide fragments and inserting this fusion gene into expression vectors in the same way as above. The method for preparing the fusion protein is described in Molecular Cloning 2nd ed. (Sambrook, J. et al., Molecular Cloning $2^{nd}$ ed., 9.47-9.58, Cold Spring Harbor Lab. Press, 1989).

The CLDN6 proteins thus purified can be used as sensitizing antigens used for the immunization of mammals. Partial peptides of CLDN6 can also be used as sensitizing antigens.

The mammals immunized with the sensitizing antigens are not particularly limited. For obtaining the monoclonal antibody by the cell fusion method, it is preferred that the immunized animals should be selected in consideration of compatibility with the parental cells used in cell fusion. In general, rodents are preferable as the immunized animals. Specifically, mice, rats, hamsters, or rabbits can be used as the immunized animals. In addition, monkeys or the like may be used as the immunized animals.

These animals can be immunized with the sensitizing antigens according to a method known in the art. For example, a general method can involve immunizing the mammals with the sensitizing antigens by intraperitoneal or subcutaneous injection. Specifically, the sensitizing antigens are administered to the mammals several times at 4- to 21-day intervals. The sensitizing antigens are diluted with PBS (Phosphate-Buffered Saline), saline, or the like at an appropriate dilution ratio and used in the immunization. Furthermore, the sensitizing antigens can be administered together with an adjuvant. For example, the antigens can be mixed with a Freund's complete adjuvant for emulsification to prepare sensitizing antigens. Moreover, an appropriate carrier can be used in the immunization with the sensitizing antigens. Particularly, when partial peptides having a small molecular weight are used as the sensitizing antigens, it is preferred that the sensitizing antigen peptides should be bound to carrier proteins such as albumin or keyhole limpet hemocyanin and used in the immunization.

Increase in the amount of the desired antibody in the serum of the mammals thus immunized is confirmed. Then, immunocytes are collected from the mammals and subjected to cell fusion. Particularly, spleen cells can be used as preferable immunocytes.

Mammalian myeloma cells are used as cells fused with the immunocytes. It is preferred that the myeloma cells should have an appropriate selection marker for screening. The selection marker refers to a character that can survive (or cannot survive) under particular culture conditions. For example, hypoxanthine-guanine phosphoribosyltransferase deficiency (hereinafter, abbreviated to HGPRT deficiency) or thymidine kinase deficiency (hereinafter, abbreviated to TK deficiency) is known in the art as the selection marker. Cells having the HGPRT or TK deficiency is sensitive to hypoxanthine-aminopterin-thymidine (hereinafter, abbreviated to HAT-sensitive). The HAT-sensitive cells are killed in a HAT selective medium because they cannot synthesize DNA. By contrast, these cells, when fused with normal cells, can grow even in the HAT selective medium because they can continue DNA synthesis by use of the salvage pathway of the normal cells.

The cells having the HGPRT or TK deficiency can be selected in a medium containing 6-thioguanine or 8-azaguanine (hereinafter, abbreviated to 8AG) for the HGPRT deficiency or 5'-bromodeoxyuridine for the TK deficiency. The normal cells are killed in such a medium because they incorporate these pyrimidine analogs into their DNAs. By contrast, the cells deficient in these enzymes can survive in the selective medium because they cannot incorporate the pyrimidine analogs therein. In addition, a selection marker called G418 resistance imparts, to cells, 2-deoxystreptamine antibiotic (gentamicin analog) resistance via a neomycin resistance gene. Various myeloma cells suitable for the cell fusion are known in the art. For example, myeloma cells can be used, such as P3 (P3x63Ag8. 653) (J. Immunol. (1979) 123, 1548-1550), P3x63Ag8U. 1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), F0 (de St. Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133).

The cell fusion of the immunocytes with the myeloma cells can be performed according to a method known in the art, for example, the method of Kohler and Milstein et al. (Kohler. G. and Milstein, C., Methods Enzymol. (1981) 73, 3-46).

More specifically, the cell fusion can be performed, for example, in a usual nutrient culture solution in the presence of a cell fusion promoter. For example, polyethylene glycol (PEG) or hemagglutinating virus of Japan (HVJ) can be used as the fusion promoter. Furthermore, an auxiliary such as dimethyl sulfoxide can also be added thereto, if desired, for enhancing fusion efficiency.

The ratio between the immunocytes and the myeloma cells used can be set arbitrarily. For example, it is preferred that the amount of the immunocytes should be set to 1 to 10 times that of the myeloma cells. For example, RPMI1640 or MEM culture solutions suitable for the growth of the myeloma cell line as well as usual culture solutions used in this kind of cell culture can be used as the culture solution used in the cell fusion. Furthermore, a solution supplemented with serum (e.g., fetal calf serum (FCS)) can be added to the culture solution.

For the cell fusion, the immunocytes and the myeloma cells are well mixed in the predetermined amounts in the culture solution, and the mixture is mixed with a PEG solution preheated to approximately 37° C. to form the fusion cells (hybridomas) of interest. In the cell fusion method, for example, PEG with an average molecular weight on the order of 1000 to 6000 can usually be added at a concentration of 30 to 60% (w/v). Subsequently, the appropriate culture solution exemplified above is added to the hybridomas, and the mixture is centrifuged, followed by removal of the supernatant. This procedure is repeated to remove the cell fusion agents or the like unfavorable for hybridoma growth.

The hybridomas thus obtained can be selected by use of a selective culture solution appropriate for the selection marker of the myeloma cells used in the cell fusion. For example, the cells having the HGPRT or TK deficiency can be selected by culturing the hybridomas in a HAT culture solution (culture solution containing hypoxanthine, aminopterin, and thymidine). Specifically, when HAT-sensitive myeloma cells are used in the cell fusion, only cells successfully fused with normal cells can be grown selectively in the HAT culture solution. The culture using the HAT culture solution is continued for a time long enough to kill cells (non-fused cells) other than the hybridomas of interest. Specifically, the culture can generally be performed for a few days to a few weeks to select the hybridomas of interest. Subsequently, hybridomas producing the antibody of interest can be screened and cloned as single clones by a usual limiting dilution method. Alternatively, the antibody recognizing CLDN6 may be prepared according to a method described in International Publication No. WO 03/104453.

The screening of the antibody of interest and cloning as single clones thereof can be performed preferably by a screening method based on antigen-antibody reaction known in the art. For example, the antigens are bound to a carrier such as beads made of polystyrene or the like or a commercially available 96-well microtiter plate and reacted with the culture supernatant of the hybridomas. Subsequently, the carrier is washed and then reacted with enzyme-labeled secondary antibodies or the like. If the culture supernatant contains the antibody of interest reactive with the sensitizing antigens, the secondary antibodies bind to the carrier via this antibody. Finally, the secondary antibodies bound with the carrier can be detected to determine the presence of the antibody of interest in the culture supernatant. The hybridomas producing the desired antibody capable of binding to the antigen can be cloned by a limiting dilution method or the like. In this screening, the CLDN6 proteins used in the immunization or CLDN6 proteins substantially identical thereto can be used preferably as the antigens. For example, oligopeptides comprising the CLDN6 extracellular domain or a partial amino acid sequence constituting this region can be used as the antigens.

Moreover, in addition to the method for obtaining the hybridomas by immunizing the non-human animals with the antigens, human lymphocytes may be sensitized with the antigens to obtain the antibody of interest. Specifically, the human lymphocytes are first sensitized with the CLDN6 proteins in vitro. Subsequently, the sensitized lymphocytes are fused with appropriate fusion partners. For example, human-derived myeloma cells capable of dividing throughout their lives can be used as the fusion partners (see Japanese Patent Publication No. Hei1-59878). Anti-CLDN6 antibodies obtained by this method are human antibodies having avidity for the CLDN6 proteins.

Furthermore, the CLDN6 proteins can also be administered as antigens to transgenic animals having all repertoires of human antibody genes to obtain anti-CLDN6 human antibodies. Antibody-producing cells from the immunized animals can be immortalized by treatment such as cell fusion with appropriate fusion partners or infection with Epstein-Barr virus. From the immortalized cells thus obtained, human antibodies against the CLDN6 proteins can be isolated (see International Publication Nos. WO 94/25585, WO 93/12227, WO 92/03918, and WO 94/02602). Furthermore, the immortalized cells may be cloned to clone cells producing antibodies having the reaction specificity of interest. When transgenic animals are used as the immunized animals, the immune systems of the animals recognize human CLDN6 as foreign substances. Thus, the human antibodies against human CLDN6 can be obtained easily. The monoclonal antibody-producing hybridomas thus prepared can be subcultured in a usual culture solution. Moreover, the hybridomas can also be stored over a long period in liquid nitrogen.

Also, a technique for obtaining human antibodies by panning using human antibody libraries is known. For example, human antibody V regions are expressed as single chain antibodies (scFvs) on phage surface by a phage display method, and phages binding to the antigen can be selected. The selected phages can be subjected to gene analysis to determine DNA sequences encoding the human antibody V regions binding to the antigen. The thus-determined DNA sequences of the scFvs (V regions) binding to the antigen are then fused in frame with the sequences of the desired human antibody C regions, and the fusion products can then be inserted into appropriate expression vectors to prepare expression vectors. The expression vectors are incorporated into the preferable expression cells exemplified above, which can then be caused to express the human antibody-encoding genes to obtain human antibodies. These methods are already known in the art (International Publication Nos. WO 92/01047, WO 92/20791, WO 93/06213, WO 93/11236, WO 93/19172, WO 95/01438, and WO 95/15388).

The hybridomas are cultured according to a usual method, and the monoclonal antibody of interest can be obtained from the culture supernatant thereof. Alternatively, the hybridomas are administered to mammals compatible therewith and grown, and the monoclonal antibody can be obtained from their ascitic fluids. The former method is suitable for obtaining highly pure antibodies.

Recombinant Antibody

The antibody of the present invention may be a recombinant antibody that can be prepared using antibody genes cloned from antibody-producing cells. The cloned antibody genes are incorporated into appropriate vectors, with which hosts can then be transformed and caused to express antibodies. Methods for the antibody gene isolation, the introduction into vectors, and the transformation of host cells have already been established (see e.g., Vandamme, A. M. et al., Eur. J. Biochem. (1990) 192, 767-775).

For example, cDNAs encoding the variable regions (V regions) of the anti-CLDN6 antibody can be obtained from anti-CLDN6 antibody-producing hybridoma cells. For this purpose, usually, total RNAs are first extracted from the hybridomas. For example, a guanidine ultracentrifugation method (Chirgwin, J. M. et al., Biochemistry (1979) 18, 5294-5299) or an AGPC method (Chomczynski, P. et al., Anal. Biochem. (1987) 162, 156-159) can be used as a method for mRNA extraction from the cells.

The extracted mRNAs can be purified using mRNA Purification Kit (manufactured by GE Healthcare Bio-Sciences Corp.) or the like. Alternatively, a kit for directly extracting total mRNAs from cells is also commercially available, such as QuickPrep mRNA Purification Kit (manufactured by GE Healthcare Bio-Sciences Corp.). Total mRNAs may be obtained from the hybridomas using such a kit. From the obtained mRNAs, antibody V region-encoding cDNAs can be synthesized using reverse transcriptase. The cDNAs can be synthesized using AMV Reverse Transcriptase First-strand cDNA Synthesis Kit (manufactured by SEIKAGAKU CORP.) or the like. Moreover, 5'-Ampli FINDER RACE Kit (manufactured by Clontech Laboratories, Inc.) and 5'-RACE PCR (Frohman, M. A. et al., Proc. Natl. Acad. Sci. USA (1988) 85, 8998-9002; and Belyaysky, A. et al., Nucleic Acids Res. (1989) 17, 2919-2932) can be used for the cDNA synthesis and amplification. Furthermore, appropriate restriction sites described later can be introduced into both ends of the cDNAs in the course of such cDNA synthesis.

From the obtained PCR products, the cDNA fragments of interest are purified and subsequently ligated with vector DNAs. The recombinant vectors thus prepared are introduced into E. coli or the like. After colony selection, the desired recombinant vectors can be prepared from E. coli that has formed the colony. Then, whether or not the recombinant vectors have the nucleotide sequence of the cDNA of interest can be confirmed by a method known in the art, for example, a dideoxynucleotide chain termination method.

PCR using primers for variable region gene amplification may be used for obtaining the variable region-encoding genes. First, cDNAs are synthesized with the extracted mRNAs as templates to obtain cDNA libraries. A commercially available kit is conveniently used in the cDNA library synthesis. In actuality, mRNAs from only a small number of cells are obtained in very small amounts. Therefore, direct purification thereof gives low yields. Thus, carrier RNAs shown to be free from antibody genes are usually added thereto, followed by purification. Alternatively, when RNAs can be extracted in given amounts, efficient extraction can be achieved only using those from the antibody-producing cells. The addition of the carrier RNAs may be unnecessary for RNA extraction from, for example, 10 or more or 30 or more, preferably 50 or more antibody-producing cells.

The antibody genes are amplified by PCR with the obtained cDNA libraries as templates. Primers for the PCR amplification of the antibody genes are known in the art. For example, primers for human antibody gene amplification can be designed based on the disclosure of the paper (J. Mol. Biol. (1991) 222, 581-597) or the like. These primers have a nucleotide sequence differing on an immunoglobulin subclass basis. Thus, when cDNA libraries whose subclass is unknown are used as templates, PCR is performed in consideration of every possibility.

Specifically, for example, for the purpose of obtaining human IgG-encoding genes, primers can be used, which are capable of amplifying genes encoding γ1 to γ5 heavy chains and κ and λ light chains. For amplifying IgG variable region genes, 3' primers are generally used, which anneal to a portion corresponding to the hinge region. On the other hand, primers appropriate for each subclass can be used as 5' primers.

The PCR products obtained from the gene amplification primers appropriate for these heavy and light chain subclasses are prepared as their respective independent libraries. The libraries thus synthesized can be used to reshape immunoglobulins comprising the heavy and light chains in combination. The antibody of interest can be screened with the avidity of the reshaped immunoglobulins for CLDN6 as an indicator.

A panning method using phage vectors may be used in the antibody screening with the avidity as an indicator. The screening method using phage vectors is advantageous when the antibody genes are obtained as libraries of heavy and light chain subclasses as described above. Heavy chain variable region- and light chain variable region-encoding genes can be linked through an appropriate linker sequence to prepare single chain Fv (scFv)-encoding genes. The scFv-encoding genes can be inserted into phage vectors to obtain phages expressing scFv on the surface. DNAs encoding scFvs having the avidity of interest can be collected by contacting these phages with the antigens of interest and collecting the antigen-bound phages. This procedure can be repeated, if desired, to concentrate the scFvs having the avidity of interest.

The cDNAs encoding the V regions of the anti-CLDN6 antibody of interest are thus obtained and then digested with restriction enzymes that recognize the restriction sites inserted in both ends of the cDNAs. Preferable restriction enzymes recognize and digest nucleotide sequences that appear with low possibility in the nucleotide sequences constituting the antibody genes. Furthermore, restriction enzymes that offer a sticky end are preferable for inserting one copy of the digested fragment in the correct orientation into a vector. The anti-CLDN6 antibody V region-encoding cDNAs thus digested can be inserted into appropriate expression vectors to obtain antibody expression vectors. In this case, antibody constant region (C region)-encoding genes can be fused in frame with the V region-encoding genes to obtain whole antibodies.

For producing the anti-CLDN6 antibody of the present invention, the antibody genes can be incorporated in the expression vectors such that they are expressed under the control of expression control regions. The expression control regions for antibody expression encompass, for example, enhancers and promoters. Subsequently, appropriate host cells can be transfected with the expression vectors to obtain recombinant cells expressing the anti-CLDN6 antibody-encoding DNA.

For the antibody gene expression, the antibody heavy chain (H chain)- and light chain (L chain)-encoding DNAs can be incorporated separately in different expression vectors. The same host cell can be co-transfected with the H chain- and L chain-incorporated vectors and thereby caused to express antibody molecules comprising H and L chains. Alternatively, the H chain- and L chain-encoding DNAs may be incorporated in single expression vectors, with which host cells are transfected (see International Publication No. WO 94/11523).

The hosts and the expression vectors for temporarily isolating the antibody genes and introducing them into appropriate hosts for antibody preparation are known in the art as many combinations. All of these expression systems can be applied to the present invention. When eukaryotic cells are used as the hosts, animal, plant, or fungus cells can be used. Specifically, examples of the animal cells that can be used in the present invention include mammalian cells (e.g., CHO, COS, myeloma, BHK (baby hamster kidney), Hela, and Vero cells), amphibian cells (e.g., *Xenopus* oocytes), and insect cells (e.g., sf9, sf21, and Tn5 cells).

Alternatively, for the plant cells, antibody gene expression systems are known in the art, which involve cells derived from the genus *Nicotiana* (e.g., *Nicotiana tabacum*). Cultured callus cells can be used in the plant cell transformation.

Furthermore, cells derived from the genus *Saccharomyces* (e.g., *Saccharomyces cerevisiae*), the genus *Pichia* (e.g., *Pichia pastoris*), the genus *Aspergillus* (e.g., *Aspergillus niger*), or the like can be used as the fungus cells.

Alternatively, antibody gene expression systems using prokaryotic cells are also known in the art. For example, when bacterial cells are used, bacterial cells derived from *E. coli*, *Bacillus subtilis*, or the like can be used in the present invention.

When the mammalian cells are used, expression vectors can be constructed, which comprise a useful promoter routinely used, the antibody gene to be expressed, and a poly A signal located 3'-downstream thereof, which are functionally ligated. Examples of the promoter/enhancer can include a human cytomegalovirus immediate early promoter/enhancer.

Moreover, other examples of the promoter/enhancer that can be used in the expression of the antibody of the present invention include virus promoters/enhancers and mammalian cell-derived promoters/enhancers (e.g., human elongation factor 1α (HEF1α)). Examples of the viruses whose promoter/enhancer can be used can specifically include retrovirus, polyomavirus, adenovirus, and simian virus 40 (SV40).

The SV40 promoter/enhancer can be used according to the method of Mulligan et al. (Nature (1979) 277, 108). Moreover, the HEF1α promoter/enhancer can be used easily in the gene expression of interest by the method of Mizushima et al. (Nucleic Acids Res. (1990) 18, 5322).

For the *E. coli*, a useful promoter routinely used, a signal sequence for antibody secretion, and the antibody gene to be expressed can be ligated functionally for the gene expression. Examples of the promoter can include lacZ and araB promoters. The lacZ promoter can be used according to the method of Ward et al. (Nature (1989) 341, 544-546; and FASEBJ. (1992) 6, 2422-2427). Alternatively, the araB promoter can be used in the gene expression of interest by the method of Better et al. (Science (1988) 240, 1041-1043).

When antibodies are produced in *E. coli* periplasm, a pelB signal sequence (Lei, S. P. et al., J. Bacteriol. (1987) 169, 4379) may be used as the signal sequence for antibody secretion. Then, the antibodies produced in the periplasm are separated and then refolded by use of protein denaturants such as urea and guanidine hydrochloride such that they have the desired avidity.

A replication origin derived from SV40, polyomavirus, adenovirus, bovine papillomavirus (BPV), or the like can be used as a replication origin inserted in the expression vectors. Furthermore, a selection marker can be inserted in the expression vectors for increasing a gene copy number in the host cell systems. Specifically, selection markers can be used, such as aminoglycoside phosphotransferase (APH), thymidine kinase (TK), *E. coli* xanthine-guanine phosphoribosyltransferase (Ecogpt), and dihydrofolate reductase (dhfr) genes.

The host cells are transformed with these expression vectors, and the transformed host cells are cultured in vitro or in vivo to produce the antibody of interest. The culture of the host cells is performed according to a method known in the art. For example, a DMEM, MEM, RPMI1640, or IMDM culture solution can be used and may be used in combination with a solution supplemented with serum such as fetal calf serum (FCS).

The antibodies thus expressed and produced can be purified by using, alone or in appropriate combination, usual protein purification methods known in the art. For example, affinity or chromatography columns (e.g., protein A columns), filters, ultrafiltration, salting-out, and dialysis can be selected and combined appropriately to separate and purify the antibodies (Antibodies A Laboratory Manual. Ed Harlow, David Lane, Cold Spring Harbor Laboratory, 1988).

Moreover, in addition to the host cells, transgenic animals can also be used in the recombinant antibody production. Specifically, the antibody of interest can be obtained from animals transfected with the genes encoding this antibody. For example, the antibody genes can be inserted in frame into genes encoding proteins specifically produced in milk to construct fusion genes. For example, goat β casein can be used as the proteins secreted into milk. DNA fragments containing the fusion genes having the antibody gene insert are injected into goat embryos, which are in turn introduced into female goats. From milk produced by transgenic goats (or progeny thereof) brought forth by the goats that have received the embryos, the desired antibody can be obtained as a fusion protein with the milk protein. Moreover, in the transgenic goats, hormone can be used appropriately for increasing the amount of milk containing the desired antibody produced from the transgenic goats (Ebert, K. M. et al., Bio/Technology (1994) 12, 699-702).

Antibody Having Modified Sugar Chain

The anti-CLDN6 antibody of the present invention may be an antibody having a modified sugar chain. It is known that the cytotoxicity of antibodies can be enhanced by modifying their sugar chains.

Examples of the antibody having a modified sugar chain according to the present invention can include antibodies having modified glycosylation (WO 99/54342, etc.), antibodies deficient in fucose added to their sugar chains (WO 00/61739, WO 02/31140, WO 2006/067847, WO 2006/067913, etc.), and antibodies having a sugar chain having bisecting GlcNAc (WO 02/79255, etc.).

Preferable examples of the antibody having a modified sugar chain can include fucose-deficient antibodies. Sugar chains binding to antibodies are classified into: an N-glycoside-linked sugar chain which binds to an N atom in the side chain of asparagine of an antibody molecule; and an O-glycosyl-linked sugar chain which binds to a hydroxyl group in the side chain of serine or threonine of an antibody molecule. In the present invention, the presence or absence of fucose is of importance to the N-glycoside-linked sugar chain.

In the present invention, the fucose-deficient antibodies means that 20% or more, preferably 50% or more, more preferably 70% or more, even more preferably 90% or more, of the N-glycoside-linked sugar chains of antibodies in a composition are deficient in fucose.

The fucose-deficient antibodies can be prepared by a method generally known by those skilled in the art and can be produced, for example, by causing antibodies to be expressed in host cells having no or a little ability to add $\alpha$-1,6 core fucose. Examples of the host cells having no or a little ability to add fucose can include, but not particularly limited to, rat myeloma YB2/3HL.P2.G11.16Ag.20 cells (abbreviated to YB2/0 cells) (recorded as ATCC CRL 1662), FTVIII-knockout CHO cells (WO 02/31140), Lec13 cells (WO 03/035835), and fucose transporter-deficient cells (WO 2006/067847 and WO 2006/067913).

The sugar chains can be analyzed by a method generally known by those skilled in the art. For example, the sugar chains are released from the antibodies by the action of N-glycosidase F (Roche Diagnostics GmbH) on the antibodies. Then, the sugar chains are desalted by solid-phase extraction using a cellulose cartridge (Shimizu Y. et al., Carbohydrate Research 332 (2001), 381-388), then concentrated to dryness, and fluorescently labeled with 2-aminopyridine (Kondo A. et al., Agricultural and Biological Chemistry 54: 8 (1990), 2169-2170). From the obtained PA-sugar chains, the reagent is removed by solid-phase extraction using a cellulose cartridge, and the resulting sugar chains are then concentrated by centrifugation to prepare purified PA-sugar chains. Then, the sugar chains can be assayed by reverse-phase HPLC analysis on an ODS column. Alternatively, the PA-sugar chains thus prepared may be analyzed by two-dimensional mapping using reverse-phase HPLC analysis on an ODS column and normal phase HPLC analysis on an amine column in combination.

Chimeric Antibody and Humanized Antibody

Other preferable aspects of the antibody of the present invention can include chimeric and humanized antibodies. The chimeric antibodies refer to antibodies comprising regions of different origins ligated with each other. In general, the chimeric antibodies comprise non-human animal-derived antibody V regions and human antibody-derived C regions. For example, mouse-human heterogeneous chimeric antibodies consist of mouse antibody heavy and light chain variable regions and human antibody heavy and light chain constant regions.

By contrast, the humanized antibodies comprise non-human animal-derived antibody complementarity determining regions (CDRs), human antibody-derived framework regions (FRs), and human antibody-derived C regions. The humanized antibodies possess reduced antigenicity in human bodies and are therefore useful as active ingredients for a therapeutic agent of the present invention. The humanized antibodies are also called reshaped human antibodies. Specifically, for example, humanized antibodies are known in the art, which are obtained by grafting non-human animal (e.g., mouse) antibody CDRs into human antibodies. General gene recombination approaches for obtaining the humanized antibodies are also known.

Specifically, for example, Overlap Extension PCR is known in the art as the method for grafting mouse antibody CDRs into human FRs. In the Overlap Extension PCR, nucleotide sequences encoding the mouse antibody CDRs to be grafted are added to primers for human antibody FR synthesis. The primers are prepared for each of the 4 FRs. In the mouse CDR grafting into the human FRs, in general, human FRs highly homologous to mouse FRs are allegedly selected advantageously for maintaining the CDR functions. Specifically, human FRs are generally preferably used, which comprise amino acid sequences highly homologous to those of the FRs adjacent to the mouse CDRs to be grafted.

Moreover, nucleotide sequences to be ligated are designed such that they are connected in frame. The human FRs are individually synthesized using the primers specific therefor. As a result, products are obtained, which comprise the mouse CDR-encoding DNA added to each FR-encoding sequence. The mouse CDR-encoding nucleotide sequence in each product is designed such that the nucleotide sequence overlaps with another. Subsequently, the overlapping CDR portions in the products synthesized with human antibody genes as templates are annealed to each other for complementary strand synthesis reaction. Through this reaction, the human FR sequences are ligated via the mouse CDR sequences.

Finally, the full length of the gene of the V region comprising 3 CDRs and 4 FRs ligated is amplified with primers that anneal to the 5' or 3' end thereof and comprise the added sequences of appropriate restriction sites. The DNA thus obtained and human antibody C region-encoding DNA can be inserted into expression vectors such that they are fused in frame to prepare vectors for human antibody expression. The gene-incorporated vectors are introduced into hosts to establish recombinant cells, which are then cultured and caused to express the humanized antibody-encoding DNA to produce the humanized antibodies into the culture products of the cultured cells (see European Patent Publication No. EP 239400 and International Publication No. WO 96/02576).

The humanized antibodies thus prepared can be evaluated for their avidities for the antigens by qualitative or quantitative assay to preferably select human antibody FRs that allow, when ligated via CDRs, the CDRs to form a favorable antigen-binding site. If necessary, FR amino acid residue(s) can be substituted such that the CDRs of the reshaped human antibody form an appropriate antigen-binding site. For example, an amino acid sequence mutation can be introduced in FR by applying the PCR used in the mouse CDR grafting into the human FRs. Specifically, a mutation of a partial nucleotide sequence can be introduced in the primers annealing to the FR nucleotide sequence. The FR nucleotide sequence synthesized using such primers has been mutated. Variant antibodies having the substituted amino acid(s) can be evaluated for their avidities for the antigens by the same assay as above to select variant FR sequences having the desired property (Sato, K. et al., Cancer Res, 1993, 53, 851-856).

Human antibody C regions are used as the C regions of the humanized antibodies. $C\gamma 1$, $C\gamma 2$, $C\gamma 3$, $C\gamma 4$, $C\mu$, $C\delta$, $C\alpha 1$, $C\alpha 2$, $C\epsilon$, and the like can be used as H chain C regions, and $C\kappa$, $C\lambda$, and the like can be used as L chain C regions.

Moreover, the human antibody C regions may be modified for improving the stability of the antibody itself or its production. Any isotype of human antibodies such as IgG, IgM, IgA, IgE, and IgD may be used as the human antibodies used in humanization. In the present invention, IgG is preferably used. IgG such as IgG1, IgG2, IgG3, or IgG4 can be used.

For the humanized antibodies thus prepared, amino acid(s) in their variable (e.g., CDR or FR) or constant regions may be subjected to, for example, substitution with another amino acid, deletion, addition, and/or insertion. The humanized antibodies of the present invention also encompass such humanized antibodies that have undergone amino acid substitution or the like.

Bivalent Antibody, Low-Molecular-Weight Antibody, and Modified Antibody

The anti-CLDN6 antibody of the present invention encompasses not only bivalent antibodies typified by IgG but also monovalent antibodies or polyvalent antibodies typified by IgM as long as they bind to the CLDN6 protein. The polyvalent antibodies of the present invention encompass polyvalent antibodies having a plurality of antigen-binding sites, all of which are the same or some or all of which are different.

Moreover, the antibody of the present invention is not limited to whole antibody molecules and may be a low-molecular-weight antibody or a modified form thereof as long as it binds to the CLDN6 protein.

The low-molecular-weight antibody encompasses antibody fragments deficient in a portion of the whole antibody (e.g., whole IgG). Such partial deficiency of the antibody molecule is accepted as long as the resulting antibody fragments are capable of binding to the CLDN6 antigen. It is preferred that the antibody fragment according to the present invention should contain one or both of a heavy chain variable region (VH) and a light chain variable region (VL). The amino acid sequence of VH or VL can contain substitution, deletion, addition and/or insertion. Furthermore, the antibody fragment of the present invention may be deficient in a portion of one or both of VH and VL as long as it is capable of binding to the CLDN6 antigen. Moreover, the variable regions may be chimerized or humanized. Specific examples of the antibody fragment can include Fab, Fab', F(ab')2, and Fv. Moreover, specific examples of the low-molecular-weight antibody can include Fab, Fab', F(ab')2, Fv, and scFv (single chain Fv), Diabody, and sc(Fv)2 (single chain (Fv)2). Multimers (e.g., dimmers, trimers, tetramers, and polymers) of these antibodies are also encompassed by the low-molecular-weight antibody of the present invention.

These fragments of the antibody can be obtained by enzymatically treating the antibody to form antibody fragments. For example, papain, pepsin, or plasmin is known in the art as the enzyme for forming the antibody fragments. Alternatively, genes encoding these antibody fragments can be constructed, then introduced into expression vectors, and then expressed in appropriate host cells (see e.g., Co, M. S. et al., J. Immunol. (1994) 152, 2968-2976, Better, M. & Horwitz, A. H. Methods in Enzymology (1989) 178, 476-496, Plueckthun, A. & Skerra, A. Methods in Enzymology (1989) 178, 476-496, Lamoyi, E., Methods in Enzymology (1989) 121, 652-663, Rousseaux, J. et al., Methods in Enzymology (1989) 121, 663-669, and Bird, R. E. et al., TIBTECH (1991) 9, 132-137).

The Diabody refers to a bivalent antibody fragment constructed by gene fusion (e.g., Holliger P et al., Proc. Natl. Acad. Sci. USA 90: 6444-6448 (1993), EP 404,097, and WO 93/11161). The Diabody is a dimer comprising two polypeptide chains. Usually, each of the polypeptide chains constituting the dimer comprises VL and VH linked via a linker on the same chain. The linker in the Diabody is generally too short to allow paring between VL and VH on the same chain. Specifically, the number of amino acid residues constituting the linker is, for example, approximately 5 residues. Therefore, VL and VH encoded on the same polypeptide chain cannot together form a single chain variable region fragment. Instead, they pair with the complementary domains of another single chain variable region fragment to form a dimer. As a result, the Diabody has two antigen-binding sites.

The scFv is obtained by linking an H chain V region and an L chain V region of the antibody. In the scFv, the H chain V region and the L chain V region is linked via a linker, preferably, a peptide linker (Huston, J. S. et al., Proc. Natl. Acad. Sci. U.S.A, 1988, 85, 5879-5883). The H chain V region and the L chain V region in the scFv may be derived from any of those described as antibodies in the present specification. The peptide linker that links the V regions is not particularly limited. For example, an arbitrary single chain peptide of approximately 3 to 25 residues can be used as the linker.

The sc(Fv)2 is a low-molecular-weight antibody having a single chain comprising two VHs and two VLs linked via linkers or the like (Hudson et al., J. Immunol. Methods 1999; 231: 177-189). The sc(Fv)2 can be prepared, for example, by linking scFvs via a linker.

Furthermore, the antibody of the present invention may be used as a modified antibody comprising various molecules (e.g., polyethylene glycol (PEG)) bound thereto. Such a modified antibody can be obtained by chemically modifying the antibody of the present invention. A method for the antibody modification has already been established in the art.

Furthermore, the antibody of the present invention may be a bispecific antibody. The bispecific antibody refers to an antibody having, in the same antibody molecule, variable regions that recognize different epitopes. The epitopes may be located in different molecules or may be located in the same molecule. Specifically, in the present invention, the bispecific antibody can have antigen-binding sites that recognize different epitopes on the CLDN6 protein. Thus, two such bispecific antibody molecules can bind to one CLDN6 molecule. As a result, stronger cytotoxic effect can be expected. These antibodies are also encompassed by the "antibody" according to the present invention.

Moreover, in the present invention, a bispecific antibody that recognizes an antigen other than CLDN6 can be combined therewith. For example, the bispecific antibody that can be combined therewith recognizes an antigen that is specifically expressed on the surface of a target cancer cell, as with CLDN6, but is different from CLDN6.

A method for producing the bispecific antibody is known in the art. For example, two antibodies differing in antigen recognized thereby can be bound to prepare the bispecific antibody. Each of the antibodies bound may be a ½ molecule having H and L chains or may be a ¼ molecule consisting of H chains. Alternatively, different monoclonal antibody-producing hybridomas can also be fused to prepare fusion cells producing bispecific antibodies. Furthermore, the bispecific antibody can be prepared by a genetic engineering approach.

Pharmaceutical Composition

The present invention provides a pharmaceutical composition comprising the anti-CLDN6 antibody as an active ingredient. Moreover, the present invention relates to an anti-cancer agent comprising the anti-CLDN6 antibody as an active ingredient. It is preferred that the anticancer agent of the present invention should be administered to a subject suffering from cancer or having a possibility of cancer recurrence.

Moreover, in the present invention, the anticancer agent comprising the anti-CLDN6 antibody as an active ingredient can also be expressed as a method for preventing or treating cancer, comprising the step of administering the anti-CLDN6 antibody to a subject, or as use of the anti-CLDN6 antibody for producing an anticancer agent.

The type of the cancer treated with the anticancer agent of the present invention is not particularly limited and is usually cancer expressing the CLDN6 proteins, preferably lung adenocarcinoma, gastric cancer, or ovarian cancer. Moreover, the type of the cancer treated with the anticancer agent of the present invention is more preferably, but not particularly limited to, cancer highly expressing the CLDN6 proteins.

In the present invention, the phrase "comprising the anti-CLDN6 antibody as an active ingredient" means comprising the anti-CLDN6 antibody as a principal active ingredient and does not limit the content of the monoclonal antibody.

Furthermore, the pharmaceutical composition, cell growth inhibitor, or anticancer agent according to the present invention can be formulated, if necessary, with plural types of antibodies. For example, the cytotoxic effect on CLDN6-expressing cells can probably be enhanced by preparing a cocktail containing a plurality of anti-CLDN6 antibodies. Alternatively, the therapeutic effect can also be enhanced by formulating therein the anti-CLDN6 antibody as well as antibodies that recognize other tumor-related antigens.

The pharmaceutical composition, cell growth inhibitor, or anticancer agent of the present invention can be administered either orally or parenterally to a patient. Parenteral administration is preferable. Specific examples of the administration method include injection, transnasal, pulmonary, and transdermal administrations. Examples of the injection administration include intravenous, intramuscular, intraperitoneal, and subcutaneous injections, through which the pharmaceutical composition of the present invention can be administered systemically or locally. Moreover, the administration method can be selected appropriately according to the age or symptoms of the patient. The dose thereof can be selected from among a dose range of, for example, 0.0001 mg to 1000 mg per kg body weight per dosing. Alternatively, the dose can be selected from among a range of, for example, 0.001 to 100000 mg/body per patient. However, the pharmaceutical composition of the present invention is not limited to these doses.

The pharmaceutical composition of the present invention can be formulated according to a standard method (e.g., Remington's Pharmaceutical Science, latest edition, Mark Publishing Company, Easton, U.S.A) and may additionally contain pharmaceutically acceptable carriers or additives. Examples thereof include, but not limited thereto, surfactants, excipients, coloring agents, flavoring agents, preservatives, stabilizers, buffers, suspending agents, tonicity agents, binders, disintegrants, lubricants, flow promoters, and corrigents. Other carriers routinely used can be used appropriately. Specific examples of the carriers can include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinyl pyrrolidone, gelatin, middle chain fatty acid triglyceride, polyoxyethylene hydrogenated castor oil 60, white sugar, carboxymethylcellulose, corn starch, and inorganic salts.

Moreover, the present invention provides a method for causing damage to CLDN6-expressing cells or inhibiting the growth thereof, comprising contacting the CLDN6-expressing cells with the anti-CLDN6 antibody. The anti-CLDN6 antibody is as described above. The cells to which the anti-CLDN6 antibody binds are not particularly limited as long as they express CLDN6. In the present invention, the CLDN6-expressing cells are preferably cancer cells. Preferable examples of the cancer cells can include lung adenocarcinoma cells, gastric cancer cells, and ovarian cancer cells.

In the present invention, the "contact" may be performed in vitro or in vivo. For example, the contact is performed by adding the antibody to a culture solution of CLDN6-expressing cells cultured in a test tube. In this case, forms such as solutions or solids obtained by freeze-drying or the like can be used appropriately as forms of the antibody added. When the antibody is added as an aqueous solution, the aqueous solution may purely contain only the antibody or may additionally contain, for example, the surfactants, excipients, coloring agents, flavoring agents, preservatives, stabilizers, buffers, suspending agents, tonicity agents, binders, disintegrants, lubricants, flow promoters, corrigents described above. The concentration of the antibody added is not particularly limited. Preferably, a range of 1 pg/ml to 1 g/ml, more preferably 1 ng/ml to 1 mg/ml, even more preferably 1 µg/ml to 1 mg/ml can be used preferably in terms of a final concentration in the culture solution.

In a further alternative aspect of the present invention, the "contact" is also performed by administering the anti-CLDN6 antibody to non-human animals implanted with CLDN6-expressing cells in their bodies or animals endogenously having cancer cells expressing CLDN6. A method for the administration can be performed either orally or parenterally. An administration method through parenteral administration is particularly preferable. Specific examples of the administration method include injection, transnasal, pulmonary, and transdermal administrations. Examples of the injection administration include intravenous, intramuscular, intraperitoneal, and subcutaneous injections, through which the pharmaceutical composition, cell growth inhibitor, or anticancer agent of the present invention can be administered systemically or locally. Moreover, the administration method can be selected appropriately according to the age or symptoms of the animal subject. When the antibody is administered as an aqueous solution, the aqueous solution may purely contain only the antibody or may additionally contain, for example, the surfactants, excipients, coloring agents, flavoring agents, preservatives, stabilizers, buffers, suspending agents, tonicity agents, binders, disintegrants, lubricants, flow promoters, and corrigents described above. The dose thereof can be selected from among a dose range of, for example, 0.0001 mg to 1000 mg per kg body weight per dose. Alternatively, the dose can be selected from among a range of, for example, 0.001 to 100000 mg/body per patient. However, the antibody of the present invention is not limited to these doses.

Diagnostic Method

The present invention further provides a method for diagnosing cancer using the anti-CLDN6 antibody. The cancer diagnosed by the method of the present invention is not particularly limited as long as it expresses CLDN6. The cancer is preferably lung adenocarcinoma, gastric cancer, or ovarian cancer.

The diagnostic method of the present invention may be performed in vitro or in vivo. Preferably, the diagnostic method is performed in vitro.

The method for diagnosing cancer using the anti-CLDN6 antibody of the present invention is, for example, a method comprising the following steps:
(a) providing a sample collected from a subject; and
(b) detecting a CLDN6 protein contained in the sample collected in the step (a).

In the present invention, the detection encompasses quantitative or qualitative detection. The qualitative detection encompasses, for example, assay on the presence or absence of the CLDN6 protein, assay on the presence or absence of more than a predetermined amount of the CLDN6 protein, and assay comprising comparing the amount of the CLDN6 protein with that contained in another sample (e.g., a control sample). The quantitative assay encompasses, for example, measurement of a CLDN6 protein concentration and measurement of the amount of the CLDN6 protein.

The test sample according to the present invention is not particularly limited as long as it is a sample likely to contain the CLDN6 protein. Specifically, samples collected from living bodies such as mammals are preferable. Samples collected from humans are more preferable. Specific examples of the test sample can include blood, interstitial fluid, plasma, extravascular fluid, cerebrospinal fluid, synovial fluid, pleural fluid, serum, lymph, saliva, urine, and tissues. The sample is preferably a preparation on which tissues or cells collected from living bodies are immobilized, or a sample obtained from the test sample, such as a cell culture solution.

The CLDN6 protein detection can be performed by a method generally known by those skilled in the art and can be performed by, for example, radioimmunoassay (RIA), enzyme immunoassay (EIA), fluorescent immunoassay (FIA), luminescent immunoassay (LIA), immunoprecipitation (IP), turbidimetric immunoassay (TIA), western blot (WB), immunohistochemical (IHC) method, or single radial immunodiffusion (SRID).

In the present invention, when the CLDN6 protein is detected (e.g., when a larger amount of the CLDN6 protein is contained in the test sample than in a control sample, or when more than a predetermined amount of the CLDN6 protein is contained in the test sample), the subject is diagnosed as having cancer or highly possibly having cancer.

EXAMPLES

Hereinafter, the present invention will be described in more detail with reference to Examples. However, the present invention is not intended to be limited to these Examples.

Example 1

Analysis of Human CLDN6 mRNA Expression Using Human Exon 1.0 ST Array

To elucidate the distribution of human CLDN6 mRNA expression in clinical cancers, cancer cell lines, and various normal organs, expression analysis was conducted using Human Exon 1.0 ST Array (Affymetrix, Inc.) originally developed for splicing variant analysis. The expression analysis using Human Exon 1.0 ST Array has an advantage that the Human Exon 1.0 ST Array includes at least one probe set per exon of a gene compared with previous expression arrays of Affymetrix, Inc. which basically include only one 3' probe set per gene; thus the expression analysis of each gene using this array can provide expression data derived from a plurality of probe sets per gene, resulting in enhanced reliability of expression data per gene.

This expression analysis utilized total RNAs derived from 22 tumor areas of tissues after resection of lung adenocarcinoma, 2 normal areas of tissues after resection of lung adenocarcinoma, 13 tumor areas of tissues after resection of gastric cancer, 20 tumor areas of tissues after resection of ovarian cancer, 19 types of lung adenocarcinoma cell lines, 4 types of small-cell lung cancer cell lines, 10 types of gastric cancer cell lines, 20 types of ovarian cancer cell lines, and 65 types of normal tissues (purchased from Clontech Laboratories, Inc., Ambion, Inc., STRATAGENE, Cell APPLICATIONS, Inc., Panomics Inc., CHEMICON, and BioChain Institute, Inc.).

All the tumor or normal areas of tissues after resection of clinical cancer (after obtainment of informed consent) and the cancer cell lines (purchased from ATCC, JCRB, and Riken BIOSOURCE CENTER CELL BANK) were subjected to total RNA extraction using Trizol (Invitrogen Corp.) according to the protocol included in the product. 1 μg of each total RNA was used to conduct the experiment of gene expression analysis according to GeneChip Whole Transcript (WT) Sense Target Labeling Assay Manual (Affymetrix, Inc.), and Human Exon 1.0 ST Array Data was converted into digital data using ExACT (Exon Array Computational Tool) software provided by Affymetrix, Inc.

Figure 2:
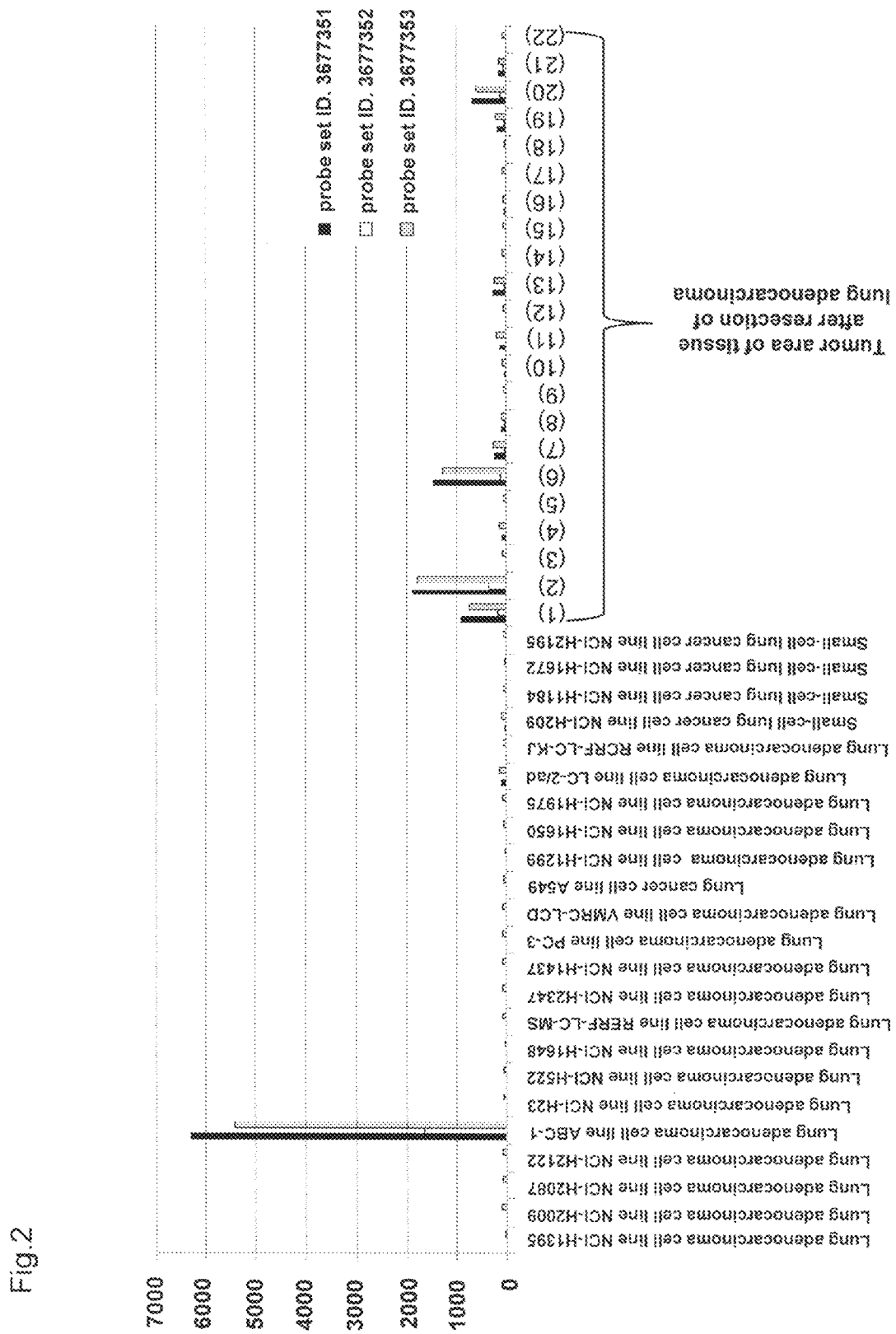
FIG. 2 shows the expression profile of human CLDN6 in lung cancer.
Figure 3:
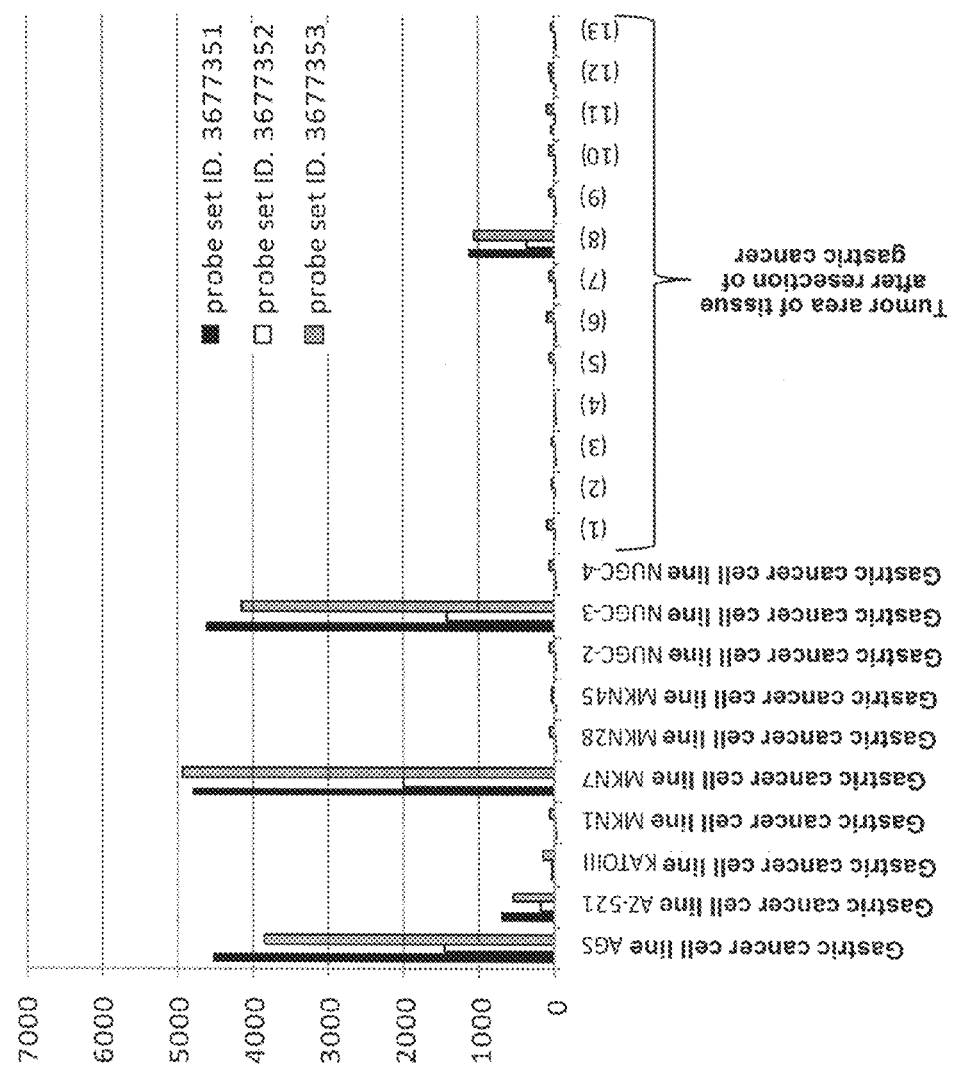
FIG. 3 shows the expression profile of human CLDN6 in gastric cancer.
Figure 4:
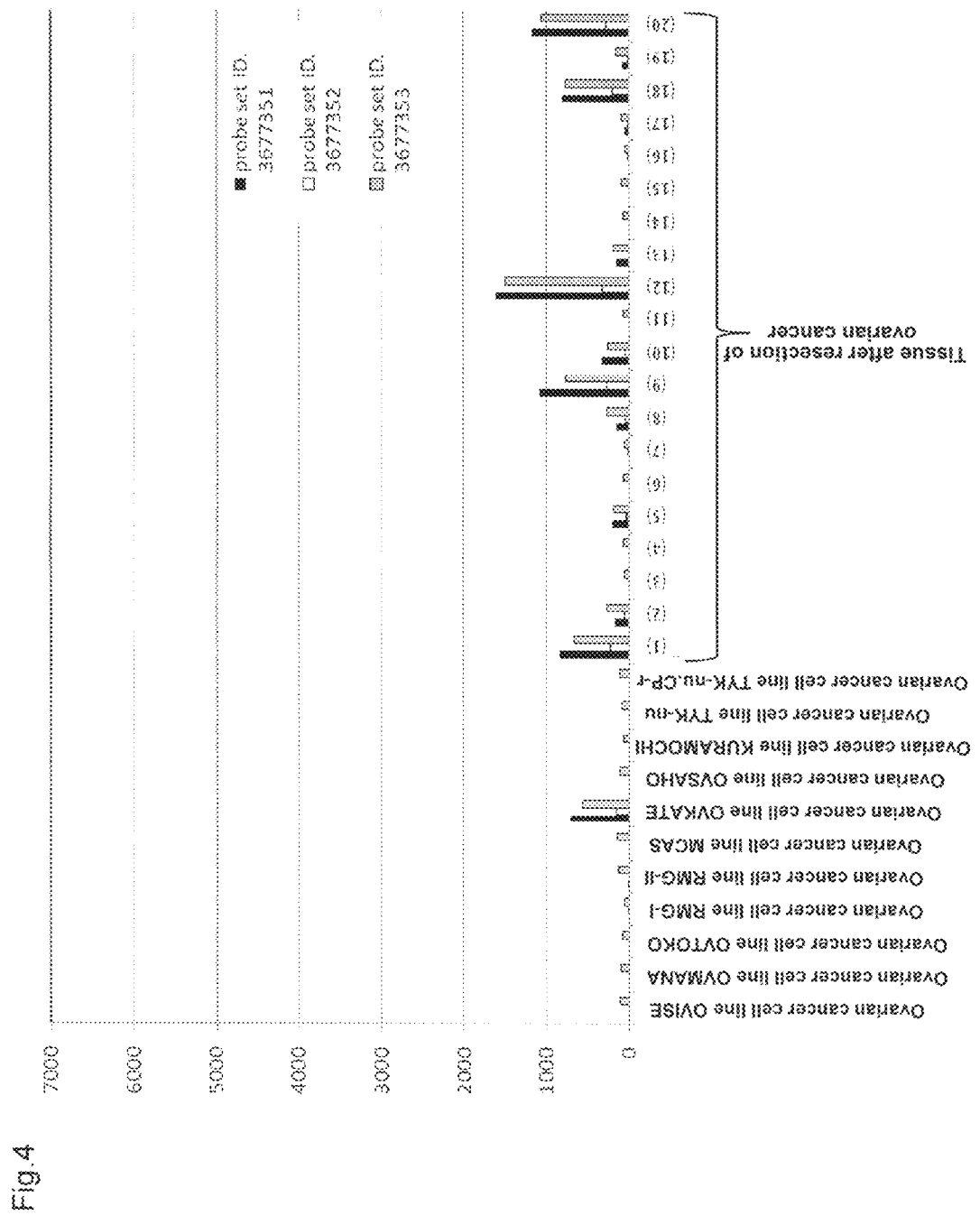
FIG. 4 shows the expression profile of human CLDN6 in ovarian cancer.

The Human Exon 1.0 ST Array contains three core probe sets for human CLDN6, whose IDs are 3677351, 3677352, and 3677353. The expression data obtained from the normal tissues using these three probe set IDs is shown in FIG. 1; the expression data obtained from the lung adenocarcinoma cell lines, the small-cell lung cancer cell lines, and the tumor areas of tissues after resection of lung adenocarcinoma using them is shown in FIG. 2; the expression data obtained from the gastric cancer cell lines and the tumor areas of tissues after resection of gastric cancer using them is shown in FIG. 3; and the expression data obtained from the ovarian cancer cell lines and the tumor areas of tissues after resection of ovarian cancer using them is shown in FIG. 4.

As can be seen from FIGS. 1 to 4, no human CLDN6 transcript was expressed in the normal tissues except for fetal lung (the expression in the adult normal tissues examined this time was negligibly low compared with that in the tumor tissues), whereas its high expression, albeit with a low frequency, was observed in the lung, gastric, and ovarian cancers. These results show that antitumor agents targeting human CLDN6 are totally free from concerns about adverse reaction in normal tissues and are thus expected to exert their efficacy largely alienated from adverse reaction.

Example 2

Analysis of Human CLDN6 Protein Expression in Cancer Cell Lines

Human CLDN6 protein expression in cancer cell lines was analyzed using western blot on cell line lysates.

Based on the analysis results of human CLDN6 mRNA expression obtained using Human Exon 1.0 ST Array and Human Genome U133 Set Array, 2 lines (i.e., lung adenocarcinoma cell line ABC-1 and gastric cancer cell line AGS) were used in the experiment as cell lines highly expressing human CLDN6 mRNA, while 4 lines (i.e., lung adenocarcinoma cell line NCI-H2347, small-cell lung cancer cell line NCI-H209, small-cell lung cancer cell line NCI-H1672, and small-cell lung cancer cell line NCI-H1184) were used as cell lines free from human CLDN6 mRNA expression. ABC-1 was purchased from JCRB Cell Bank, and AGS, NCI-H2347, NCI-H209, NCI-H1672, and NCI-H1184 were purchased from ATCC.

The cells were scraped from dishes using 1 mM EDTA/PBS (-). To 1×10$^6$ cells, 50 uL of NP40 Lysis Buffer [0.5% Nonidet P40 (v/v), 50 mM Tris-HCl (pH 7.5), 150 mM NaCl, 5 mM EDTA, 1 tablet/10 mL Complete mini EDTA free (Roche Diagnostics GmbH, 04 693 159 001), 100 ug/mL p-APMSF (p-Amidinophenyl)-methanesulfonyl Fluoride Hydrochloride (Wako Pure Chemical Industries, Ltd., 014-

10391)] was added, and the cells were dissolved by pipetting, then left standing for 30 minutes on ice, and centrifuged at 15000 rpm at 4° C. for 30 minutes. The resulting supernatants were used as cell line lysates.

Each lysate thus prepared was mixed with a 2× sample buffer (SIGMA-ALDRICH CORP., S3401-IVL) at a 1:1 ratio, and the mixture was then incubated at room temperature for 15 minutes. 10 uL aliquots (lysates of 1×10^5 cells each) were subjected to western blot. In the western blot, 15 to 25% polyacrylamide was used; goat anti-claudin-6 polyclonal antibodies (C-20) (Santa Cruz Biotechnology, Inc., Code. sc-17669 Lot. H2605), which are polyclonal antibodies against the C-terminal peptide of human CLDN6, were diluted 1/200 and used as primary antibodies; and swine anti-goat Ig's HRP conjugates (BIOSOURCE International Code. ACI3404 Lot. 4101) were diluted 1/20000 and used as secondary antibodies. ECL Plus Western Blotting Detection System (GE Healthcare Bio-Sciences Corp. Code. RPN2132) was used in color development, and the membrane with the developed color thereon was exposed to Hyperfilm ECL (GE Healthcare Bio-Sciences Corp. Code. 28-9068-36).

Figure 5:
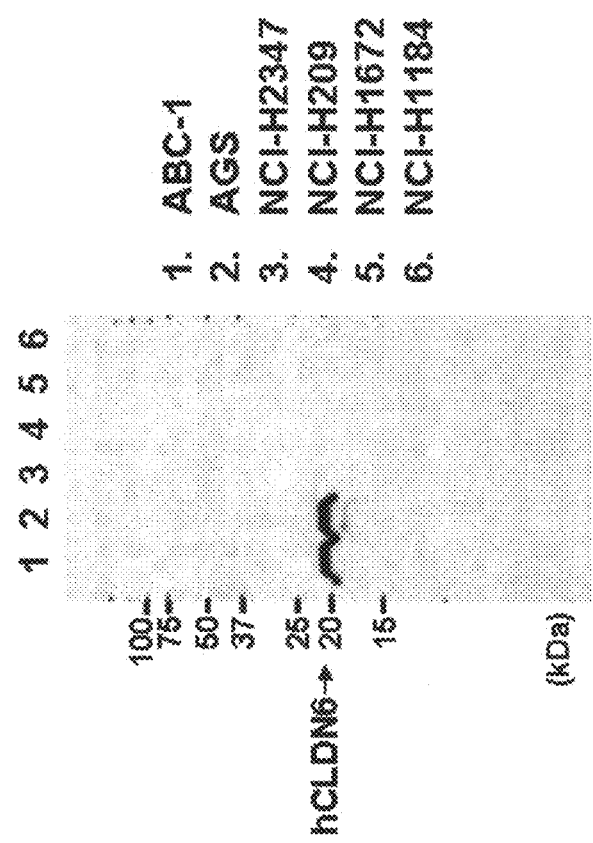
FIG. 5 shows western blot using goat anti-CLDN6 polyclonal antibodies (Santa Cruz Biotechnology, Inc., C-20, Code. sc-17669)

As shown in FIG. 5, the obtained protein expression results well correlated with the transcriptome analysis results shown in [Example 1]. From the results, it can be concluded that human CLDN6 protein expression is in exceedingly good agreement with human CLDN6 mRNA expression. Thus, the transcriptome analysis results obtained using Exon Array shown in [Example 1] are almost consistent with the analysis results of protein expression. This shows for the first time that human CLDN6 proteins are hardly expressed in adult normal tissues and expressed at increased levels in tumors.

Example 3

Preparation of Antibodies Recognizing Human CLDN6 on Cancer Cell Membrane Surface, and Assay on Antitumor Activities of the Antibodies As shown in Examples 1 and 2, human CLDN6 protein expression well correlated with its mRNA expression. Moreover, human CLDN6 mRNA expression in adult normal tissues was shown to be considerably low or almost absent compared with that in tumor tissues. Thus, human CLDN6 protein expression in adult normal tissues was also presumed to be almost absent compared with that in tumor tissues. This means that antibodies recognizing the human CLDN6 proteins expressed on cancer cell surface are exceedingly highly tumor-specific antibodies. Such antibodies, when used as antitumor agents, can be expected to exert their efficacy largely alienated from adverse reaction. In addition, this means that human CLDN6 has an exceedingly high potential as a target for antitumor agents.

Thus, antibodies recognizing human CLDN6 on cancer cell membrane surface were actually prepared and evaluated for their antitumor effects.

3-1. Cloning of Human CLDN6 cDNA

To prepare antibodies against human CLDN6, a sequence containing the open reading frame of human CLDN6 (Refseq Accession No. NM_021195.3) cDNA was cloned. Human CLDN6 cDNA was cloned using Marathon-Ready cDNA Fetal Lung (Clontech Laboratories, Inc. Code. 639333) as a template and primers represented by SEQ ID NOs: 1 and 2. Specifically, KOD plus DNA polymerase (TOYOBO CO., LTD.) was used to prepare a solution containing 5 μL of 10×KOD Buffer, 5 uL of 2 mM dNTPs, 3 uL of 25 mM MgSO$_4$, 1.5 uL of 10 μM primer of SEQ ID NO: 1, 1.5 uL of 10 μM primer of SEQ ID NO: 2, 2 uL of Template fetal lung cDNA, 1 uL of KOD plus DNA polymerase, and 31 uL of nuclease-free water, and the prepared solution was used in PCR amplification at 94° C. for 2 min followed by 30 cycles each involving 94° C. for 15 sec, 58° C. for 30 sec, and 68° C. for 1 min. Next, this amplification product was used as a template to further perform reamplification at 94° C. for 2 min followed by 20 cycles each involving 94° C. for 15 sec, 58° C. for 30 sec, and 68° C. for 1 min, using primers represented by SEQ ID NOs: 3 and 4 and a solution with the same composition as above containing the same enzyme as above. The amplified fragment was digested with HindIII and NheI and cloned into the HindIII-NheI sites of pMCN-flag vectors.

3-2. Preparation of Human CLDN6-Expressing CHO (DG44) and Human CLDN6-Expressing Ba/F3 Cells pCOS2 vectors were used as expression vectors for mammals for preparing human CLDN6-expressing CHO cells (DG44, purchased from Invitrogen Corp.) and human CLDN6-expressing Ba/F3 cells. The pCOS2 vectors incorporate thereon an EF1α promoter-enhancer sequence as a promoter for inducing the expression of the gene of interest, and the expression of the gene of interest can be induced in vector-transformed cells by inserting the cDNA sequence of the gene of interest downstream of the promoter-enhancer. Moreover, the vector-transformed cells can be screened using neomycin, because the vectors incorporate a neomycin resistance gene therein.

The plasmids comprising the cloned human CLDN6 cDNA described in [Example 3-1.] were used as templates to perform PCR using a primer represented by SEQ ID NO: 5 (the sequence of an EcoRI site, a Kozak sequence, and the 5'-terminal sequence of the human CLDN6 (Refseq Accession No. NM_021195.3) open reading frame) and a primer represented by SEQ ID NO: 6 (the sequence of a NotI site and the 3'-terminal sequence of the human CLDN6 open reading frame). The PCR amplification product was cloned into pCR 2.1-TOPO vectors using TOPO TA Cloning (Invitrogen Corp.). These vectors were digested with EcoRI and NotI, and the resulting human CLDN6 fragment was incorporated into the EcoRI-NotI sites of pCOS2 vectors to construct human CLDN6/pCOS2 expression vectors.

The human CLDN6/pCOS2 was digested with PvuI, and the digestion product was introduced into CHO (DG44) and Ba/F3 cells by electroporation (using GenePulser II, BIO-RAD LABORATORIES, INC.). The transformed cell lines were screened using 500 ug/mL Geneticin to establish CHO (DG44) and Ba/F3 cells stably expressing human CLDN6.

Moreover, the human CLDN6/pCOS2 vectors were also used in DNA immunization described below.

3-3. Preparation of Anti-Human CLDN6 Antibodies

To prepare anti-human CLDN6 antibodies, DNA immunization using Helios Gene Gun (BIO-RAD LABORATORIES, INC.) and cell immunization using the Ba/F3 cells forced to express human CLDN6 were preformed in combination for immunization of mice. Monoclonal antibodies were screened by flow cytometry using the human CLDN6-expressing CHO (DG44) cells.

The mice used in the immunization were strain name: BALB/cAnNCrlCrlj and strain name: MRL/MpJ-Tnfrsf6<lpr>/Crlj Genotype: lpr/lpr purchased from Charles River Laboratories Japan, Inc. For the DNA immunization using Gene Gun, the human CLDN6/pCOS2 vectors described in [Example 3-2.] were used, and the coating of gold particles with plasmid DNAs and the immunization of the mice were performed according to the "HELIOS GENE GUN simple operation manual ver. 2.1" of BIO-RAD LABORATORIES, INC. The DNA immunization schedule involved a total of approximately 8 to 17 immunizations in which one mouse was immunized 1 to 3 times per week at 2 shots/immunization. The antibody titer in the mouse serum was periodically measured by flow cytometry using the cell lines forced to express human CLDN6. After confirmation of increase in the antibody titer caused by DNA immunization, cell immunization with the Ba/F3 cell line forced to express human CLDN6 was performed through the tail vein. 2 to 3 days after the final cell immunization, the spleen cells were extracted and subjected to a cell fusion method with a mouse myeloma cell line P3X63Ag8U.1 (P3U1, purchased from ATCC) to prepare antibody-producing immortalized hybridomas. For the cell fusion between the mouse spleen cells and the mouse myeloma cell line P3X63Ag8U.1, these cells were mixed at a spleen cell-P3X63Ag8U.1 cell ratio of 2 to 4:1. To the cell mixture, PEG1500 (Roche Diagnostics GmbH) was added gradually and carefully, and the PEG1500 was then diluted with an RPMI1640 medium and removed by centrifugation. Next, the fusion cells were suspended in a HAT medium (RPMI1640 (Invitrogen Corp.) medium containing 10% Fetal Bovine Serum (Roche Diagnostics GmbH), 1× Penicillin-Streptomycin (Invitrogen Corp.), 1×HAT media supplement (Sigma-Aldrich Corp.), and 0.5×BM-Condimed H1 Hybridoma Cloning Supplement (Roche Diagnostics GmbH)) and inoculated to 10 to 30 96-well plates. The cells were cultured for 7 to 10 days in a $CO_2$ incubator at 37° C. Then, screening was conducted using the hybridoma culture supernatant. The screening was conducted by assaying the avidities of the antibodies for the CHO cells forced to express human CLDN6 using a flow cytometer (Becton, Dickinson and Company). Since positive wells were likely to have a plurality of hybridomas, the hybridomas were cloned as single clones by a limiting dilution method. After the cloning as single clones, hybridoma clones producing antibodies with strong avidity for the CHO and Ba/F3 cells forced to express human CLDN6 were selected to establish hybridomas producing antibodies recognizing human CLDN6 on cell membrane surface.

Of them, particularly, 18 types of hybridomas were selected, which produced antibodies that were shown in flow cytometry to have strong avidity for the cell lines forced to express human CLDN6 and were shown in isotyping to be an IgG type. The selected hybridomas were cultured in a HAT medium containing Ultra Low IgG FBS (Invitrogen Corp.) instead of FBS, and the antibodies were purified from the culture supernatant using HiTrap Protein G HP 1 mL column (GE Healthcare Bio-Sciences Corp.). The antibodies were confirmed by SDS-PAGE and CBB staining to have a sufficient purity level. In this context, the antibody isotyping was performed using IsoStrip (Roche Diagnostics GmbH). The concentrations of the purified antibodies were measured using Dc Protein Assay Kit I (BIO-RAD LABORATORIES, INC.) with the included bovine γ globulin as a standard. The antibody concentrations were indicated in terms of bovine γ globulin concentrations. The antibody purification, the isotyping, and the protein quantification were all performed according to the manuals included in the products.

3-4. Assay on Avidities of Anti-Human CLDN6 Monoclonal Antibodies for Human CLDN6 on Surface of Ba/F3 Cells Forced to Express Human CLDN6

The purified anti-human CLDN6 monoclonal antibodies described in [Example 3-3] were evaluated for their avidities for 18 types of Ba/F3 cells forced to express hCLDN6 and for their parent line Ba/F3 by flow cytometry at adjusted antibody concentrations.

Each cell was suspended at a concentration of $1\times10^5$ cells in a FACS buffer (0.5% BSA, 1×PBS (−), 0.1% $NaN_3$), and the cell suspension was dispensed into a U-bottom 96-well plate (FALCON 353910). Each antibody was added thereto at final concentrations of 10, 2, 0.4, 0.08, and 0 µg/mL, then mixed, and incubated at 4° C. for 1 hour. After centrifugation, the reaction solution was removed by aspiration, and the cells were washed by the addition of 200 uL/well FACS buffer. Then, FITC-labeled Goat F(ab')$_2$ Fragment Anti-mouse IgG (Fcγ) (BECKMAN COULTER, Inc.) was diluted 100-fold with a FACS buffer and added as secondary antibodies to the cells. The cells were incubated at 4° C. for 30 minutes, then washed with the same FACS buffer as above, and suspended in 100 uL of a FACS buffer containing propidium iodide (SIGMA-ALDRICH CORP.) at a concentration of 10 µg/mL. The cell suspension was subjected to flow cytometry.

In the flow cytometry, a gate was constructed for a live cell population in a dot plot of an X axis: forward scatter against a Y axis: side scatter and a dot plot of an X axis: forward scatter against a Y axis: propidium iodide fluorescence (FL-3).

Figure 6:
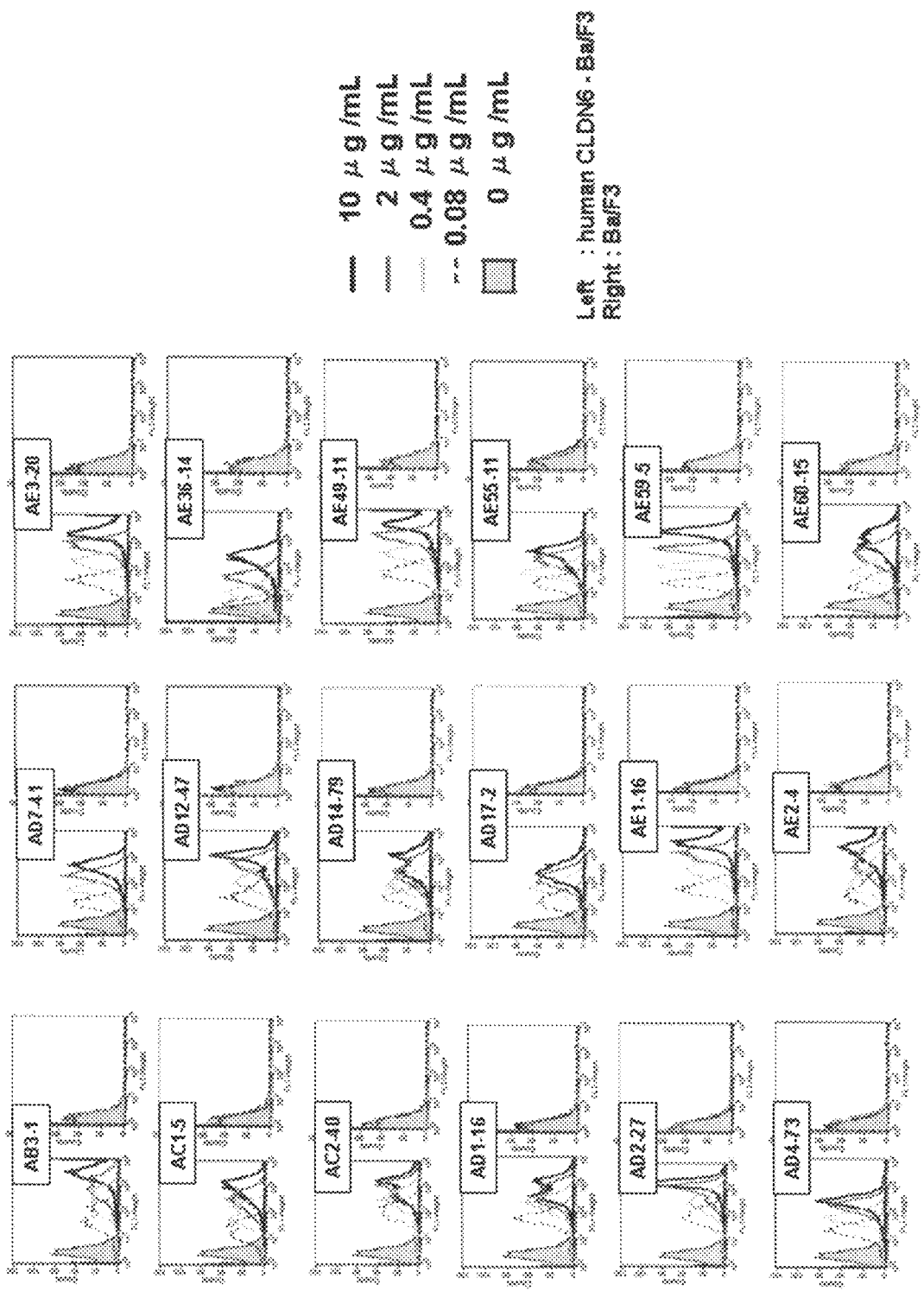
FIG. 6 shows the assay (flow cytometry analysis) of the avidities of anti-human CLDN6 antibodies for cells forced to express human CLDN6 and for their parent line.

As shown in FIG. 6, the antibodies of the present invention are human CLDN6-specific antibodies that do not bind to the Ba/F3 cells as the parent line and strongly bind to the Ba/F3 cells forced to express human CLDN6.

3-5. Assay on Avidities of Anti-Human CLDN6 Antibodies for Human CLDN6 on Cancer Cell Membrane Surface Although polyclonal antibodies recognizing the C-terminal intracellular peptide sequence of human CLDN6 are known, none of already known antibodies recognize the extracellular region of human CLDN6 present in a native form on cancer cell membrane surface. Thus, the anti-human CLDN6 monoclonal antibodies of the present invention prepared in [Example 3-3] were evaluated by flow cytometry for whether or not these antibodies recognize not only cell lysates of cell lines forced to express human CLDN6 but also human CLDN6 actually present on cancer cell membrane surface.

A lung adenocarcinoma cell line ABC-1 and a gastric cancer cell line AGS were used as human CLDN6-positive cancer cell lines, based on the analysis results of gene and protein expressions of [Example 1] and [Example 2].

Each cell was suspended at a concentration of $1\times10^5$ cells in a FACS buffer (0.5% BSA, 1×PBS (−), 0.1% $NaN_3$), and the cell suspension was dispensed into a U-bottom 96-well plate (FALCON 353910). Each antibody was added thereto at final concentrations of 10, 1, and 0 µg/mL, then mixed, and incubated at 4° C. for 1 hour. After centrifugation, the reaction solution was removed by aspiration, and the cells were washed by the addition of 200 uL/well FACS buffer. Then, FITC-labeled Goat F(ab')$_2$ Fragment Anti-mouse IgG (Fcγ) (BECKMAN COULTER, Inc.) was diluted 100-fold with a FACS buffer and added as secondary antibodies to the cells. The cells were incubated at 4° C. for 1 h, then washed with the same FACS buffer as above, and suspended in 120 uL of a FACS buffer. The cell suspension was subjected to flow cytometry.

In the flow cytometry, a gate was constructed for a live cell population in a dot plot of an X axis: forward scatter against a Y axis: side scatter.

Figure 7:
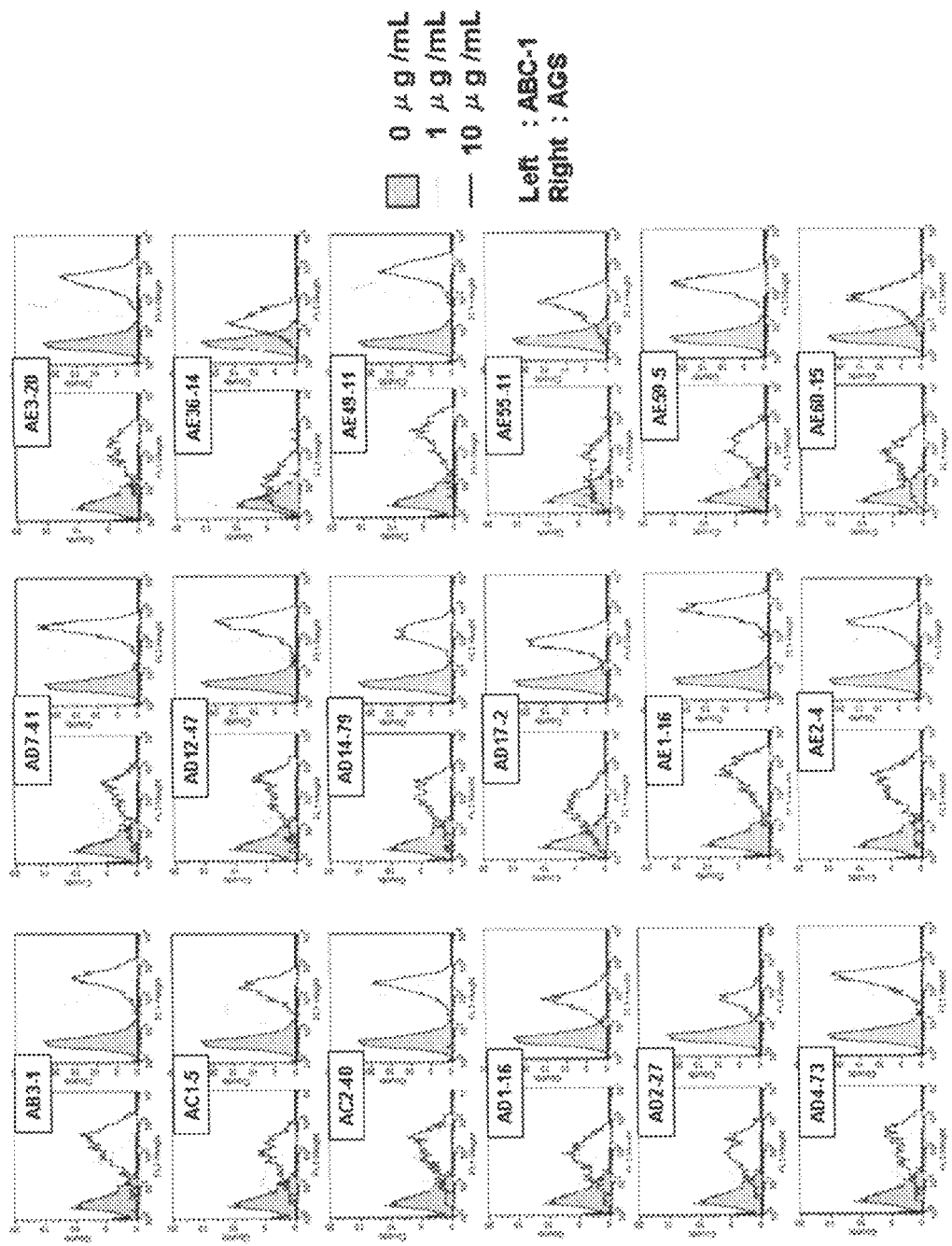
FIG. 7 shows the assay (flow cytometry analysis) of the avidities of anti-human CLDN6 antibodies for a lung adenocarcinoma cell line ABC-1 and a gastric cancer cell line AGS.

As shown in FIG. 7, all of these 18 types of antibodies prepared in [Example 3-3] bound in a concentration-dependent manner, albeit to a varying degree, to the ABC-1 and AGS cells as human CLDN6-expressing cancer cell lines.

3-6. Measurement of Antibody-Dependent Cellular Cytotoxicity (ADCC) Activities of Anti-Human CLDN6 Antibodies The anti-human CLDN6 monoclonal antibodies of the present invention were examined for their ADCC activities against a lung adenocarcinoma cell line ABC-1 and a gastric cancer cell line AGS by a chromium release method. The ABC-1 or AGS cells were inoculated to a 96-well plate and attached to the wells. Then, chromium-51 was added to the wells, and the cells were cultured for several hours. After removal of the culture solution, the cells were washed with a culture solution, and a fresh culture solution was then added thereto. Subsequently each antibody was added to the wells, and effector cells (recombinant NK-92 (ATCC, CRL-2407) cells forced to express chimeric proteins containing a mouse Fc-gamma receptor 3 (NM_010188) extracellular region and human gamma chain (NM_004106) transmembrane and intracellular regions; Japanese Patent Application No. 2007-20155) were added to each well in an amount approximately 5 times that of the target cells. The plate was left standing at 37° C. for 4 hours in a 5% $CO_2$ incubator. The plate thus left standing was centrifuged, and a predetermined amount of the supernatant was collected from each well. The radioactivity thereof was measured using a gamma counter Wallac 1480, and the rate of specific chromium release (%) was determined according to the following formula:

Rate of specific chromium release (%)=$(A-C) \times 100/ (B-C)$, wherein

A represents radioactivity from each well; B represents an average of radioactivity released to medium after cell lysis with Nonidet P-40 at a final concentration of 1%; and C represents an average of radioactivity derived from only a medium added.

Figure 8:
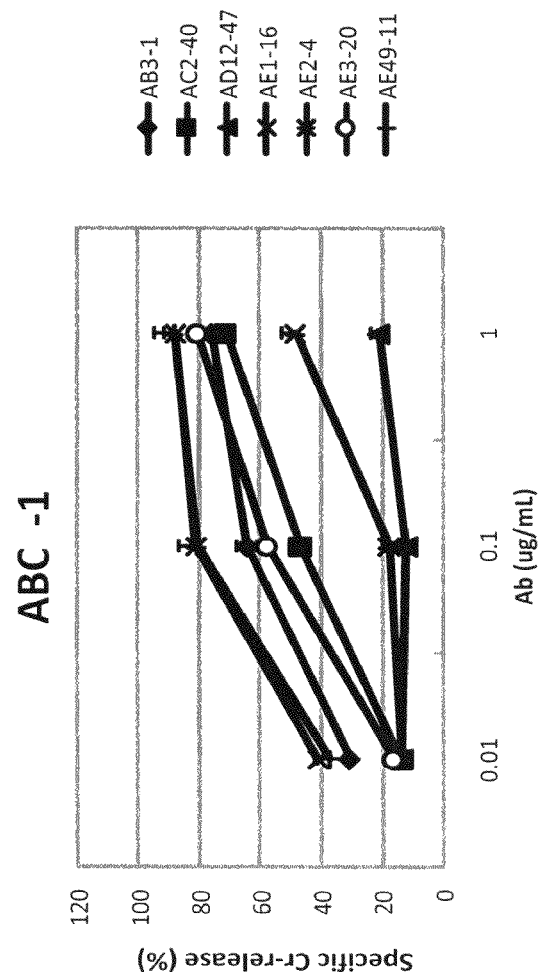
FIG. 8 shows the ADCC activities of anti-human CLDN6 antibodies against a lung adenocarcinoma cell line ABC-1.
Figure 9:
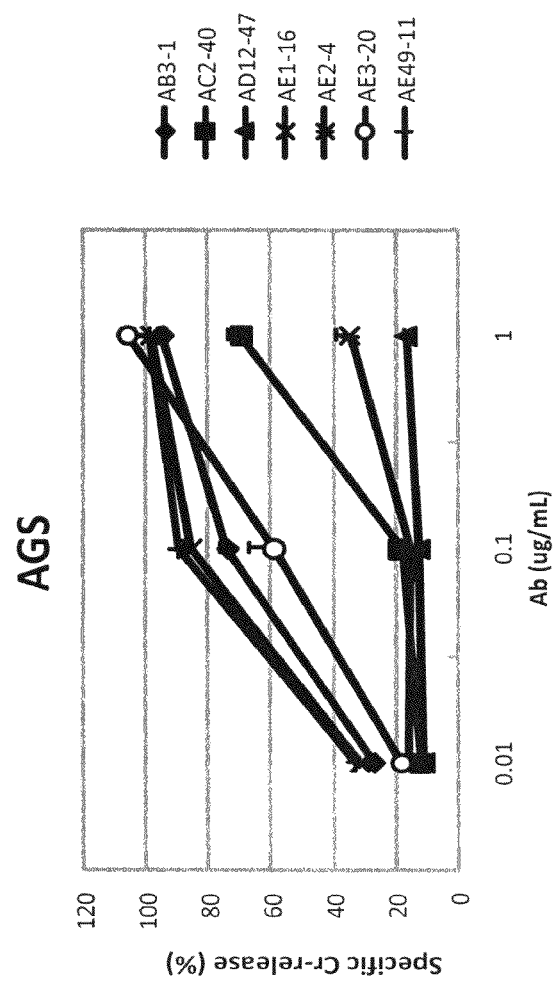
FIG. 9 shows the ADCC activities of anti-human CLDN6 antibodies against a gastric cancer cell line AGS.

As a result, of the anti-human CLDN6 monoclonal antibodies of the present invention used in the test, particularly, AB3-1, AE1-16, AE49-11, AE3-20, and AC2-40 induced very strong ADCC activity against ABC-1 and AGS, as shown in FIGS. 8 and 9. These results demonstrated that the human CLDN6-targeting antibody treatment of tumors is very useful.

3-7. Assay on Complement-Dependent Cytotoxicity (CDC) Activities of Anti-Human CLDN6 Antibodies The anti-human CLDN6 monoclonal antibodies were examined for their CDC activities against a lung adenocarcinoma cell line ABC-1 by a chromium release method. The ABC-1 cells were inoculated to a 96-well plate and attached to the wells. Then, chromium-51 was added to the wells, and the cells were cultured for several hours. After removal of the culture solution, the cells were washed with a culture solution, and a fresh culture solution was then added thereto. Subsequently, each anti-human CLDN6 monoclonal antibody of the present invention (AB3-1, AC2-40, AD12-47, AE1-16, AE2-4, AE3-20, and AE49-11) or a control mouse IgG1 antibody (Cat. No. 553453, BD Biosciences Pharmingen) was added at a final concentration of 10 μg/mL to the wells. Subsequently, infant rabbit complements (Cat. No. CL3441, Cedarlane Laboratories Ltd.) were added thereto at a final concentration of 25%, 5%, or 1%. The plate was left standing at 37° C. for 1.5 hours in a 5% $CO_2$ incubator. The plate thus left standing was centrifuged, and a predetermined amount of the supernatant was collected from each well. The radioactivity thereof was measured using a gamma counter Wallac 1480, and the rate of specific chromium release (%) was determined in the same way as in the preceding paragraph 3-6.

Figure 10:
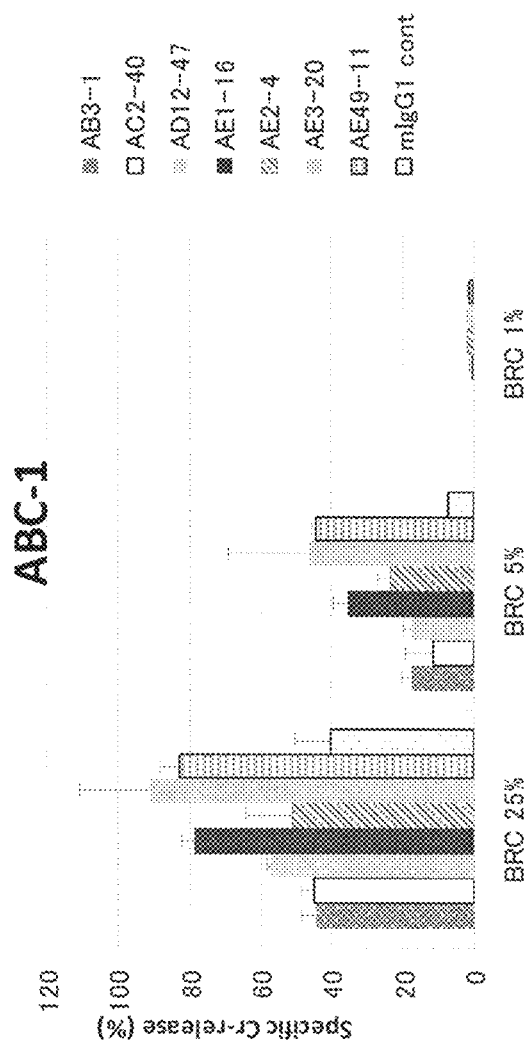
FIG. 10 shows the CDC activities of anti-human CLDN6 antibodies against a lung adenocarcinoma cell line ABC-1.

As a result, of the anti-human CLDN6 monoclonal antibodies of the present invention used in the test, particularly, AE1-16, AE3-20, and AE49-11 induced strong CDC activity, as shown in FIG. 10. On the other hand, the mouse IgG1 antibody used as a control exhibited no CDC activity.

3-8. Evaluation on Antitumor Effects of Anti-Human CLDN6 Antibodies Using Mab-ZAP Whether or not immunotoxin targeting human CLDN6 can exhibit antitumor activity was evaluated using Mab-ZAP (Advanced Targeting Systems). The Mab-ZAP was goat anti-moue IgG labeled with saporin. The saporin is a proteinous toxin that acts through the inhibition mechanism of ribosomal protein synthesis. Not all antibodies are suitable for preparing immunotoxin. It is known that some antibodies have strong efficacy as immunotoxin, and others do not (Non-Patent Document 9; Kohls and Lappi, BioTechniques 2000, 28 (1): 162). Thus, the 18 types of anti-human CLDN6 antibodies obtained this time were evaluated for their potentials as immunotoxin using Mab-ZAP.

A lung adenocarcinoma cell line ABC-1 and a gastric cancer cell line AGS were used as target cancer cell lines. The ABC-1 cells were inoculated at a concentration of $5 \times 10^3$ cells/100 μL/well to a 96-well plate on day 0. On day 1, those various types of anti-human CLDN6 monoclonal antibodies were added thereto at each final concentration of 100 ng/200 μL medium/well or 0 ng/200 μL medium/well. Subsequently, Mab-ZAP was added thereto at a final concentration of 100 ng/200 μL medium/well. The cells were cultured at 37° C. in a $CO_2$ incubator. On day 9, a live cell assay reagent SF (Nacalai Tesque, Inc.) was added at a concentration of 20 μL/well, and the cells were cultured at 37° C. for 30 minutes in a $CO_2$ incubator. Then, the absorbance at 450 nm to 650 nm was measured. The AGS cells were inoculated at a concentration of $1 \times 10^3$ cells/100 μL/well to a 96-well plate on day 0. On day 1, those various types of anti-human CLDN6 monoclonal antibodies were added thereto at each final concentration of 100 ng/200 μL medium/well or 0 ng/200 μL medium/well. Subsequently, Mab-ZAP was added thereto at a final concentration of 100 ng/200 μL medium/well. The cells were cultured at 37° C. in a $CO_2$ incubator. On day 7, a live cell assay reagent SF (Nacalai Tesque, Inc.) was added at a concentration of 20 μL/well, and the cells were cultured at 37° C. for 30 minutes in a $CO_2$ incubator. hen, the absorbance at 450 nm to 650 nm was measured.

Figure 11:
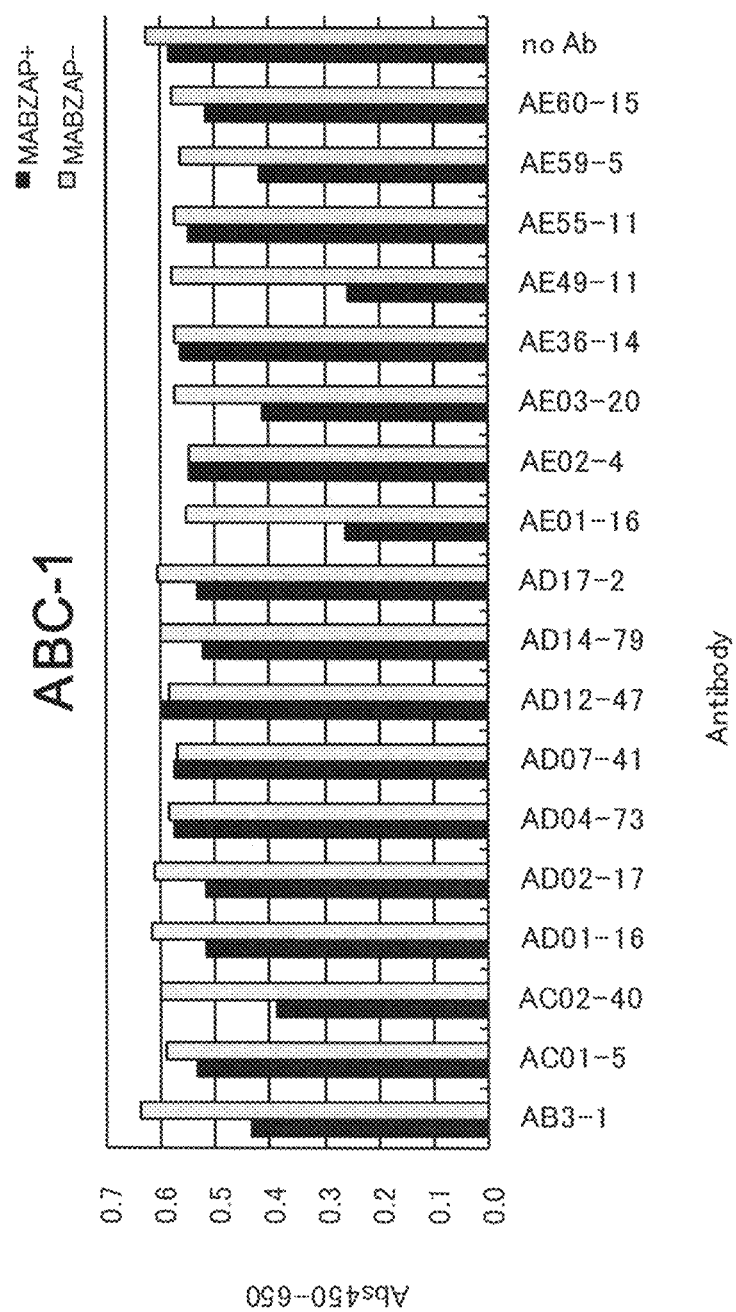
FIG. 11 shows the antitumor effects of anti-human CLDN6 monoclonal antibodies on a lung adenocarcinoma cell line ABC-1 using Mab-ZAP.
Figure 12:
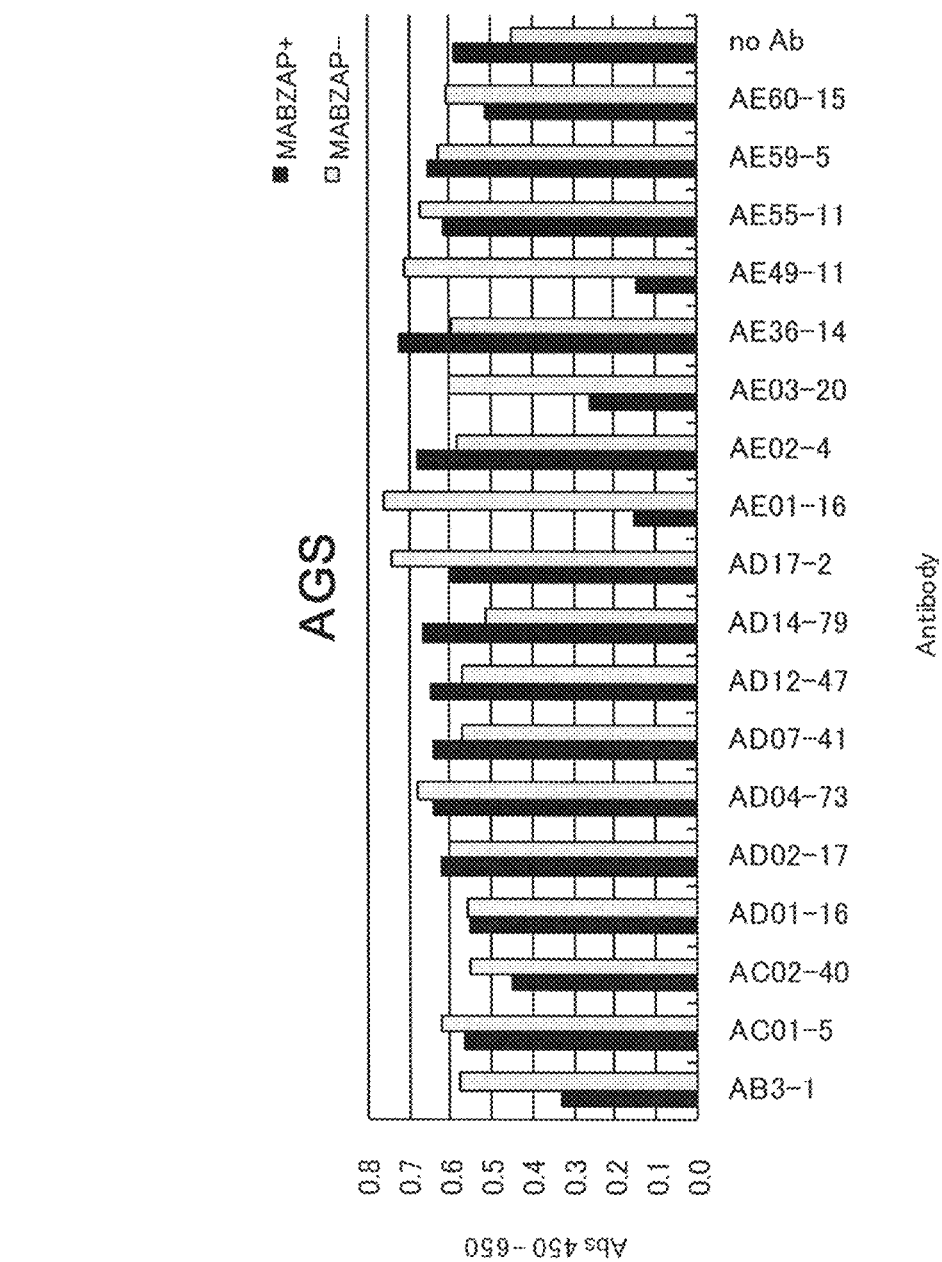
FIG. 12 shows the antitumor effects of anti-human CLDN6 monoclonal antibodies on a gastric cancer cell line AGS using Mab-ZAP.
Figure 13:
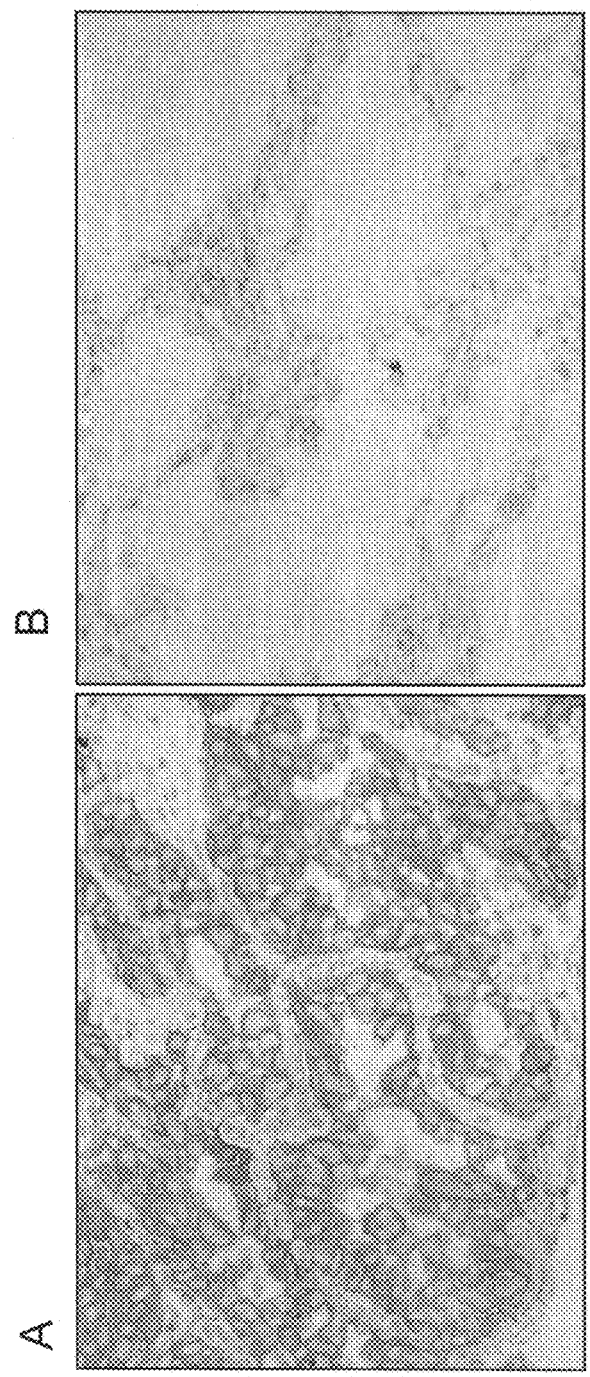
FIG. 13 shows immunostaining results obtained using goat anti-CLDN6 polyclonal antibodies (Santa Cruz Biotechnology, Inc., sc-17669) (A: tumor (lung adenocarcinoma) tissue, B: non-tumor tissue)
Figure 14:
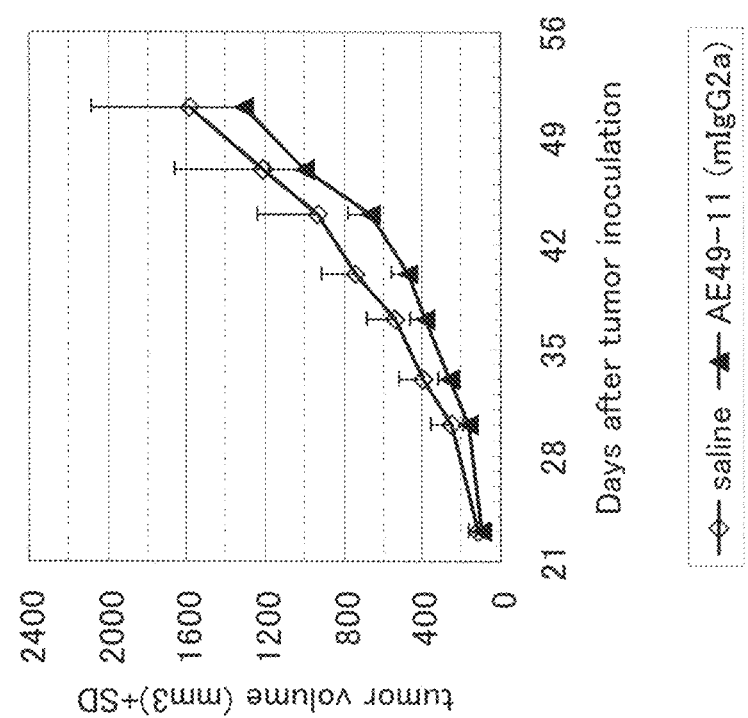
FIG. 14 shows results of evaluating the antitumor activity of an AE49-11 antibody in subcutaneous PA-1 implantation models.
Figure 15:
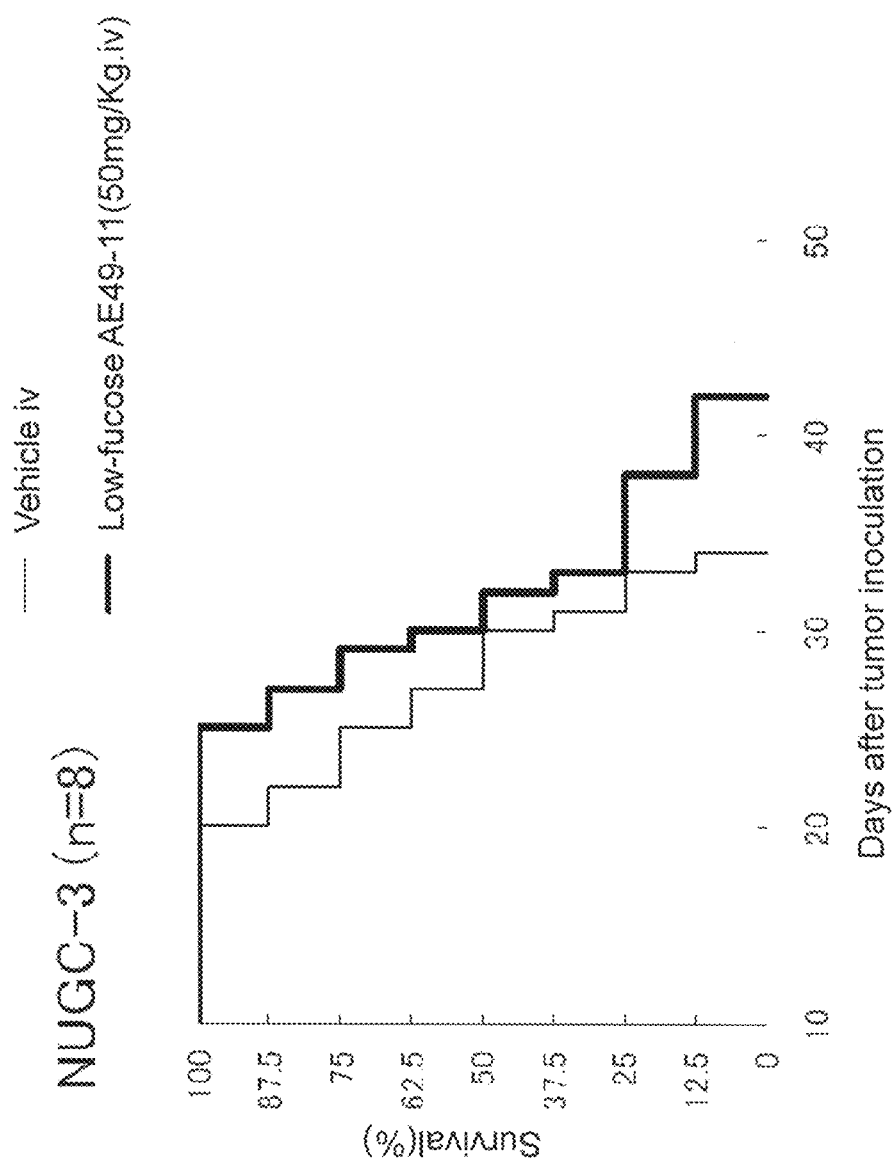
FIG. 15 shows results of evaluating the antitumor activity of the AE49-11 antibody in subcutaneous NUGC-3 implantation models (thin line: vehicle iv, thick line: low-fucose AE49-11 (50 mg/kg, iv)).

The results as to ABC-1 and AGS are shown in FIGS. 11 and 12, respectively. Antitumor effect was observed neither in the Mab-ZAP alone nor in the antibody alone, whereas the AE1-16 or AE49-11 antibody in the presence of Mab-ZAP was observed to have very strong antitumor effect on ABC-1 and AGS.

These results demonstrated that the immunotoxin targeting human CLDN6 is very useful as an antitumor agent.

Example 4

Gene Sequence Determination of Variable Regions of Anti-Human CLDN6 Antibodies

Of the anti-human CLDN6 antibodies obtained this time, 3 types of antibodies which had strong ADCC, CDC, and anti-tumor activity as immunotoxin in the presence of Mab-ZAP were selected (AB3-1, AE1-16, AE49-11, and AE3-20) based on the results described above, and the nucleic acid and amino acid sequences of their variable regions were determined. The hybridomas producing each antibody were cultured, and total RNA was purified from $1 \times 10^6$ cells using RNeasy (QIAGEN). 1 μg of the purified total RNA, SMART RACE cDNA Amplification Kit (Clontech Laboratories, Inc.), and synthetic oligonucleotide MHC-IgG1 (SEQ ID NO: 7) complementary to a mouse IgG1 constant region sequence, synthetic oligonucleotide MHC-IgG2b (SEQ ID NO: 8) complementary to a mouse IgG2b constant region sequence, or synthetic oligonucleotide mCKappaR (SEQ ID NO: 9) complementary to a mouse κ chain constant region nucleotide sequence were used to PCR-amplify sequences from a position corresponding to the above-described oligonucleotide sequence of the H or L chain constant region to the 5'-end in the cDNAs of these 3 types of antibodies. Each amplified fragment was cloned into pTA2 vectors (TOYOBO CO., LTD.), and the cDNA sequences were determined. The nucleotide and amino acid sequences of the AB3-1 H chain variable region are shown in SEQ ID NOs: 10 and 11, respectively; the nucleotide and amino acid sequences of the AB3-1 L chain variable region are shown in SEQ ID NOs: 12 and 13, respectively; the nucleotide and amino acid sequences of the AE1-16 H chain variable region are shown in SEQ ID NOs: 14 and 15, respectively; the nucleotide and amino acid sequences of the AE1-16 L chain variable region are shown in SEQ ID NOs: 16 and 17, respectively; the nucleotide and amino acid sequences of the AE49-11 H chain variable region are shown in SEQ ID NOs: 18 and 19, respectively; the nucleotide and amino acid sequences of the AE49-11 L chain variable region are shown in SEQ ID NOs: 20 and 21, respectively; the nucleotide and amino acid sequences of the AE3-20 H chain variable region are shown in SEQ ID NOs: 36 and 37, respectively; and the nucleotide and amino acid sequences of the AE3-20 L chain variable region are shown in SEQ ID NOs: 38 and 39, respectively.

Moreover, the CDR amino acid sequences of these variable regions are shown in Table below.

TABLE 1

| Antibody | | | Amino acid sequence | SEQ ID NO |
|---|---|---|---|---|
| AB3-1 | H chain | CDR1 | GYTMN | 24 |
| | | CDR2 | LINPYNGGISYNQKFKD | 25 |
| | | CDR3 | DYRYEGFDY | 26 |
| | L chain | CDR1 | TASSVVISTYLH | 27 |
| | | CDR2 | STSNLAS | 28 |
| | | CDR3 | HQYHRSPWT | 29 |
| AE1-16, AE49-11 | H chain | CDR1 | GYFMN | 30 |
| | | CDR2 | RINPYNGDTFYNQKFKG | 31 |
| | | CDR3 | VLFLDFDDPYLMDY | 32 |
| | L chain | CDR1 | RATSNVKYMY | 33 |
| | | CDR2 | YTSNLAS | 34 |
| | | CDR3 | QQFTSSPST | 35 |
| AE3-20 | H chain | CDR1 | SYTMS | 40 |
| | | CDR2 | TISSGGGRTYYPDSVKG | 41 |
| | | CDR3 | GDYRYDGFAY | 42 |
| | L chain | CDR1 | RASENIDSYLA | 43 |
| | | CDR2 | ASTLLVD | 44 |
| | | CDR3 | QHYYSIPYT | 45 |

Example 5

Evaluation on Avidities of Anti-Human CLDN6 Monoclonal Antibodies for Human CLDN1, CLDN3, CLDN4, and CLDN9 Molecules The 4 types of anti-human CLDN6 monoclonal antibodies (AB3-1, AE1-16, AE49-11, and AE3-20) whose variable region amino acid sequences were determined in [Example 4] were evaluated for their avidities for human CLDN1, CLDN3, CLDN4, and CLDN9 molecules by flow cytometry at adjusted antibody concentrations using prepared Ba/F3 cell lines forced to express each molecule.

Cells were suspended at a concentration of $1 \times 10^5$ cells in a FACS buffer (0.5% BSA, 1×PBS (−), 0.1% $NaN_3$), and the cell suspension was dispensed into a U-bottom 96-well plate (FALCON 353910). Each antibody was added thereto at final concentrations of 10, 2, 0.4, 0.08, and 0 μg/mL, then mixed, and incubated at 4° C. for 1 hour. After centrifugation, the reaction solution was removed by aspiration, and the cells were washed by the addition of 200 uL/well FACS buffer. Then, FITC-labeled Goat F(ab')$_2$ Fragment Anti-mouse IgG (Fcγ) (BECKMAN COULTER, Inc.) was diluted 100-fold with a FACS buffer and added as secondary antibodies to the cells. The cells were incubated at 4° C. for 30 minutes, then washed with the same FACS buffer as above, and suspended in 100 uL of a FACS buffer containing propidium iodide (SIGMA-ALDRICH CORP.) at a concentration of 10 μg/mL. The cell suspension was subjected to flow cytometry.

In the flow cytometry, a gate was constructed for a live cell population in a dot plot of an X axis: forward scatter against a Y axis: side scatter and a dot plot of an X axis: forward scatter against a Y axis: propidium iodide fluorescence (FL-3).

As shown in Table 2, the antibody AE3-20 of the present invention was an antibody almost specifically binding to human CLDN6. The AE1-16 and the AE49-11 were antibodies cross-reacting moderately with human CLDN9 and weakly with human CLDN4. The AB3-1 was an antibody cross-reacting with human CLDN9.

TABLE 2

| | hCLDN6 | hCLDN9 | hCLDN4 | hCLDN3 | hCLDN1 |
|---|---|---|---|---|---|
| AE3-20 | +++ | +− | − | − | − |
| AE1-16 | +++ | ++ | + | − | − |
| AE49-11 | +++ | ++ | + | − | − |
| AB3-1 | ++ | ++ | − | − | − |

Example 6

Detection of CLDN6 in Lung Adenocarcinoma Tissues Using Immunohistochemical Staining CLDN6 protein expression in lung adenocarcinoma tissues and its localization on cancer cell membrane were confirmed by immunohistochemical staining. In the immunohistochemical staining, CLDN6 transcripts were first quantified by real-time PCR using total RNA extracted from the clinical tissues of lung adenocarcinoma, and cases highly expressing CLDN6 transcripts were used. Frozen sections were fixed in 4% PFA and then immunohistochemically stained by a general LSAB method using Ventana HX Discovery System (Ventana Medical Systems, Inc.). In the immunohistochemical staining, goat anti-CLDN6 polyclonal antibodies (Santa Cruz Biotechnology, Inc. Code No. sc-17669 Lot. H2605) were adjusted to 12.5 μg/mL and used as primary antibodies. As a result, in the tumor tissues of lung adenocarcinoma, positive response was observed in the cell membranes and cytoplasms. On the other hand, in non-tumor tissues, positive response was observed in the macrophages, type II pulmonary epithelia, and bronchiolar epithelia, all of which were however stained with slight intensity. Furthermore, the positive response of cell membranes, which was observed in the tumor tissues, was not observed in the non-tumor tissues. The cell membranes of the lung tumor tissues were stained with higher intensity than that of the normal lung tissues. The detection of expression at a protein level in the cell membranes of human tumor tissues was shown for the first time by the present invention.

Example 7

Evaluation on Antitumor Activity of Anti-CLDN6 Antibody

Evaluation on Antitumor Activity of AE49-11 Antibody
The AE49-11 antibody was classified as IgG2b subclass. Since the previous studies have reported that IgG2a has stronger ADCC activity (Non-Patent Documents [10] and [11]), expression vectors were constructed, which expressed an AE49-11 antibody having the antibody Fc region converted to an IgG2a Fc region (this antibody was designated as "AE49-11/mIgG2a"; H chain amino acid sequence: SEQ ID NO: [52] and L chain amino acid sequence: SEQ ID NO: [53]) for the purpose of enhancing efficacy. This antibody was expressed in CHO-DG44 cells and purified. This AE49-11/mIgG2a antibody was confirmed by flow cytometry to have avidity almost equivalent to that of the original IgG2b antibody. Using this antibody, in-vivo anti-tumor experiments were conducted as shown below.

(1) Subcutaneous PA-1 Implantation Models

PA-1 cells were adjusted to $5 \times 10^7$ cells/ml with Hanks' Balanced Salt Solution (HBSS) and subcutaneously implanted at a dose of 200 µl into the abdominal region of each SCID mouse (9-week-old female, Charles River Laboratories Japan, Inc.) that received, on the previous day, intraperitoneal administration of 100 µl of anti-asialo GM1 antibodies (Wako Pure Chemical Industries, Ltd.; 1 vial was dissolved in 1 ml of injectable distilled water and then supplemented with 4 ml of saline). From 23 days after the implantation, the AE49-11/mIgG2a antibody was administrated through the tail vein once a week for 4 weeks. The antibody was adjusted to 5 mg/ml with saline and then administered at a dose of 50 mg/kg. Saline (vehicle) was administered as a negative control in the same way as above. The test was conducted with each group involving 5 mice. The antitumor activity was evaluated based on tumor volumes. The tumor volumes (mm3), the amount of change in tumor volume, and the tumor growth inhibitory effect (%) were calculated as follows:

Tumor volume (mm3)=major axis of tumor×minor axis of tumor×minor axis of tumor×½

Amount of change in tumor volume (mm3)=tumor volume at the time of measurement−tumor volume at the start of administration Tumor growth inhibitory rate (%)={1−(average of amount of change in tumor volume of drug administration group/average of amount of change in tumor volume of vehicle administration group)}×100

The test results showed that the AE49-11/mIgG2a antibody tends to inhibit tumor growth in the 50 mg/kg administration group compared in the vehicle administration group. Its tumor growth inhibitory rates after 1, 2, 3, and 4 weeks into administration were 49.5%, 31.1%, 29.9%, and 17.9%, respectively, showing that the antibody tends to have strong inhibitory effect on tumor growth at the early stage of administration.

(2) Subcutaneous NUGC-3 Implantation Models

Subsequently, efficacy was studied in subcutaneous NUGC-3 implantation models. To conduct the efficacy test using the models, the AE49-11/mIgG2a antibody was expressed in fucose transporter-knockout CHO-DXB11S cells, then purified (the obtained antibody is referred to as a low-fucose-type AE49-11/mIgG2a antibody), and used in the efficacy test.

NUGC-3 cells were adjusted to $5 \times 10^7$ cells/ml with Hanks' Balanced Salt Solution (HBSS) and subcutaneously implanted at a dose of 200 µl into the abdominal region of each SCID mouse (12-week-old female, Charles River Laboratories Japan, Inc.). 11 days after the implantation, the mice were divided into two groups depending on tumor volumes and body weights. 11, 17, and 24 days after the implantation, the low-fucose-type AE49-11/mIgG2a antibody or a vehicle was administrated through the tail vein. The antibody was adjusted to 5 mg/ml with a vehicle and then administered at a dose of 50 mg/kg. The vehicle used was a solution obtained by buffer-substituting a mixed solution (containing 100 mM Glycine (pH 2.7) and 1 M Tris-HCl (pH 9.0) in a ¹⁄₁₀ amount with respect thereto) using a PD-10 column with D-PBS (−) as an elution buffer and sterilizing the resulting solution through a 0.22-µm filter.

The test was conducted with each group involving 8 mice. The antitumor activity was evaluated based on life-prolonging effect.

The test results showed that the low-fucose-type AE49-11/mIgG2a has the life-prolonging effect compared with the vehicle administration group.

It was thus suggested that the anti-CLDN6 antibody is likely to exhibit antitumor activity in human clinical application.

INDUSTRIAL APPLICABILITY

An anti-CLDN6 antibody of the present invention is useful as an antibody drug, particularly, as a cell growth inhibitor and an anticancer agent.

All publications, patents, and patent applications cited herein are incorporated herein by reference in their entirety.

The invention claimed is:

1. An isolated monoclonal antibody selected from the group consisting of (a) and (b):
   (a) an antibody comprising a heavy chain variable region having CDR1 having the amino acid sequence represented by SEQ ID NO: 40, CDR2 having the amino acid sequence represented by SEQ ID NO: 41, and CDR3 having the amino acid sequence represented by SEQ ID NO: 42 and comprising a light chain variable region having CDR1 having the amino acid sequence represented by SEQ ID NO: 43, CDR2 having the amino acid sequence represented by SEQ ID NO: 44, and CDR3 having the amino acid sequence represented by SEQ ID NO: 45; and
   (b) an antibody which blocks the binding of the antibody of (a) to CLDN6,
   wherein said antibody selected from the group consisting of (a) and (b) has cytotoxicity, and has 50% or less avidity for CLDN9 as set forth in SEQ ID NO: 48 compared with its avidity for CLDN6.

2. The isolated monoclonal antibody according to claim 1, which has ADCC activity.

3. The isolated monoclonal antibody according to claim 1, which has CDC activity.

4. The isolated monoclonal antibody according to claim 1, which is conjugated with a cytotoxic substance.

5. The isolated monoclonal antibody according to claim 1, which has 30% or less avidity for CLDN9 as set forth in SEQ ID NO:48 compared with its avidity for CLDN6.

6. The isolated monoclonal antibody according to claim 1, which has 10% or less avidity for CLDN9 as set forth in SEQ ID NO:48 compared with its avidity for CLDN6.

7. A pharmaceutical composition for treating cancer, comprising the isolated monoclonal antibody of claim 1.

8. The pharmaceutical composition according to claim 7, wherein the cancer is a cancer highly expressing CLDN6.

9. The pharmaceutical composition according to claim 7, wherein the cancer is lung adenocarcinoma, gastric cancer, or ovarian cancer.

* * * * *

SEQUENCE LISTING

<160> NUMBER OF SEQ ID NOS: 53

<210> SEQ ID NO 1
<211> LENGTH: 27
<212> TYPE: DNA
<213> ORGANISM: Artificial
<220> FEATURE:
<223> OTHER INFORMATION: PCR primer

<400> SEQUENCE: 1
catggcctct gccggaatgc agatcct                27

<210> SEQ ID NO 2
<211> LENGTH: 27
<212> TYPE: DNA
<213> ORGANISM: Artificial
<220> FEATURE:
<223> OTHER INFORMATION: PCR primer

<400> SEQUENCE: 2
cccaaagctg ttgggcactg ccacttc                                27

<210> SEQ ID NO 3
<211> LENGTH: 35
<212> TYPE: DNA
<213> ORGANISM: Artificial
<220> FEATURE:
<223> OTHER INFORMATION: PCR primer

<400> SEQUENCE: 3
gctaagctta ccatggcctc tgccggaatg cagat                       35

<210> SEQ ID NO 4
<211> LENGTH: 35
<212> TYPE: DNA
<213> ORGANISM: Artificial
<220> FEATURE:
<223> OTHER INFORMATION: PCR primer

<400> SEQUENCE: 4
gcagctagcg acgtaattct tggtagggta ctcag                       35

<210> SEQ ID NO 5
<211> LENGTH: 38
<212> TYPE: DNA
<213> ORGANISM: Artificial
<220> FEATURE:
<223> OTHER INFORMATION: PCR primer

<400> SEQUENCE: 5
ccggaattcc caccatggcc tctgccggaa tgcagatc                    38

<210> SEQ ID NO 6
<211> LENGTH: 35
<212> TYPE: DNA
<213> ORGANISM: Artificial
<220> FEATURE:
<223> OTHER INFORMATION: PCR primer

<400> SEQUENCE: 6
gcggccgctc agacgtaatt cttggtaggg tactc                       35

<210> SEQ ID NO 7
<211> LENGTH: 21
<212> TYPE: DNA
<213> ORGANISM: Mus musculus

<400> SEQUENCE: 7
gggccagtgg atagacagat g                                      21

<210> SEQ ID NO 8
<211> LENGTH: 24
<212> TYPE: DNA
<213> ORGANISM: Mus musculus

<400> SEQUENCE: 8
caggggccag tggatagact gatg                                   24

<210> SEQ ID NO 9
<211> LENGTH: 27
<212> TYPE: DNA
<213> ORGANISM: Mus musculus

<400> SEQUENCE: 9
ggcacctcca gatgttaact gctcact                                27

<210> SEQ ID NO 10
<211> LENGTH: 354
<212> TYPE: DNA
<213> ORGANISM: Mus musculus

<400> SEQUENCE: 10
gaggtccagc tgcaacagtc tggacctgag ttggtgaagc ctggaggttc aatgaagata    60
tcctgcaagg cttctggcta ctcattcact ggctacacca tgaactgggt gaagcagagc   120
catggaaaga accttgagtg gattggactt attaatcctt acaatggcgg tattagttac   180
aaccagaaat tcaaagacaa ggccacacta actatggaca gtcatccag cacagcctac    240 atggagctcc tcagtctgac atctgaggac tctgcaatct atttctgtgc aagagactat   300
aggtacgagg gctttgatta ctggggccaa gggactctgg tcactgtctc tgca         354

<210> SEQ ID NO 11
<211> LENGTH: 118
<212> TYPE: PRT
<213> ORGANISM: Mus musculus

<400> SEQUENCE: 11

Glu Val Gln Leu Gln Gln Ser Gly Pro Glu Leu Val Lys Pro Gly Gly
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Ile Ser Tyr Asn Gln Lys Phe
    50                  55                  60

Lys Asp Lys Ala Thr Leu Thr Met Asp Lys Ser Ser Ser Thr Ala Tyr
65                  70                  75                  80

Met Glu Leu Leu Ser Leu Thr Ser Glu Asp Ser Ala Ile Tyr Phe Cys
                85                  90                  95

Ala Arg Asp Tyr Arg Tyr Glu Gly Phe Asp Tyr Trp Gly Gln Gly Thr
            100                 105                 110

Leu Val Thr Val Ser Ala
        115

<210> SEQ ID NO 12
<211> LENGTH: 324
<212> TYPE: DNA
<213> ORGANISM: Mus musculus

<400> SEQUENCE: 12
caaattgttc tcacccagtc tccagcaatc atgtctgcat ctctagggga acgggtcacc    60
atgacctgta ctgccagttc agttgtaatt tccacttact gcactggta ccagcagaag    120 ccaggatcct cccccaaact ctggatttat agcacatcca acctggcttc tggagtccca   180
gttcgcttca gtggcagtgg gtctgggacc tcttactctc tcacaatcag cagcatggag   240
gctgaagatg ctgccactta ttactgccac cagtatcatc gttccccgtg gacgttcggt   300
ggaggcacca agctggaaat caaa                                          324

<210> SEQ ID NO 13
<211> LENGTH: 108

<212> TYPE: PRT
<213> ORGANISM: Mus musculus

<400> SEQUENCE: 13

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Val Val Ile Ser Thr
            20                  25                  30

Tyr Leu His Trp Tyr Gln Gln Lys Pro Gly Ser Pro Lys Leu Trp
        35                  40                  45

Ile Tyr Ser Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Trp Thr Phe Gly Gly Gly Thr Lys Leu Glu Ile Lys
            100                 105

<210> SEQ ID NO 14
<211> LENGTH: 369
<212> TYPE: DNA
<213> ORGANISM: Mus musculus

<400> SEQUENCE: 14
gaggttcagc tgcagcagtc tggacctgag ctggtgaagc ctggggcttc agtgaagata    60
tcctgcaagg cttctggtta ctcattact ggctacttta tgaactgggt gaaacagagc   120
catggaaaga gccttgagtg gattggacgt attaatcctt acaatggtga cactttctac   180
aaccagaagt tcaagggcaa ggccacatta actgtagaca atcctctaa tacagcccac   240
atggagctcc ggagcctgac atctgaggac tctgcagtct attattgtgc aagagtcctc   300
ttccttgatt tcgacgaccc ctatcttatg gactattggg gtcaaggaac ctcagtcacc   360
gtctcctca                                                           369

<210> SEQ ID NO 15
<211> LENGTH: 123
<212> TYPE: PRT
<213> ORGANISM: Mus musculus

<400> SEQUENCE: 15

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Asn Thr Ala His
65                  70                  75                  80

Met Glu Leu Arg Ser Leu Thr Ser Glu Asp Ser Ala Val Tyr Tyr Cys
                85                  90                  95

Ala Arg Val Leu Phe Leu Asp Phe Asp Asp Pro Tyr Leu Met Asp Tyr
            100                 105                 110

Trp Gly Gln Gly Thr Ser Val Thr Val Ser Ser
        115                 120

<210> SEQ ID NO 16
<211> LENGTH: 318
<212> TYPE: DNA
<213> ORGANISM: Mus musculus

<400> SEQUENCE: 16

```
gaaaatgtgc tcacccagtc tccagcaatc atgtctgcaa ctcttgggga gaaggtcacc      60
atgagctgca gggccaccct caaatgtaaag tacatgtact ggtaccagca gaagtcaggt     120
gcctccccca aactatggat ttattacaca tccaacctgg cttctggagt cccagctcgc     180
ttcagtggca gtgggtctgg gacctcttat tctctcacaa tcagcagcgt ggaggctgca     240
gatgctgcca cttattactg ccagcagttt actagttccc catccacgtt cggtgctggg     300
accaagctgg agctgaaa                                                   318
```

<210> SEQ ID NO 17
<211> LENGTH: 106
<212> TYPE: PRT
<213> ORGANISM: Mus musculus

<400> SEQUENCE: 17

```
Glu Asn Val Leu Thr Gln Ser Pro Ala Ile Met Ser Ala Thr Leu Gly
1               5                   10                  15
Glu Lys Val Thr Met Ser Cys Arg Ala Thr Ser Asn Val Lys Tyr Met
            20                  25                  30
Tyr Trp Tyr Gln Gln Lys Ser Gly Ala Ser Pro Lys Leu Trp Ile Tyr
        35                  40                  45
Tyr Thr Ser Asn Leu Ala Ser Gly Val Pro Ala Arg Phe Ser Gly Ser
    50                  55                  60
Gly Ser Gly Thr Ser Tyr Ser Leu Thr Ile Ser Ser Val Glu Ala Ala
65                  70                  75                  80
Asp Ala Ala Thr Tyr Tyr Cys Gln Gln Phe Thr Ser Ser Pro Ser Thr
                85                  90                  95
Phe Gly Ala Gly Thr Lys Leu Glu Leu Lys
            100                 105
```

<210> SEQ ID NO 18
<211> LENGTH: 369
<212> TYPE: DNA
<213> ORGANISM: Mus musculus

<400> SEQUENCE: 18

```
gaggttcagc tgcagcagtc tggacctgag ctggtgaagc ctggggcttc agtgaagata      60
tcctgcaagg cttctggtta ctcatttact ggctacttta tgaactgggt gaagcagagc     120
catggaaaga gccttgagtg gattggacgt attaatcctt acaatggtga tactttctac     180
aaccagaagt tcaagggcaa ggccacatta actgtagaca atcctctag cacagcccac      240
atggagctcc ggagcctgac atctgaggac tctgcagtct attattgtgc aagagtcctc     300
ttccttgatt tcgacgaccc ctatcttatg gactattggg gtcaaggaac ctcagtcacc     360
gtctcctca                                                             369
```

<210> SEQ ID NO 19
<211> LENGTH: 123
<212> TYPE: PRT
<213> ORGANISM: Mus musculus

<400> SEQUENCE: 19

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Thr Ala His
65                  70                  75                  80

Met Glu Leu Arg Ser Leu Thr Ser Glu Asp Ser Ala Val Tyr Tyr Cys
                85                  90                  95

Ala Arg Val Leu Phe Leu Asp Phe Asp Asp Pro Tyr Leu Met Asp Tyr
                100                 105                 110

Trp Gly Gln Gly Thr Ser Val Thr Val Ser Ser
            115                 120
```

<210> SEQ ID NO 20
<211> LENGTH: 318
<212> TYPE: DNA
<213> ORGANISM: Mus musculus

<400> SEQUENCE: 20

```
gaaaatgtgc tcacccagtc tccagcaatc atgtctgcaa ctcttgggga gaaggtcacc    60
atgagctgca gggccaccte aaatgtaaag tacatgtact ggtaccagca gaagtcaggt   120
gcctccccca aactatggat ttattacaca tccaacctgg cttctggagt cccagctcgc   180
ttcagtggca gtgggtctgg gacctcttat tctctcacaa tcagcagcgt ggaggctgca   240
gatgctgcca cttattactg ccagcagttt actagttccc catccacgtt cggtgctggg   300
accaagctgg agctgaaa                                                 318
```

<210> SEQ ID NO 21
<211> LENGTH: 106
<212> TYPE: PRT
<213> ORGANISM: Mus musculus

<400> SEQUENCE: 21

```
Glu Asn Val Leu Thr Gln Ser Pro Ala Ile Met Ser Ala Thr Leu Gly
1               5                   10                  15

Glu Lys Val Thr Met Ser Cys Arg Ala Thr Ser Asn Val Lys Tyr Met
            20                  25                  30

Tyr Trp Tyr Gln Gln Lys Ser Gly Ala Ser Pro Lys Leu Trp Ile Tyr
        35                  40                  45

Tyr Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Val Glu Ala Ala
65                  70                  75                  80

Asp Ala Ala Thr Tyr Tyr Cys Gln Gln Phe Thr Ser Ser Pro Ser Thr
                85                  90                  95

Phe Gly Ala Gly Thr Lys Leu Glu Leu Lys
                100                 105
```

<210> SEQ ID NO 22
<211> LENGTH: 220
<212> TYPE: PRT
<213> ORGANISM: homo sapiens

<400> SEQUENCE: 22

```
Met Ala Ser Ala Gly Met Gln Ile Leu Gly Val Val Leu Thr Leu Leu
1               5                   10                  15
Gly Trp Val Asn Gly Leu Val Ser Cys Ala Leu Pro Met Trp Lys Val
            20                  25                  30
Thr Ala Phe Ile Gly Asn Ser Ile Val Val Ala Gln Val Val Trp Glu
        35                  40                  45
Gly Leu Trp Met Ser Cys Val Val Gln Ser Thr Gly Gln Met Gln Cys
    50                  55                  60
Lys Val Tyr Asp Ser Leu Leu Ala Leu Pro Gln Asp Leu Gln Ala Ala
65                  70                  75                  80
Arg Ala Leu Cys Val Ile Ala Leu Leu Val Ala Leu Phe Gly Leu Leu
                85                  90                  95
Val Tyr Leu Ala Gly Ala Lys Cys Thr Thr Cys Val Glu Glu Lys Asp
            100                 105                 110
Ser Lys Ala Arg Leu Val Leu Thr Ser Gly Ile Val Phe Val Ile Ser
        115                 120                 125
Gly Val Leu Thr Leu Ile Pro Val Cys Trp Thr Ala His Ala Val Ile
    130                 135                 140
Arg Asp Phe Tyr Asn Pro Leu Val Ala Glu Ala Gln Lys Arg Glu Leu
145                 150                 155                 160
Gly Ala Ser Leu Tyr Leu Gly Trp Ala Ala Ser Gly Leu Leu Leu Leu
                165                 170                 175
Gly Gly Gly Leu Leu Cys Cys Thr Cys Pro Ser Gly Gly Ser Gln Gly
            180                 185                 190
Pro Ser His Tyr Met Ala Arg Tyr Ser Thr Ser Ala Pro Ala Ile Ser
        195                 200                 205
Arg Gly Pro Ser Glu Tyr Pro Thr Lys Asn Tyr Val
    210                 215                 220
```

<210> SEQ ID NO 23
<211> LENGTH: 1363
<212> TYPE: DNA
<213> ORGANISM: homo sapiens

<400> SEQUENCE: 23

```
atctccttcg cagtgcagct ccttcaacct cgccatggcc tctgccggaa tgcagatcct    60
gggagtcgtc ctgacactgc tgggctgggt gaatggcctg gtctcctgtg ccctgcccat   120
gtggaaggtg accgctttca tcggcaacag catcgtggtg gcccaggtgg tgtgggaggg   180
cctgtggatg tcctgcgtgg tgcagagcac cggccagatg cagtgcaagg tgtacgactc   240
actgctggcg ctgccacagg acctgcaggc tgcacgtgcc ctctgtgtca tcgccctcct   300
tgtggccctg ttcggcttgc tggtctacct tgctggggcc aagtgtacca cctgtgtgga   360
ggagaaggat tccaaggccc gcctggtgct cacctctggg attgtctttg tcatctcagg   420
ggtcctgacg ctaatccccg tgtgctggac ggcgcatgcc gtcatccggg acttctataa   480
cccccctggtg gctgaggccc aaaagcggga gctggggggcc tccctctact gggctgggc   540
ggcctcaggc cttttgttgc tgggtggggg ttgctgtgc tgcacttgcc cctcgggggg   600
gtcccagggc cccagccatt acatggcccg ctactcaaca tctgcccctg ccatctctcg   660
ggggccctct gagtacccta ccaagaatta cgtctgacgt ggaggggaat ggggctccg   720
ctggcgctag agccatccag aagtggcagt gcccaacagc tttgggatgg gttcgtacct   780
```

```
tttgtttctg cctcctgcta ttttctttt gactgaggat atttaaaatt catttgaaaa    840
ctgagccaag gtgttgactc agactctcac ttaggctctg ctgtttctca cccttggatg    900
atggagccaa agaggggatg cttgagatt ctggatcttg acatgcccat cttagaagcc    960
agtcaagcta tggaactaat gcggaggctg cttgctgtgc tggctttgca acaagacaga   1020
ctgtccccaa gagttcctgc tgctgctggg ggctgggctt ccctagatgt cactggacag   1080
ctgcccccca tcctactcag gtctctggag ctcctctctt caccccctgga aaaacaaatg  1140
atctgttaac aaaggactgc ccacctccgg aacttctgac ctctgtttcc tccgtcctga  1200
taagacgtcc accccccagg gccaggtccc agctatgtag accccgcccc cacctccaa   1260
cactgcaccc ttctgccctg ccccctcgt ctcacccct ttacactcac atttttatca   1320
aataaagcat gttttgttag tgcaaaaaaa aaaaaaaaaa aaa                    1363
```

<210> SEQ ID NO 24
<211> LENGTH: 5
<212> TYPE: PRT
<213> ORGANISM: Mus musculus

<400> SEQUENCE: 24

Gly Tyr Thr Met Asn
1               5

<210> SEQ ID NO 25
<211> LENGTH: 17
<212> TYPE: PRT
<213> ORGANISM: Mus musculus

<400> SEQUENCE: 25

Leu Ile Asn Pro Tyr Asn Gly Gly Ile Ser Tyr Asn Gln Lys Phe Lys
1               5                   10                  15
Asp

<210> SEQ ID NO 26
<211> LENGTH: 9
<212> TYPE: PRT
<213> ORGANISM: Mus musculus

<400> SEQUENCE: 26

Asp Tyr Arg Tyr Glu Gly Phe Asp Tyr
1               5

<210> SEQ ID NO 27
<211> LENGTH: 12
<212> TYPE: PRT
<213> ORGANISM: Mus musculus

<400> SEQUENCE: 27

Thr Ala Ser Ser Val Val Ile Ser Thr Tyr Leu His
1               5                   10

<210> SEQ ID NO 28
<211> LENGTH: 7
<212> TYPE: PRT
<213> ORGANISM: Mus musculus

<400> SEQUENCE: 28

Ser Thr Ser Asn Leu Ala Ser
1               5

<210> SEQ ID NO 29

```
<211> LENGTH: 9
<212> TYPE: PRT
<213> ORGANISM: Mus musculus

<400> SEQUENCE: 29

His Gln Tyr His Arg Ser Pro Trp Thr
1               5

<210> SEQ ID NO 30
<211> LENGTH: 5
<212> TYPE: PRT
<213> ORGANISM: Mus musculus

<400> SEQUENCE: 30

Gly Tyr Phe Met Asn
1               5

<210> SEQ ID NO 31
<211> LENGTH: 17
<212> TYPE: PRT
<213> ORGANISM: Mus musculus

<400> SEQUENCE: 31

Arg Ile Asn Pro Tyr Asn Gly Asp Thr Phe Tyr Asn Gln Lys Phe Lys
1               5                   10                  15

Gly

<210> SEQ ID NO 32
<211> LENGTH: 14
<212> TYPE: PRT
<213> ORGANISM: Mus musculus

<400> SEQUENCE: 32

Val Leu Phe Leu Asp Phe Asp Asp Pro Tyr Leu Met Asp Tyr
1               5                   10

<210> SEQ ID NO 33
<211> LENGTH: 10
<212> TYPE: PRT
<213> ORGANISM: Mus musculus

<400> SEQUENCE: 33

Arg Ala Thr Ser Asn Val Lys Tyr Met Tyr
1               5                   10

<210> SEQ ID NO 34
<211> LENGTH: 7
<212> TYPE: PRT
<213> ORGANISM: Mus musculus

<400> SEQUENCE: 34

Tyr Thr Ser Asn Leu Ala Ser
1               5

<210> SEQ ID NO 35
<211> LENGTH: 9
<212> TYPE: PRT
<213> ORGANISM: Mus musculus

<400> SEQUENCE: 35

Gln Gln Phe Thr Ser Ser Pro Ser Thr
1               5

<210> SEQ ID NO 36
```

<210> SEQ ID NO 36
<211> LENGTH: 357
<212> TYPE: DNA
<213> ORGANISM: Mus musculus

<400> SEQUENCE: 36

```
gaagtgaagc tggtggagtc tgggggaggc ttagtgaagc tggagggtc cctgaaactc      60
tcctgtgcag cctctggatt cactttcaat agctatacca tgtcttgggt tcgccagact     120
ccggcgaaga ggctggagtg ggtcgtaacc attagtagtg gtggaggtcg cacctactat    180
ccagacagtg tgaagggccg attcaccatc tccagagaca atgccaggaa caccctgtac    240
ctacaaatga gcagtctgag gtctgaagac acggccatgt attactgtat aaggggggac    300
tataggtacg acgggtttgc ttactgggc caggggactc tggtcactgt ctctaca       357
```

<210> SEQ ID NO 37
<211> LENGTH: 119
<212> TYPE: PRT
<213> ORGANISM: Mus musculus

<400> SEQUENCE: 37

Glu Val Lys Leu Val Glu Ser Gly Gly Gly Leu Val Lys Pro Gly Gly
1               5                  10                  15

Ser Leu Lys Leu Ser Cys Ala Ala Ser Gly Phe Thr Phe Asn Ser Tyr
            20                  25                  30

Thr Met Ser Trp Val Arg Gln Thr Pro Ala Lys Arg Leu Glu Trp Val
        35                  40                  45

Val Thr Ile Ser Ser Gly Gly Gly Arg Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
                85                  90                  95

Ile Arg Gly Asp Tyr Arg Tyr Asp Gly Phe Ala Tyr Trp Gly Gln Gly
            100                 105                 110

Thr Leu Val Thr Val Ser Thr
        115

<210> SEQ ID NO 38
<211> LENGTH: 321
<212> TYPE: DNA
<213> ORGANISM: Mus musculus

<400> SEQUENCE: 38

```
gacatccaga tgactcagtc tccagcttcc ctgtctgcat ctgtgggaga aactgtcacc      60
atcacatgtc gagcaagtga gaatattgac agttatttag catggtatca gcagaaacag    120
ggaaaatctc ctcaactcct ggtctatgct tcaacactct agtagatgg tgtgccatca     180
aggttcagtg gcagtagatc aggcacacag ttttctctca aaatcaacag cctgcagtct    240
gaagatgttg cgagatatta ctgtcaacat tattatagta ttccgtatac gttcggatcg    300
gggaccaagc tggaaataaa a                                               321
```

<210> SEQ ID NO 39
<211> LENGTH: 107
<212> TYPE: PRT
<213> ORGANISM: Mus musculus

<400> SEQUENCE: 39

Asp Ile Gln Met Thr Gln Ser Pro Ala Ser Leu Ser Ala Ser Val Gly

```
             1               5                  10                  15
          Glu Thr Val Thr Ile Thr Cys Arg Ala Ser Glu Asn Ile Asp Ser Tyr
                       20                  25                  30

Leu Ala Trp Tyr Gln Gln Lys Gln Gly Lys Ser Pro Gln Leu Leu Val
                       35                  40                  45

Tyr Ala Ser Thr Leu Leu Val Asp Gly Val Pro Ser Arg Phe Ser Gly
                       50                  55                  60

Ser Arg Ser Gly Thr Gln Phe Ser Leu Lys Ile Asn Ser Leu Gln Ser
          65                  70                  75                  80

Glu Asp Val Ala Arg Tyr Tyr Cys Gln His Tyr Tyr Ser Ile Pro Tyr
                       85                  90                  95

Thr Phe Gly Ser Gly Thr Lys Leu Glu Ile Lys
                      100                 105

<210> SEQ ID NO 40
<211> LENGTH: 5
<212> TYPE: PRT
<213> ORGANISM: Mus musculus

<400> SEQUENCE: 40

Ser Tyr Thr Met Ser
1               5

<210> SEQ ID NO 41
<211> LENGTH: 17
<212> TYPE: PRT
<213> ORGANISM: Mus musculus

<400> SEQUENCE: 41

Thr Ile Ser Ser Gly Gly Gly Arg Thr Tyr Tyr Pro Asp Ser Val Lys
1               5                  10                  15

Gly

<210> SEQ ID NO 42
<211> LENGTH: 10
<212> TYPE: PRT
<213> ORGANISM: Mus musculus

<400> SEQUENCE: 42

Gly Asp Tyr Arg Tyr Asp Gly Phe Ala Tyr
1               5                  10

<210> SEQ ID NO 43
<211> LENGTH: 11
<212> TYPE: PRT
<213> ORGANISM: Mus musculus

<400> SEQUENCE: 43

Arg Ala Ser Glu Asn Ile Asp Ser Tyr Leu Ala
1               5                  10

<210> SEQ ID NO 44
<211> LENGTH: 7
<212> TYPE: PRT
<213> ORGANISM: Mus musculus

<400> SEQUENCE: 44

Ala Ser Thr Leu Leu Val Asp
1               5

<210> SEQ ID NO 45
```

<211> LENGTH: 9
<212> TYPE: PRT
<213> ORGANISM: Mus musculus

<400> SEQUENCE: 45

Gln His Tyr Tyr Ser Ile Pro Tyr Thr
1               5

<210> SEQ ID NO 46
<211> LENGTH: 220
<212> TYPE: PRT
<213> ORGANISM: homo sapiens

<400> SEQUENCE: 46

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220

<210> SEQ ID NO 47
<211> LENGTH: 1389
<212> TYPE: DNA
<213> ORGANISM: homo sapiens

<400> SEQUENCE: 47
cgacactcgg cctaggaatt tcccttatct ccttcgcagt gcagctcctt caacctcgcc      60
atggcctctg ccggaatgca gatcctggga gtcgtcctga cactgctggg ctgggtgaat     120
ggcctggtct cctgtgccct gcccatgtgg aaggtgaccg ctttcatcgg caacagcatc     180
gtggtggccc aggtggtgtg ggagggcctg tggatgtcct gcgtggtgca gagcaccggc     240
cagatgcagt gcaaggtgta cgactcactg ctggcgctgc cacaggacct gcaggctgca     300
cgtgccctct gtgtcatcgc cctccttgtg gccctgttcg gcttgctggt ctaccttgct     360

-continued

```
gggggccaagt gtaccacctg tgtggaggag aaggattcca aggcccgcct ggtgctcacc    420
tctgggattg tctttgtcat ctcagggtc ctgacgctaa tccccgtgtg ctggacggcg      480
catgccatca tccgggactt ctataacccc ctggtggctg aggcccaaaa gcgggagctg    540
ggggcctccc tctacttggg ctgggcggcc tcaggccttt tgttgctggg tgggggttg      600 ctgtgctgca cttgcccctc gggggggtcc cagggcccca gccattacat ggcccgctac    660
tcaacatctg cccctgccat ctctcggggg ccctctgagt accctaccaa gaattacgtc    720
tgacgtggag gggaatgggg gctccgctgg cgctagagcc atccagaagt ggcagtgccc    780
aacagctttg ggatgggttc gtaccttttg tttctgcctc ctgctatttt tcttttgact    840
gaggatattt aaaattcatt tgaaaactga gccaaggtgt tgactcagac tctcacttag    900
gctctgctgt ttctcaccct tggatgatgg agccaaagag gggatgcttt gagattctgg    960
atcttgacat gcccatctta gaagccagtc aagctatgga actaatgcgg aggctgcttg   1020
ctgtgctggc tttgcaacaa gacagactgt ccccaagagt tcctgctgct gctggggggct  1080 gggcttccct agatgtcact ggacagctgc cccccatcct actcaggtct ctggagctcc   1140
tctcttcacc cctggaaaaa caaatgatct gttaacaaag gactgcccac ctccggaact   1200
tctgacctct gtttcctccg tcctgataag acgtccaccc cccagggcca ggtcccagct   1260
atgtagaccc ccgccccac ctccaacact gcaccttct gccctgcccc cctcgtctca    1320 cccccttac actcacattt ttatcaaata aagcatgttt tgttagtgca aaaaaaaaa    1380 aaaaaaaaa                                                            1389
```

<210> SEQ ID NO 48
<211> LENGTH: 217
<212> TYPE: PRT
<213> ORGANISM: homo sapiens

<400> SEQUENCE: 48

```
Met Ala Ser Thr Gly Leu Glu Leu Leu Gly Met Thr Leu Ala Val Leu
1               5                   10                  15

Gly Trp Leu Gly Thr Leu Val Ser Cys Ala Leu Pro Leu Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Ala Leu Gly Leu Leu
                85                  90                  95

Val Ala Ile Thr Gly Ala Gln Cys Thr Thr Cys Val Glu Asp Glu Gly
            100                 105                 110

Ala Lys Ala Arg Ile Val Leu Thr Ala Gly Val Ile Leu Leu Leu Ala
        115                 120                 125

Gly Ile Leu Val Leu Ile Pro Val Cys Trp Thr Ala His Ala Ile Ile
    130                 135                 140

Gln Asp Phe Tyr Asn Pro Leu Val Ala Glu Ala Leu Lys Arg Glu Leu
145                 150                 155                 160

Gly Ala Ser Leu Tyr Leu Gly Trp Ala Ala Ala Leu Leu Met Leu
                165                 170                 175

Gly Gly Gly Leu Leu Cys Cys Thr Cys Pro Pro Gln Val Glu Arg
            180                 185                 190
```

```
Pro Arg Gly Pro Arg Leu Gly Tyr Ser Ile Pro Ser Arg Ser Gly Ala
            195                 200                 205

Ser Gly Leu Asp Lys Arg Asp Tyr Val
            210                 215

<210> SEQ ID NO 49
<211> LENGTH: 220
<212> TYPE: PRT
<213> ORGANISM: homo sapiens

<400> SEQUENCE: 49

Met Ser Met Gly Leu Glu Ile Thr Gly Thr Ala Leu Ala Val Leu Gly
  1               5                  10                  15

Trp Leu Gly Thr Ile Val Cys Cys Ala Leu Pro Met Trp Arg Val Ser
             20                  25                  30

Ala Phe Ile Gly Ser Asn Ile Ile Thr Ser Gln Asn Ile Trp Glu Gly
         35                  40                  45

Leu Trp Met Asn Cys Val Val Gln Ser Thr Gly Gln Met Gln Cys Lys
     50                  55                  60

Val Tyr Asp Ser Leu Leu Ala Leu Pro Gln Asp Leu Gln Ala Ala Arg
 65                  70                  75                  80

Ala Leu Ile Val Val Ala Ile Leu Leu Ala Ala Phe Gly Leu Leu Val
                 85                  90                  95

Ala Leu Val Gly Ala Gln Cys Thr Asn Cys Val Gln Asp Asp Thr Ala
            100                 105                 110

Lys Ala Lys Ile Thr Ile Val Ala Gly Val Leu Phe Leu Leu Ala Ala
            115                 120                 125

Leu Leu Thr Leu Val Pro Val Ser Trp Ser Ala Asn Thr Ile Ile Arg
        130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Leu Gln Leu Leu Gly Gly
                165                 170                 175

Gly Ala Leu Leu Cys Cys Ser Cys Pro Pro Arg Glu Lys Lys Tyr Thr
            180                 185                 190

Ala Thr Lys Val Val Tyr Ser Ala Pro Arg Ser Thr Gly Pro Gly Ala
            195                 200                 205

Ser Leu Gly Thr Gly Tyr Asp Arg Lys Asp Tyr Val
            210                 215                 220

<210> SEQ ID NO 50
<211> LENGTH: 209
<212> TYPE: PRT
<213> ORGANISM: homo sapiens

<400> SEQUENCE: 50

Met Ala Ser Met Gly Leu Gln Val Met Gly Ile Ala Leu Ala Val Leu
  1               5                  10                  15

Gly Trp Leu Ala Val Met Leu Cys Cys Ala Leu Pro Met Trp Arg Val
             20                  25                  30

Thr Ala Phe Ile Gly Ser Asn Ile Val Thr Ser Gln Thr Ile Trp Glu
         35                  40                  45

Gly Leu Trp Met Asn Cys Val Val Gln Ser Thr Gly Gln Met Gln Cys
     50                  55                  60

Lys Val Tyr Asp Ser Leu Leu Ala Leu Pro Gln Asp Leu Gln Ala Ala
 65                  70                  75                  80
```

Arg Ala Leu Val Ile Ile Ser Ile Ile Val Ala Ala Leu Gly Val Leu
                85                  90                  95

Leu Ser Val Val Gly Gly Lys Cys Thr Asn Cys Leu Glu Asp Glu Ser
            100                 105                 110

Ala Lys Ala Lys Thr Met Ile Val Ala Gly Val Val Phe Leu Leu Ala
        115                 120                 125

Gly Leu Met Val Ile Val Pro Val Ser Trp Thr Ala His Asn Ile Ile
    130                 135                 140

Gln Asp Phe Tyr Asn Pro Leu Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175

Gly Gly Gly Leu Leu Cys Cys Asn Cys Pro Pro Arg Thr Asp Lys Pro
                180                 185                 190

Tyr Ser Ala Lys Tyr Ser Ala Ala Arg Ser Ala Ala Ala Ser Asn Tyr
                195                 200                 205

Val

<210> SEQ ID NO 51
<211> LENGTH: 211
<212> TYPE: PRT
<213> ORGANISM: homo sapiens

<400> SEQUENCE: 51

Met Ala Asn Ala Gly Leu Gln Leu Leu Gly Phe Ile Leu Ala Phe Leu
1               5                   10                  15

Gly Trp Ile Gly Ala Ile Val Ser Thr Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Ser Gln Ser Thr Gly Gln Ile Gln Cys
    50                  55                  60

Lys Val Phe Asp Ser Leu Leu Asn Leu Ser Ser Thr Leu Gln Ala Thr
65                  70                  75                  80

Arg Ala Leu Met Val Val Gly Ile Leu Leu Gly Val Ile Ala Ile Phe
                85                  90                  95

Val Ala Thr Val Gly Met Lys Cys Met Lys Cys Leu Glu Asp Asp Glu
            100                 105                 110

Val Gln Lys Met Arg Met Ala Val Ile Gly Gly Ala Ile Phe Leu Leu
        115                 120                 125

Ala Gly Leu Ala Ile Leu Val Ala Thr Ala Trp Tyr Gly Asn Arg Ile
    130                 135                 140

Val Gln Glu Phe Tyr Asp Pro Met Thr Pro Val Asn Ala Arg Tyr Glu
145                 150                 155                 160

Phe Gly Gln Ala Leu Phe Thr Gly Trp Ala Ala Ala Ser Leu Cys Leu
                165                 170                 175

Leu Gly Gly Ala Leu Leu Cys Cys Ser Cys Pro Arg Lys Thr Thr Ser
                180                 185                 190

Tyr Pro Thr Pro Arg Pro Tyr Pro Lys Pro Ala Pro Ser Ser Gly Lys
                195                 200                 205

Asp Tyr Val
210

<210> SEQ ID NO 52

<211> LENGTH: 453
<212> TYPE: PRT
<213> ORGANISM: Artificial
<220> FEATURE:
<223> OTHER INFORMATION: AE49-11/mIgG2a

<400> SEQUENCE: 52

| | | | | | | | | | | | | | | | |
|---|---|---|---|---|---|---|---|---|---|---|---|---|---|---|---|
| Glu | Val | Gln | Leu | Gln | Gln | Ser | Gly | Pro | Glu | Leu | Val | Lys | Pro | Gly | Ala |
| 1 | | | | 5 | | | | | 10 | | | | | 15 | |
| Ser | Val | Lys | Ile | Ser | Cys | Lys | Ala | Ser | Gly | Tyr | Ser | Phe | Thr | Gly | Tyr |
| | | | 20 | | | | | 25 | | | | | 30 | | |
| Phe | Met | Asn | Trp | Val | Lys | Gln | Ser | His | Gly | Lys | Ser | Leu | Glu | Trp | Ile |
| | | 35 | | | | | 40 | | | | | 45 | | | |
| Gly | Arg | Ile | Asn | Pro | Tyr | Asn | Gly | Asp | Thr | Phe | Tyr | Asn | Gln | Lys | Phe |
| | 50 | | | | | 55 | | | | | 60 | | | | |
| Lys | Gly | Lys | Ala | Thr | Leu | Thr | Val | Asp | Lys | Ser | Ser | Thr | Ala | His | |
| 65 | | | | | 70 | | | | | 75 | | | | | 80 |
| Met | Glu | Leu | Arg | Ser | Leu | Thr | Ser | Glu | Asp | Ser | Ala | Val | Tyr | Tyr | Cys |
| | | | | 85 | | | | | 90 | | | | | 95 | |
| Ala | Arg | Val | Leu | Phe | Leu | Asp | Phe | Asp | Pro | Tyr | Leu | Met | Asp | Tyr | |
| | | | 100 | | | | | 105 | | | | | 110 | | |
| Trp | Gly | Gln | Gly | Thr | Ser | Val | Thr | Val | Ser | Ser | Ala | Ser | Thr | Thr | Ala |
| | | | 115 | | | | | 120 | | | | | 125 | | |
| Pro | Ser | Val | Tyr | Pro | Leu | Ala | Pro | Val | Cys | Gly | Asp | Thr | Thr | Gly | Ser |
| | 130 | | | | | 135 | | | | | 140 | | | | |
| Ser | Val | Thr | Leu | Gly | Cys | Leu | Val | Lys | Gly | Tyr | Phe | Pro | Glu | Pro | Val |
| 145 | | | | | 150 | | | | | 155 | | | | | 160 |
| Thr | Leu | Thr | Trp | Asn | Ser | Gly | Ser | Leu | Ser | Ser | Gly | Val | His | Thr | Phe |
| | | | | 165 | | | | | 170 | | | | | 175 | |
| Pro | Ala | Val | Leu | Gln | Ser | Asp | Leu | Tyr | Thr | Leu | Ser | Ser | Ser | Val | Thr |
| | | | 180 | | | | | 185 | | | | | 190 | | |
| Val | Thr | Ser | Ser | Thr | Trp | Pro | Ser | Gln | Ser | Ile | Thr | Cys | Asn | Val | Ala |
| | | 195 | | | | | 200 | | | | | 205 | | | |
| His | Pro | Ala | Ser | Ser | Thr | Lys | Val | Asp | Lys | Lys | Ile | Glu | Pro | Arg | Gly |
| | 210 | | | | | 215 | | | | | 220 | | | | |
| Pro | Thr | Ile | Lys | Pro | Cys | Pro | Pro | Cys | Lys | Cys | Pro | Ala | Pro | Asn | Leu |
| 225 | | | | | 230 | | | | | 235 | | | | | 240 |
| Leu | Gly | Gly | Pro | Ser | Val | Phe | Ile | Phe | Pro | Pro | Lys | Ile | Lys | Asp | Val |
| | | | | 245 | | | | | 250 | | | | | 255 | |
| Leu | Met | Ile | Ser | Leu | Ser | Pro | Ile | Val | Thr | Cys | Val | Val | Val | Asp | Val |
| | | | 260 | | | | | 265 | | | | | 270 | | |
| Ser | Glu | Asp | Asp | Pro | Asp | Val | Gln | Ile | Ser | Trp | Phe | Val | Asn | Asn | Val |
| | | 275 | | | | | 280 | | | | | 285 | | | |
| Glu | Val | His | Thr | Ala | Gln | Thr | Gln | Thr | His | Arg | Glu | Asp | Tyr | Asn | Ser |
| | 290 | | | | | 295 | | | | | 300 | | | | |
| Thr | Leu | Arg | Val | Val | Ser | Ala | Leu | Pro | Ile | Gln | His | Gln | Asp | Trp | Met |
| 305 | | | | | 310 | | | | | 315 | | | | | 320 |
| Ser | Gly | Lys | Glu | Phe | Lys | Cys | Lys | Val | Asn | Asn | Lys | Asp | Leu | Pro | Ala |
| | | | | 325 | | | | | 330 | | | | | 335 | |
| Pro | Ile | Glu | Arg | Thr | Ile | Ser | Lys | Pro | Lys | Gly | Ser | Val | Arg | Ala | Pro |
| | | | 340 | | | | | 345 | | | | | 350 | | |
| Gln | Val | Tyr | Val | Leu | Pro | Pro | Glu | Glu | Glu | Met | Thr | Lys | Lys | Gln | |
| | | 355 | | | | | 360 | | | | | 365 | | | |
| Val | Thr | Leu | Thr | Cys | Met | Val | Thr | Asp | Phe | Met | Pro | Glu | Asp | Ile | Tyr |
| | 370 | | | | | 375 | | | | | 380 | | | | |

```
Val Glu Trp Thr Asn Asn Gly Lys Thr Glu Leu Asn Tyr Lys Asn Thr
385                 390                 395                 400

Glu Pro Val Leu Asp Ser Asp Gly Ser Tyr Phe Met Tyr Ser Lys Leu
            405                 410                 415

Arg Val Glu Lys Lys Asn Trp Val Glu Arg Asn Ser Tyr Ser Cys Ser
        420                 425                 430

Val Val His Glu Gly Leu His Asn His His Thr Thr Lys Ser Phe Ser
        435                 440                 445

Arg Thr Pro Gly Lys
    450

<210> SEQ ID NO 53
<211> LENGTH: 213
<212> TYPE: PRT
<213> ORGANISM: Artificial
<220> FEATURE:
<223> OTHER INFORMATION: AE49-11/mIgG2a

<400> SEQUENCE: 53

Glu Asn Val Leu Thr Gln Ser Pro Ala Ile Met Ser Ala Thr Leu Gly
1               5                   10                  15

Glu Lys Val Thr Met Ser Cys Arg Ala Thr Ser Asn Val Lys Tyr Met
            20                  25                  30

Tyr Trp Tyr Gln Gln Lys Ser Gly Ala Ser Pro Lys Leu Trp Ile Tyr
        35                  40                  45

Tyr Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Val Glu Ala Ala
65                  70                  75                  80

Asp Ala Ala Thr Tyr Tyr Cys Gln Gln Phe Thr Ser Ser Pro Ser Thr
                85                  90                  95

Phe Gly Ala Gly Thr Lys Leu Glu Leu Lys Arg Thr Val Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```